(12) United States Patent
Lynn et al.

(10) Patent No.: US 10,354,753 B2
(45) Date of Patent: Jul. 16, 2019

(54) MEDICAL FAILURE PATTERN SEARCH ENGINE

(71) Applicant: Lawrence A. Lynn, Columbus, OH (US)

(72) Inventors: Lawrence A. Lynn, Columbus, OH (US); Eric N. Lynn, Villa Ridge, MO (US)

(73) Assignee: Lawrence A. Lynn, Columbus, OH (US)

( * ) Notice: Subject to any disclaimer, the term of this patent is extended or adjusted under 35 U.S.C. 154(b) by 38 days.

(21) Appl. No.: 13/843,481

(22) Filed: Mar. 15, 2013

(65) Prior Publication Data

US 2013/0218600 A1 Aug. 22, 2013
US 2016/0378952 A9 Dec. 29, 2016

Related U.S. Application Data

(63) Continuation of application No. 12/437,385, filed on May 7, 2009, and a continuation-in-part of (Continued)

(51) Int. Cl.
G06Q 50/24 (2012.01)
G16H 15/00 (2018.01)
(Continued)

(52) U.S. Cl.
CPC ............ *G16H 15/00* (2018.01); *G06F 19/00* (2013.01); *G06Q 50/24* (2013.01); *G16H 50/20* (2018.01); *G16H 50/70* (2018.01); *G16H 10/60* (2018.01)

(58) Field of Classification Search
CPC ................................ G06Q 50/22; G06Q 50/24
(Continued)

(56) References Cited

U.S. PATENT DOCUMENTS 3,638,640 A 2/1972 Shaw
3,646,606 A 2/1972 Buxton
(Continued)

FOREIGN PATENT DOCUMENTS

DE 2450900 5/1975
EP 0178197 A1 4/1986
(Continued)

OTHER PUBLICATIONS

Apostolopoulou, Eleni et al, Infection Probability Score, APACHE II and KARNOFSKY scoring systems as predictors of bloodstream infection onset in hematology-oncology patients, BMC Infectious Diseases, 2010, vol. 10, No. 135, 8 pages.
(Continued)

*Primary Examiner* — Jonathan Ng
(74) *Attorney, Agent, or Firm* — Vorys, Sater, Seymour and Pease LLP; Rex W. Miller, II

(57) ABSTRACT

A patient safety search engine and alarm processor is programmed to repetitively search the electronic medical records of all patients in a hospital system to automatically provide early detection of patients with evolving pathophysiologic cascades, and in particular the cascades of evolving death, such as cascades of septic shock. The search engine also searches for a wide range of evolving pathophysiologic failures which are commonly fatal if detected too late. An alarm processor is provided which is programmed to provide an alarm upon the detection of a cascade or failure. The processor is further be programmed to provide an image of the cascade, and to determine, the severity of the cascade, and the time of onset of the cascade in relation to the timing and type of procedures and treatment and the increased cost associated with the cascade. Discretionary real-time system-wide searches for a wide range of clinical failure patterns or images within the
(Continued)

hospital system may be performed using the disclosed patient safety search engine.

24 Claims, 28 Drawing Sheets

Related U.S. Application Data application No. 12/437,417, filed on May 7, 2009, now Pat. No. 9,053,222, and a continuation-in-part of application No. 12/629,407, filed on Dec. 2, 2009, which is a continuation of application No. 10/150,842, filed on May 17, 2002, now Pat. No. 7,758,503, said application No. 13/843,481 is a continuation-in-part of application No. 11/369,355, filed on Mar. 7, 2006, now abandoned, which is a continuation of application No. 10/150,582, filed on May 17, 2002, now Pat. No. 7,081,095, said application No. 13/843,481 is a continuation-in-part of application No. 12/152,747, filed on May 16, 2008, now abandoned.

(60) Provisional application No. 61/126,906, filed on May 7, 2008, provisional application No. 61/200,162, filed on Nov. 25, 2008, provisional application No. 60/291,691, filed on May 17, 2001, provisional application No. 60/291,687, filed on May 17, 2001, provisional application No. 60/295,484, filed on Jun. 1, 2001.

(51) Int. Cl.
*G16H 50/70* (2018.01)
*G16H 50/20* (2018.01)
*G06F 19/00* (2018.01)
*G16H 10/60* (2018.01)

(58) Field of Classification Search
USPC .......................................................... 705/2, 3
See application file for complete search history.

(56) References Cited

U.S. PATENT DOCUMENTS

| | | |
|---|---|---|
| 3,884,219 A | 5/1975 | Richardson et al. |
| 3,926,177 A | 12/1975 | Hardway et al. |
| 3,999,537 A | 12/1976 | Noiles |
| 4,022,353 A | 5/1977 | Hamlin |
| 4,036,211 A | 7/1977 | Veth et al. |
| 4,141,354 A | 2/1979 | Ismach |
| 4,340,044 A | 7/1982 | Levy et al. |
| 4,696,307 A | 9/1987 | Montgieux |
| 4,714,341 A | 12/1987 | Hamaguri |
| 4,800,495 A | 1/1989 | Smith |
| 4,805,623 A | 2/1989 | Jobis |
| 4,807,631 A | 2/1989 | Hersh et al. |
| 4,838,275 A | 6/1989 | Lee |
| 4,846,195 A | 7/1989 | Alt |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 4,995,400 A | 2/1991 | Boehringer et al. |
| 5,028,787 A | 7/1991 | Rosenthal et al. |
| 5,065,749 A | 11/1991 | Hasebe et al. |
| 5,066,859 A | 11/1991 | Karkar et al. |
| 5,072,737 A | 12/1991 | Goulding |
| 5,084,327 A | 1/1992 | Stengel |
| 5,092,326 A | 3/1992 | Winn et al. |
| 5,094,246 A | 3/1992 | Rusz et al. |
| 5,119,815 A | 6/1992 | Chance |
| 5,122,974 A | 6/1992 | Chance |
| 5,143,078 A | 9/1992 | Mather et al. |
| 5,167,230 A | 12/1992 | Chance |
| 5,190,038 A | 3/1993 | Polson et al. |
| 5,238,001 A | 8/1993 | Gallant et al. |
| 5,246,003 A | 9/1993 | DeLonzor |
| 5,247,931 A | 9/1993 | Norwood |
| 5,253,645 A | 10/1993 | Friedman et al. |
| 5,263,244 A | 11/1993 | Centa et al. |
| 5,269,310 A | 12/1993 | Jones et al. |
| 5,279,295 A | 1/1994 | Martens et al. |
| 5,285,783 A | 2/1994 | Secker |
| 5,297,548 A | 3/1994 | Pologe |
| 5,309,908 A | 5/1994 | Friedman et al. |
| 5,312,454 A | 5/1994 | Roline et al. |
| 5,355,880 A | 10/1994 | Thomas et al. |
| 5,372,136 A | 12/1994 | Steuer et al. |
| 5,385,143 A | 1/1995 | Aoyagi |
| 5,390,666 A | 2/1995 | Kimm et al. |
| 5,390,670 A | 2/1995 | Centa et al. |
| 5,413,099 A | 5/1995 | Schmidt et al. |
| 5,423,327 A | 6/1995 | Clauson et al. |
| 5,469,845 A | 11/1995 | DeLonzor et al. |
| 5,482,036 A | 1/1996 | Diab et al. |
| 5,520,176 A | 5/1996 | Cohen |
| 5,558,086 A | 9/1996 | Smith et al. |
| 5,483,646 A | 10/1996 | Uchikoga |
| 5,553,614 A | 10/1996 | Chance |
| 5,564,417 A | 10/1996 | Chance |
| 5,575,285 A | 11/1996 | Takanashi et al. |
| 5,584,298 A | 12/1996 | Kabal |
| 5,611,337 A | 3/1997 | Bukta |
| 5,619,991 A | 4/1997 | Sloane |
| 5,630,413 A | 5/1997 | Thomas et al. |
| 5,639,617 A | 6/1997 | Bohuon |
| 5,645,059 A | 7/1997 | Fein et al. |
| 5,645,060 A | 7/1997 | Yorkey |
| 5,660,171 A | 8/1997 | Kimm et al. |
| 5,680,857 A | 10/1997 | Pelikan et al. |
| 5,692,503 A | 12/1997 | Keunstner |
| 5,716,384 A | 2/1998 | Snell |
| 5,724,580 A | 3/1998 | Levin et al. |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hok |
| 5,800,348 A | 9/1998 | Kaestle |
| 5,804,370 A | 9/1998 | Romaschin et al. |
| 5,822,544 A | 10/1998 | Chaco et al. |
| 5,830,136 A | 11/1998 | DeLonzor et al. |
| 5,830,139 A | 11/1998 | Abreu |
| 5,831,598 A | 11/1998 | Kauffert et al. |
| 5,840,019 A | 11/1998 | Wirebaugh |
| 5,842,981 A | 12/1998 | Larsen et al. |
| 5,846,190 A | 12/1998 | Woehrle |
| 5,862,802 A | 1/1999 | Bird |
| 5,865,174 A | 2/1999 | Kloeppel |
| 5,871,442 A | 2/1999 | Madarasz et al. |
| 5,873,821 A | 2/1999 | Chance et al. |
| 5,920,263 A | 7/1999 | Huttenhoff et al. |
| 5,931,790 A | 8/1999 | Peel, III |
| 5,935,099 A | 8/1999 | Peterson et al. |
| 5,942,986 A | 8/1999 | Shabot et al. |
| 5,995,855 A | 11/1999 | Kiani et al. |
| 5,995,856 A | 11/1999 | Mannheimer et al. |
| 5,995,859 A | 11/1999 | Takahashi |
| 6,002,952 A | 12/1999 | Diab et al. |
| 6,004,276 A | 12/1999 | Wright et al. |
| 6,011,986 A | 1/2000 | Diab et al. |
| 6,024,699 A | 2/2000 | Surwit et al. |
| 6,050,951 A | 4/2000 | Friedman et al. |
| 6,064,898 A | 5/2000 | Aldrich |
| 6,067,462 A | 5/2000 | Diab et al. |
| 6,070,098 A | 5/2000 | Moore-Ede et al. |
| 6,081,742 A | 6/2000 | Amano et al. |
| 6,083,172 A | 7/2000 | Baker, Jr. et al. |
| 6,088,607 A | 7/2000 | Diab et al. |

(56) References Cited

U.S. PATENT DOCUMENTS

| | | |
|---|---|---|
| 6,095,984 A | 8/2000 | Amano et al. |
| 6,102,038 A | 8/2000 | DeVries |
| 6,102,870 A | 8/2000 | Edwards |
| 6,120,460 A | 9/2000 | Abreu |
| 6,134,460 A | 10/2000 | Chance |
| 6,141,590 A | 10/2000 | Renirie et al. |
| 6,148,814 A | 11/2000 | Clemmer et al. |
| 6,150,951 A | 11/2000 | Olejniczak |
| 6,151,516 A | 11/2000 | Kiani-Azarbayjany et al. |
| 6,154,667 A | 11/2000 | Miura et al. |
| 6,159,683 A | 12/2000 | Romaschin et al. |
| 6,163,715 A | 12/2000 | Larsen et al. |
| 6,171,258 B1 | 1/2001 | Karakasoglu et al. |
| 6,181,958 B1 | 1/2001 | Steuer et al. |
| 6,181,959 B1 | 1/2001 | Schollermann et al. |
| 6,230,035 B1 | 5/2001 | Aoyagi et al. |
| 6,230,142 B1 | 5/2001 | Benigno et al. |
| 6,230,708 B1 | 5/2001 | Radko |
| 6,266,546 B1 | 7/2001 | Steuer et al. |
| 6,285,895 B1 | 9/2001 | Ristolainen et al. |
| 6,312,393 B1 | 11/2001 | Abreu |
| 6,322,515 B1 | 11/2001 | Goor et al. |
| 6,353,750 B1 | 3/2002 | Kimura et al. |
| 6,363,270 B1 | 3/2002 | Colla et al. |
| 6,364,834 B1 | 4/2002 | Reuss et al. |
| 6,385,589 B1 | 5/2002 | Trusheim et al. |
| 6,393,311 B1 | 5/2002 | Edgar, Jr. et al. |
| 6,397,091 B2 | 5/2002 | Diab et al. |
| 6,397,099 B1 | 5/2002 | Chance |
| 6,398,727 B1 | 6/2002 | Bui et al. |
| 6,411,833 B1 | 6/2002 | Baker, Jr. et al. |
| 6,415,166 B1 | 7/2002 | Van Hoy et al. |
| 6,415,175 B1 | 7/2002 | Conley et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,475,153 B1 | 11/2002 | Khair et al. |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,553,242 B1 | 4/2003 | Sarussi |
| 6,571,622 B2 | 6/2003 | Koch |
| 6,579,242 B2 | 6/2003 | Bui et al. |
| 6,580,086 B1 | 6/2003 | Schultz et al. |
| 6,583,794 B1 | 6/2003 | Wattenberg |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,659,961 B2 | 12/2003 | Robinson |
| 6,662,030 B2 | 12/2003 | Khalil et al. |
| 6,662,032 B1 | 12/2003 | Gavish et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,697,658 B2 | 2/2004 | Al-Ali |
| 6,699,194 B1 | 3/2004 | Diab et al. |
| 6,708,048 B1 | 3/2004 | Chance |
| 6,711,424 B1 | 3/2004 | Fine et al. |
| 6,711,425 B1 | 3/2004 | Reuss et al. |
| 6,714,245 B1 | 3/2004 | Ono |
| 6,721,584 B2 | 4/2004 | Baker, Jr. et al. |
| 6,723,077 B2 | 4/2004 | Pickup et al. |
| 6,731,274 B2 | 5/2004 | Powell |
| 6,738,666 B1 | 5/2004 | Park et al. |
| 6,752,150 B1 | 6/2004 | Remmers et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes |
| 6,801,799 B2 | 10/2004 | Mendelson |
| 6,810,277 B2 | 10/2004 | Edgar, Jr. et al. |
| 6,816,266 B2 | 11/2004 | Varshneya et al. |
| 6,820,618 B2 | 11/2004 | Banner et al. |
| 6,829,496 B2 | 12/2004 | Nagai et al. |
| 6,830,549 B2 | 12/2004 | Bui et al. |
| 6,836,679 B2 | 12/2004 | Baker, Jr. et al. |
| 6,839,581 B1 | 1/2005 | El-Solh et al. |
| 6,850,053 B2 | 2/2005 | Daalmans et al. |
| 6,863,652 B2 | 3/2005 | Huang et al. |
| 6,869,402 B2 | 3/2005 | Arnold |
| 6,873,865 B2 | 3/2005 | Steuer et al. |
| 6,889,153 B2 | 5/2005 | Dietiker |
| 6,898,451 B2 | 5/2005 | Wuori |
| 6,918,878 B2 | 7/2005 | Brodnick |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,963,767 B2 | 11/2005 | Rantala et al. |
| 6,983,178 B2 | 1/2006 | Fine et al. |
| 6,985,762 B2 | 1/2006 | Brashears et al. |
| 6,993,371 B2 | 1/2006 | Kiani et al. |
| 6,994,675 B2 | 2/2006 | Sharrock |
| 6,996,427 B2 | 2/2006 | Ali et al. |
| 7,013,898 B2 | 3/2006 | Rashad et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,034,692 B2 | 4/2006 | Hickle |
| 7,035,679 B2 | 4/2006 | Addison et al. |
| 7,035,697 B1 | 4/2006 | Brown |
| 7,040,315 B1 | 5/2006 | Stromberg |
| 7,044,917 B2 | 5/2006 | Arnold |
| 7,047,056 B2 | 5/2006 | Hannula et al. |
| 7,081,095 B2 | 7/2006 | Lynn et al. |
| 7,118,534 B2 | 10/2006 | Ward et al. |
| 7,127,278 B2 | 10/2006 | Melker et al. |
| 7,139,599 B2 | 11/2006 | Terry |
| 7,161,484 B2 | 1/2007 | Tsoukalis |
| 7,162,306 B2 | 1/2007 | Caby et al. |
| 7,171,269 B1 | 1/2007 | Addison et al. |
| 7,186,217 B2 | 3/2007 | Kawasaki |
| 7,188,621 B2 | 3/2007 | DeVries et al. |
| 7,190,261 B2 | 3/2007 | Al-Ali |
| 7,190,995 B2 | 3/2007 | Chervin et al. |
| 7,209,775 B2 | 4/2007 | Bae et al. |
| 7,218,966 B2 | 5/2007 | Haefner |
| 7,220,220 B2 | 5/2007 | Stubbs et al. |
| 7,222,623 B2 | 5/2007 | DeVries et al. |
| 7,231,240 B2 | 6/2007 | Eda et al. |
| 7,236,811 B2 | 6/2007 | Schmitt |
| 7,239,905 B2 | 7/2007 | Kiani-Azarbayjany et al. |
| 7,252,637 B2 | 8/2007 | Ebner et al. |
| 7,263,395 B2 | 8/2007 | Chan et al. |
| 7,267,652 B2 | 9/2007 | Coyle et al. |
| 7,272,426 B2 | 9/2007 | Schmidt et al. |
| 7,309,314 B2 | 12/2007 | Grant et al. |
| 7,338,447 B2 | 3/2008 | Phillips |
| 7,353,054 B2 | 4/2008 | Kawasaki et al. |
| 7,366,569 B2 | 4/2008 | Belalcazar |
| 7,367,339 B2 | 5/2008 | Hickle |
| 7,367,954 B2 | 5/2008 | Starr et al. |
| 7,370,650 B2 | 5/2008 | Nadjafizadeh et al. |
| 7,373,193 B2 | 5/2008 | Al-Ali et al. |
| 7,407,485 B2 | 8/2008 | Huiku |

(56) References Cited

U.S. PATENT DOCUMENTS

| | | |
|---|---|---|
| 7,407,486 B2 | 8/2008 | Huiku et al. |
| 7,421,296 B1 | 9/2008 | Benser et al. |
| 7,428,520 B2 | 9/2008 | Armstrong et al. |
| 7,447,541 B2 | 11/2008 | Huiku et al. |
| 7,460,909 B1 | 12/2008 | Koh et al. |
| 7,488,293 B2 | 2/2009 | Marchovecchio |
| 7,499,835 B2 | 3/2009 | Weber |
| 7,539,537 B2 | 5/2009 | Hickle |
| 7,544,190 B2 | 6/2009 | Pickup et al. |
| 7,632,685 B2 | 12/2009 | Ivey et al. |
| 7,635,337 B2 | 12/2009 | Huika et al. |
| 7,640,055 B2 | 12/2009 | Geva et al. |
| 7,645,613 B2 | 1/2010 | Ivey et al. |
| 7,659,075 B2 | 2/2010 | Bergmann |
| 7,668,579 B2 | 2/2010 | Lynn |
| 7,674,230 B2 | 3/2010 | Reisfeld |
| 7,723,492 B2 | 5/2010 | Bergmann et al. |
| 7,758,503 B2 | 7/2010 | Lynn et al. |
| 7,785,262 B2 | 8/2010 | Melker et al. |
| 7,792,642 B1 | 9/2010 | Neilley et al. |
| 7,794,406 B2 | 9/2010 | Reisfeld et al. |
| 7,803,118 B2 | 9/2010 | Reisfeld et al. |
| 7,803,119 B2 | 9/2010 | Reisfeld |
| 7,806,832 B2 | 10/2010 | Gallagher et al. |
| 8,275,553 B2 | 9/2012 | Ochs et al. |
| 8,365,730 B2 | 2/2013 | Baker, Jr. et al. |
| 8,398,555 B2 | 3/2013 | Ochs et al. |
| 8,439,835 B1 | 5/2013 | McKinley et al. |
| 8,527,449 B2 | 9/2013 | Gajic et al. |
| 8,663,107 B2 | 3/2014 | Kiani |
| 8,666,467 B2 | 3/2014 | Lynn et al. |
| 8,728,001 B2 | 5/2014 | Lynn |
| 8,781,753 B2 | 7/2014 | Ivey et al. |
| 9,042,952 B2 | 5/2015 | Lynn et al. |
| 2001/0005773 A1 | 6/2001 | Larsen et al. |
| 2001/0018557 A1 | 8/2001 | Lynn et al. |
| 2001/0020122 A1 | 9/2001 | Steuer et al. |
| 2001/0039376 A1 | 11/2001 | Steuer et al. |
| 2001/0044588 A1 | 11/2001 | Mault |
| 2001/0044700 A1 | 11/2001 | Kobayashi et al. |
| 2002/0002327 A1 | 1/2002 | Grant et al. |
| 2002/0026106 A1 | 2/2002 | Khalil et al. |
| 2002/0026941 A1 | 3/2002 | Biondi et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0052557 A1 | 5/2002 | Griffin et al. |
| 2002/0062071 A1 | 5/2002 | Diab et al. |
| 2002/0082488 A1 | 6/2002 | Al-Ali et al. |
| 2002/0091326 A1 | 7/2002 | Hashimoto et al. |
| 2002/0095090 A1 | 7/2002 | Caro et al. |
| 2002/0099273 A1* | 7/2002 | Bocionek et al. ............ 600/300 |
| 2002/0111748 A1 | 8/2002 | Kobayashi et al. |
| 2002/0128544 A1 | 9/2002 | Diab et al. |
| 2002/0133068 A1 | 9/2002 | Huiku |
| 2002/0138014 A1 | 9/2002 | Baura et al. |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0165462 A1 | 11/2002 | Westbrook et al. |
| 2002/0198443 A1 | 12/2002 | Ting |
| 2003/0000522 A1 | 1/2003 | Lynn et al. |
| 2003/0023140 A1 | 1/2003 | Chance |
| 2003/0055324 A1 | 3/2003 | Wasserman |
| 2003/0055331 A1 | 3/2003 | Kotmel et al. |
| 2003/0060693 A1 | 3/2003 | Monfre et al. |
| 2003/0101076 A1 | 5/2003 | Zaleski |
| 2003/0127097 A1 | 7/2003 | Yurko |
| 2003/0135127 A1 | 7/2003 | Sackner et al. |
| 2003/0139687 A1 | 7/2003 | Abreu |
| 2003/0144584 A1 | 7/2003 | Mendelson |
| 2003/0150842 A1 | 8/2003 | Mikame |
| 2003/0158466 A1* | 8/2003 | Lynn et al. ............ 600/300 |
| 2003/0181815 A1 | 9/2003 | Ebner et al. |
| 2003/0194752 A1 | 10/2003 | Anderson et al. |
| 2003/0220548 A1 | 11/2003 | Schmitt |
| 2003/0220576 A1 | 11/2003 | Diab |
| 2003/0228625 A1 | 12/2003 | Toh et al. |
| 2004/0010188 A1 | 1/2004 | Wasserman |
| 2004/0039295 A1 | 2/2004 | Olbrich et al. |
| 2004/0044276 A1 | 3/2004 | Arnold |
| 2004/0048264 A1 | 3/2004 | Stoughton et al. |
| 2004/0054270 A1 | 3/2004 | Pewzner et al. |
| 2004/0064020 A1 | 4/2004 | Diab et al. |
| 2004/0073098 A1 | 4/2004 | Geva et al. |
| 2004/0078219 A1 | 4/2004 | Kaylor et al. |
| 2004/0078228 A1 | 4/2004 | Fitzgerald et al. |
| 2004/0087846 A1 | 5/2004 | Wasserman |
| 2004/0087916 A1 | 5/2004 | Pickup |
| 2004/0096917 A1 | 5/2004 | Ivey et al. |
| 2004/0097460 A1 | 5/2004 | Ivey et al. |
| 2004/0106142 A1 | 6/2004 | Ivey et al. |
| 2004/0107065 A1 | 6/2004 | Al-Ali |
| 2004/0127779 A1 | 7/2004 | Steuer et al. |
| 2004/0128163 A1* | 7/2004 | Goodman et al. ............ 705/2 |
| 2004/0157242 A1 | 8/2004 | Ivey et al. |
| 2004/0158135 A1 | 8/2004 | Baker, Jr. et al. |
| 2004/0162499 A1 | 8/2004 | Nagai et al. |
| 2004/0163648 A1 | 8/2004 | Burton |
| 2004/0170154 A1 | 9/2004 | Carter et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0181134 A1 | 9/2004 | Baker, Jr. et al. |
| 2004/0181196 A1 | 9/2004 | Pickup et al. |
| 2004/0183683 A1 | 9/2004 | Funahashi |
| 2004/0204637 A1 | 10/2004 | Diab et al. |
| 2004/0230105 A1 | 11/2004 | Geva et al. |
| 2004/0230106 A1 | 11/2004 | Schmitt et al. |
| 2004/0249299 A1 | 12/2004 | Cobb |
| 2004/0254481 A1 | 12/2004 | Brodnick |
| 2004/0254490 A1 | 12/2004 | Egli |
| 2005/0001728 A1 | 1/2005 | Appelt et al. |
| 2005/0017864 A1 | 1/2005 | Tsoukalis |
| 2005/0027207 A1 | 2/2005 | Westbrook et al. |
| 2005/0033129 A1 | 2/2005 | Edgar, Jr. et al. |
| 2005/0043616 A1 | 2/2005 | Chinchoy |
| 2005/0065556 A1 | 3/2005 | Reghabi et al. |
| 2005/0070774 A1 | 3/2005 | Addison et al. |
| 2005/0080323 A1 | 4/2005 | Kato |
| 2005/0098178 A1 | 5/2005 | Banner et al. |
| 2005/0101850 A1 | 5/2005 | Parker |
| 2005/0109340 A1 | 5/2005 | Tehrani |
| 2005/0113651 A1 | 5/2005 | Wood et al. |
| 2005/0113656 A1 | 5/2005 | Chance |
| 2005/0113709 A1 | 5/2005 | Millett |
| 2005/0119586 A1 | 6/2005 | Coyle et al. |
| 2005/0119708 A1 | 6/2005 | Haefner |
| 2005/0125256 A1 | 6/2005 | Schoenberg et al. |
| 2005/0143665 A1 | 6/2005 | Huiku et al. |
| 2005/0154422 A1 | 7/2005 | Band et al. |
| 2005/0164238 A1 | 7/2005 | Valkirs et al. |
| 2005/0168722 A1 | 8/2005 | Forstner et al. |
| 2005/0177034 A1 | 8/2005 | Beaumont |
| 2005/0181354 A1 | 8/2005 | Estep, III |
| 2005/0187480 A1 | 8/2005 | Kario et al. |
| 2005/0192488 A1 | 9/2005 | Bryenton et al. |
| 2005/0192500 A1 | 9/2005 | Caro et al. |
| 2005/0203357 A1 | 9/2005 | Debreczeny et al. |
| 2005/0209521 A1 | 9/2005 | Kettunen et al. |
| 2005/0222503 A1 | 10/2005 | Dunlop et al. |
| 2005/0228248 A1 | 10/2005 | Dietiker |
| 2005/0240091 A1 | 10/2005 | Lynn |
| 2005/0245830 A1 | 11/2005 | Hutchinson |
| 2005/0247311 A1 | 11/2005 | Vacchiano et al. |
| 2005/0251056 A1 | 11/2005 | Gribkov et al. |
| 2005/0277819 A1 | 12/2005 | Kian et al. |
| 2005/0283059 A1 | 12/2005 | Iyer et al. |
| 2006/0009688 A1 | 1/2006 | Lamego et al. |
| 2006/0009809 A1 | 1/2006 | Marcovecchio et al. |
| 2006/0015021 A1 | 1/2006 | Cheung |
| 2006/0020181 A1 | 1/2006 | Schmitt |

(56) References Cited

U.S. PATENT DOCUMENTS

| | | |
|---|---|---|
| 2006/0030763 A1 | 2/2006 | Mannheimer et al. |
| 2006/0042631 A1 | 3/2006 | Martin et al. |
| 2006/0052680 A1 | 3/2006 | Diab |
| 2006/0058683 A1 | 3/2006 | Chance |
| 2006/0064024 A1 | 3/2006 | Schnall |
| 2006/0081259 A1 | 4/2006 | Bruggeman et al. |
| 2006/0084854 A1 | 4/2006 | Cho et al. |
| 2006/0137577 A1 | 6/2006 | Chang et al. |
| 2006/0155176 A1 | 7/2006 | Ebner et al. |
| 2006/0157647 A1 | 7/2006 | Siuzdak et al. |
| 2006/0167363 A1 | 7/2006 | Osypka et al. |
| 2006/0189872 A1 | 8/2006 | Arnold |
| 2006/0195028 A1 | 8/2006 | Hannula et al. |
| 2006/0195041 A1 | 8/2006 | Lynn et al. |
| 2006/0200012 A1 | 9/2006 | Mansour et al. |
| 2006/0200016 A1 | 9/2006 | Diab et al. |
| 2006/0217614 A1 | 9/2006 | Takala et al. |
| 2006/0217615 A1 | 9/2006 | Huiku et al. |
| 2006/0217628 A1 | 9/2006 | Huiku |
| 2006/0224058 A1 | 10/2006 | Mannheimer |
| 2006/0235726 A1 | 10/2006 | Paraison et al. |
| 2006/0247501 A1 | 11/2006 | Ali |
| 2006/0258921 A1 | 11/2006 | Addison et al. |
| 2006/0271408 A1 | 11/2006 | Rosenfeld et al. |
| 2006/0287590 A1 | 12/2006 | McEowen |
| 2007/0004957 A1 | 1/2007 | Hilburg |
| 2007/0010723 A1 | 1/2007 | Uutela et al. |
| 2007/0015976 A1 | 1/2007 | Miesel et al. |
| 2007/0027369 A1 | 2/2007 | Pagnacco et al. |
| 2007/0027375 A1 | 2/2007 | Melker et al. |
| 2007/0037873 A1 | 2/2007 | Zurier et al. |
| 2007/0073361 A1 | 3/2007 | Goren et al. |
| 2007/0093701 A1 | 4/2007 | Myers et al. |
| 2007/0142719 A1 | 6/2007 | Kawasaki et al. |
| 2007/0179369 A1 | 8/2007 | Baker, Jr. |
| 2007/0184512 A1 | 8/2007 | Ivey et al. |
| 2007/0203406 A1 | 8/2007 | Anderson et al. |
| 2007/0208269 A1 | 9/2007 | Mumford et al. |
| 2007/0213619 A1 | 9/2007 | Linder |
| 2007/0213620 A1 | 9/2007 | Reisfeld |
| 2007/0213621 A1 | 9/2007 | Reisfeld et al. |
| 2007/0213622 A1 | 9/2007 | Reisfeld |
| 2007/0213624 A1 | 9/2007 | Reisfeld et al. |
| 2007/0225606 A1 | 9/2007 | Naghavi et al. |
| 2007/0225614 A1 | 9/2007 | Naghavi et al. |
| 2007/0238937 A1 | 10/2007 | Chang et al. |
| 2007/0240723 A1 | 10/2007 | Hong et al. |
| 2007/0255146 A1 | 11/2007 | Andrews et al. |
| 2007/0255322 A1 | 11/2007 | Gerber et al. |
| 2007/0282212 A1 | 12/2007 | Sierra et al. |
| 2008/0009689 A1 | 1/2008 | Benaron et al. |
| 2008/0014115 A1 | 1/2008 | Johns |
| 2008/0036752 A1 | 2/2008 | Diab et al. |
| 2008/0050829 A1 | 2/2008 | Ivey et al. |
| 2008/0051764 A1 | 2/2008 | Dent et al. |
| 2008/0064965 A1 | 3/2008 | Jay et al. |
| 2008/0066753 A1 | 3/2008 | Martin et al. |
| 2008/0082018 A1 | 4/2008 | Sackner et al. |
| 2008/0091088 A1* | 4/2008 | Kiani ............... A61B 5/0205 600/301 |
| 2008/0114576 A1 | 5/2008 | Jackson et al. |
| 2008/0138832 A1 | 6/2008 | Ivey et al. |
| 2008/0167540 A1 | 7/2008 | Korhonen et al. |
| 2008/0177163 A1 | 7/2008 | Wang et al. |
| 2008/0183058 A1 | 7/2008 | Mannheimer |
| 2008/0183083 A1 | 7/2008 | Markowitz et al. |
| 2008/0188729 A1 | 8/2008 | Sato et al. |
| 2008/0195322 A1 | 8/2008 | Altschuler et al. |
| 2008/0200781 A1 | 8/2008 | Van Herpen et al. |
| 2008/0208012 A1 | 8/2008 | Ali |
| 2008/0208618 A1 | 8/2008 | Schoenberg et al. |
| 2008/0235049 A1* | 9/2008 | Morita et al. ............... 705/2 |
| 2008/0235057 A1 | 9/2008 | Weidenhaupt et al. |
| 2008/0269583 A1 | 10/2008 | Reisfeld |
| 2008/0269626 A1 | 10/2008 | Gallaher et al. |
| 2008/0269832 A1 | 10/2008 | Wong et al. |
| 2008/0286763 A1 | 11/2008 | Russwurm et al. |
| 2008/0305464 A1 | 12/2008 | Lynn |
| 2008/0312533 A1 | 12/2008 | Balberg et al. |
| 2009/0069704 A1 | 3/2009 | MacAdam et al. |
| 2009/0082641 A1 | 3/2009 | Giftakis et al. |
| 2009/0083072 A1 | 3/2009 | Osawa et al. |
| 2009/0171169 A1 | 7/2009 | Nagata |
| 2009/0186774 A1 | 7/2009 | Turner et al. |
| 2009/0187082 A1 | 7/2009 | Cuddihy et al. |
| 2009/0281838 A1 | 11/2009 | Lynn et al. |
| 2009/0299154 A1 | 12/2009 | Segman |
| 2009/0318775 A1 | 12/2009 | Michelson et al. |
| 2010/0066540 A1 | 3/2010 | Theobald et al. |
| 2010/0070888 A1 | 3/2010 | Watabe et al. |
| 2010/0079292 A1 | 4/2010 | Lynn et al. |
| 2010/0094648 A1 | 4/2010 | Seward |
| 2010/0160171 A1 | 6/2010 | Freishtat |
| 2010/0174161 A1 | 7/2010 | Lynn |
| 2010/0234705 A1 | 9/2010 | Lynn |
| 2010/0261977 A1 | 10/2010 | Seely |
| 2011/0009722 A1 | 1/2011 | Amundson et al. |
| 2011/0009760 A1 | 1/2011 | Zhang et al. |
| 2011/0015501 A1 | 1/2011 | Lynn et al. |
| 2011/0046498 A1 | 2/2011 | Klap et al. |
| 2011/0105350 A1 | 5/2011 | Garrett et al. |
| 2011/0118569 A1 | 5/2011 | Shi et al. |
| 2011/0130671 A1 | 6/2011 | MacQuarrie et al. |
| 2011/0208539 A1 | 8/2011 | Lynn |
| 2012/0053425 A1 | 3/2012 | Michelson et al. |
| 2012/0165623 A1 | 6/2012 | Lynn et al. |
| 2012/0172247 A1 | 7/2012 | Narimatsu et al. |
| 2012/0197094 A1 | 8/2012 | Zhang et al. |
| 2012/0220845 A1 | 8/2012 | Campbell |
| 2012/0232359 A1 | 9/2012 | Al-Ali et al. |
| 2012/0328594 A1 | 12/2012 | McKenna et al. |
| 2012/0330118 A1 | 12/2012 | Lynn et al. |
| 2013/0052671 A1 | 2/2013 | Grueb et al. |
| 2013/0060110 A1 | 3/2013 | Lynn et al. |
| 2013/0073311 A1 | 3/2013 | Lynn et al. |
| 2013/0124221 A1 | 5/2013 | Lynn |
| 2013/0131993 A1 | 5/2013 | Lynn et al. |
| 2013/0158375 A1 | 6/2013 | Lynn |
| 2013/0209068 A1 | 8/2013 | Lynn |
| 2013/0211214 A1 | 8/2013 | Olsen |
| 2013/0218600 A1 | 8/2013 | Lynn et al. |
| 2013/0254717 A1 | 9/2013 | Al-Ali et al. |
| 2013/0262730 A1 | 10/2013 | Al-Ali et al. |
| 2013/0268291 A1 | 10/2013 | Lynn et al. |
| 2013/0274572 A1 | 10/2013 | Al-Ali et al. |
| 2013/0290011 A1 | 10/2013 | Lynn et al. |
| 2013/0338459 A1 | 12/2013 | Lynn |
| 2014/0152673 A1 | 6/2014 | Lynn et al. |
| 2014/0163897 A1 | 6/2014 | Lynn et al. |
| 2014/0176538 A1 | 6/2014 | Lynn et al. |
| 2014/0176558 A1 | 6/2014 | Lynn et al. |
| 2014/0180722 A1 | 6/2014 | Lynn et al. |

FOREIGN PATENT DOCUMENTS

| | | |
|---|---|---|
| EP | 0459647 B1 | 10/1991 |
| EP | 0459284 | 12/1991 |
| EP | 0615723 | 3/1993 |
| EP | 0666056 A1 | 7/1994 |
| EP | 0392503 B1 | 5/1995 |
| EP | 0684011 A1 | 5/1995 |
| EP | 0700690 | 3/1996 |
| EP | 0700690 B1 | 2/2002 |
| EP | 0759791 B1 | 8/2002 |
| EP | 1529487 A1 | 7/2003 |
| EP | 0934 723 | 9/2004 |
| EP | 1172123 B1 | 10/2004 |
| EP | 0875258 B1 | 11/2004 |
| GB | 1554829 | 2/1978 |
| JP | 63275325 | 11/1988 |
| JP | 05-266002 | 10/1993 |
| JP | 5266002 | 10/1993 |
| JP | 2000-042111 | 2/2000 |
| JP | 2002336207 A | 11/2002 |

(56) References Cited

FOREIGN PATENT DOCUMENTS

| | | |
|---|---|---|
| JP | 2005034472 | 2/2005 |
| JP | 2007058565 A | 3/2007 |
| JP | 4435681 B2 | 3/2010 |
| KR | 1020020064206 | 8/2002 |
| WO | WO 86/00234 | 1/1986 |
| WO | WO 92/12750 | 8/1992 |
| WO | WO 93/16629 | 9/1993 |
| WO | WO 94/23780 | 10/1994 |
| WO | WO 96/39927 | 12/1996 |
| WO | WO 97/19719 | 6/1997 |
| WO | WO 98/12965 | 4/1998 |
| WO | WO 98/43071 A1 | 10/1998 |
| WO | WO 99/13766 | 3/1999 |
| WO | WO 00/21438 | 4/2000 |
| WO | WO 00/74551 A2 | 12/2000 |
| WO | WO 01/40776 | 6/2001 |
| WO | WO 01/76461 | 10/2001 |
| WO | WO 01/76471 | 10/2001 |
| WO | WO 01/82099 A1 | 11/2001 |
| WO | WO 01/87149 | 11/2001 |
| WO | WO 02/41771 A1 | 5/2002 |
| WO | WO 03/000125 A1 | 1/2003 |
| WO | WO 03/039326 | 5/2003 |
| WO | WO 03/053780 | 7/2003 |
| WO | 2004056301 A2 | 7/2004 |
| WO | WO 2004056301 | 7/2004 |
| WO | 2004080300 A1 | 9/2004 |
| WO | WO 2004/075746 A2 | 9/2004 |
| WO | WO 2004/105601 A1 | 12/2004 |
| WO | WO 2005/037077 | 4/2005 |
| WO | WO 2005/065540 A1 | 7/2005 |
| WO | WO 2005/096931 A1 | 10/2005 |
| WO | WO 2005/110215 A2 | 11/2005 |
| WO | WO 2006/086010 A2 | 8/2006 |
| WO | WO 2006/116469 A2 | 11/2006 |
| WO | WO 2007/013708 | 2/2007 |
| WO | WO 2007/051006 A2 | 5/2007 |
| WO | WO 2008/008163 A2 | 1/2008 |
| WO | WO 2008/097411 A1 | 8/2008 |
| WO | WO 2008/117338 A1 | 10/2008 |
| WO | WO 2010/108018 A3 | 9/2010 |

OTHER PUBLICATIONS

Bland, RD et al., Probability of Survival as a Prognostic and Severity of Illness Score in Critically Ill Surgical Patients, Crit Care Med., Feb. 1985, pp. 91-95, vol. 13, No. 2 (Abstract).
Burykin, Anton et al., Toward optimal display of physiologic status in critical care: I. Recreating bedside displays from archived physiologic data, Journal of Critical Care, 2010 (Article in Press), 9 pages.
Cavallazzi, MD, Rodrigo, Is the Band Count Useful in the Diagnosis of Infection? An Accuracy Study in Critically Ill Patients, Journal of Intensive Care Medicine, 2010, 5 pages.
Finlay, Heather et al., Designing and Testing a Computer-Based Screening System for Transfusion-Related Acute Lung Injury, Am J Clin Pathol, 2005, vol. 124, pp. 601-609.
Herasevich, Vitaly et al., Designing and testing computer based screening engine for severe sepsis/septic shock, AMIA Annu Symp Proc. Nov. 2008 (Abstract).
Herasevich, Vitaly et al., Enrollment into a time sensitive clinical study in the critical care setting: results from computerized septic shock sniffer implementation, J Am Med Inform Assoc, 2011, vol. 18, pp. 639-644.
Herasevich, Vitaly et al., Limiting ventilator-induced lung injury through individual electronic medical record surveillance, Crit Care Med, 2011, vol. 39, No. 1, pp. 34-39.
Herasevich, Vitaly et al., Validation of an electronic surveillance system for acute lung injury, Intensive Care Med., Jun. 2009, vol. 35, No. 6, pp. 118-1023.
Lu, K, et al., A Mathematical Program to Predict Survival and to Support Initial Therapeutic Decisions for Trauma Patients With Long-Bone and Pelvic Fractures, Injury, Mar. 2007, pp. 318-328.

MacKenzie, I.M.J., The Haemodynamics of Human Septic Shock, Anaesthesia, 2001, vol. 56, pp. 130-144.
MacLean, Lloyd et al., Patterns of Septic Shock in Man—A Detailed Study of 56 Patients, Annals of Surgery, Oct. 1967, vol. 166, No. 4, pp. 543-558.
Marik, Paul et al., The definition of septic shock: implications for treatment, Critical Care and Resuscitation, Mar. 2007, vol. 9, No. 1, Mar. 2007, pp. 101-103.
Marik, Paul, Surviving sepsis: going beyond the guidelines, Annals of Intensive Care, Jun. 7, 2011, 1:17, 6 pages.
Opal, Steven, The Uncertain Value of the Definition for SIRS, Editorial downloaded from www.journal.publications.chestnet.org/ on Nov. 19, 2013, pp. 1442-1443.
Peres Bota, Daliana et al., Infection Probability Score (IPS): A method to help asses the probability of infection in critically ill patients, Crit Care Med, 2003, vol. 31, No. 11, pp. 2579-2584.
Rangel-Frausto MD, M. Sigfrido, The Natural History of the Systemic Inflammatory Response Syndrome (SIRS), JAMA, Jan. 11, 1995, vol. 273, No. 2, pp. 117-123.
Rivers, Emanuel et al., Early Goal-Directed Therapy in the Treatment of Severe Sepsis and Septic Shock, The New England Journal of Medicine, Nov. 8, 2001, vol. 345, No. 19, pp. 1368-1377.
Shoemaker, WC et al., Hemodynamic and Oxygen Transport Monitoring to Titrate Therapy in Septic Shock, New Horiz., Feb. 1993, pp. 145-159, vol. 1, No. 1 (Abstract).
Shoemaker, WC et al., Invasive and Noninvasive Haemodynamic Monitoring of Acutely Ill Sepsis and Septic Shock Patients in the Emergency Department, Eur J Emerg Med, Sep. 2000, pp. 169-175, vol. 7, No. 3.
Shoemaker, WC et al., Pathophysiology of Adult Respiratory Distress Syndrome After Sepsis and Surgical Operations, Crit Care Med., Mar. 1985, pp. 166-172, vol. 13, No. 3 (Abstract).
Shoemaker, WC et al., Role of Oxygen Debt in the Development of Organ Failure Sepsis, and Death in High-Risk Surgical Patients, CHEST, Jul. 1992, pp. 208-215, vol. 102, No. 1.
Shoemaker, WC et al., Sequence of Physiologic Patterns in Surgical Septic Shock, Crit Care Med, Dec. 1993, pp. 1876-1889, vol. 21, No. 12.
Shoemaker, WC et al., Use of Sequential Physiologic Measurements for Evaluation and Therapy of Uncomplicated Septic Shock, Surgery, Gynecology & Obstetrics, Aug. 1970, pp. 245-254.
Shoemaker, WC, Cardiorespiratory Patterns in Complicated and Uncomplicated Septic Shock: Physiologic Alterations and Their Therapeutic Implications, Ann. Surg., Jul. 1971, pp. 119-125, vol. 174, No. 1.
Shoemaker, WC, Circulatory Mechanisms of Shock and Their Mediators, Crit Care Med., Aug. 1987, pp. 787-794, vol. 15, No. 8 (Abstract).
Shoemaker, WC, Temporal Hemodynamic and Oxygen Transport Patterns in Medical Patients, CHEST, Nov. 1993, pp. 1529-1536, vol. 104, No. 5.
Shoemaker, WC, Temporal Physiologic Patterns of Shock and Circulatory Dysfunction Based on Early Descriptions by Invasive and Noninvasive Monitoring, New Horiz., May 1996, pp. 300-318, vol. 4, No. 2 (Abstract).
Shoemaker, William et al., Role of Physiologic Monitoring in the Intensive Care Unit, Surgery Annual, 1970, pp. 61-81.
Shoemaker, William, Pathophysiologic Basis of Therapy for Shock and Trauma Syndromes: Use of Sequential Cardiorespiratory Measurements to Describe Natural Histories and Evaluate Possible Mechanisms, Seminars in Drug Treatment, Winter 1973, vol. 3, No. 3, pp. 211-229.
Shoemaker, William, Physiologic Mechanisms in Clinical Shock, Adv Exp Med Biol, Oct. 23, 1971, pp. 57-75.
Shoemaker, William, Sequential Hemodynamic Patterns in Various Causes of Shock, Surgery, Gynecology & Obstetrics, Mar. 1971, pp. 411-423.
Simmons, Daniel et al., Hyperventilation and Respiratory Alkalosis as Signs of Gram-Negative Bacteremia, JAMA, Dec. 31, 1960, vol. 174, No. 18, pp. 2196-2199.
Simmons, Richard, The Role of Central Nervous System in Septic Shock, Annals of Surgery, Feb. 1968, vol. 167, No. 2, pp. 158-167.

(56) References Cited

OTHER PUBLICATIONS

Sun, Dong et al., The Natural History of the Systemic Inflammatory Response Syndrome and the Evaluation of SIRS Criteria as a Predictor of Severity in Patients Hospitalized through Emergency Services, 1999, vol. 48, No. 1; pp. 28-37.
Velmahos, George et al., Endpoints of Resuscitation of Critically Injured Patients: Normal or Supranormal?, Annals of Surgery, 2000, pp. 409-418, vol. 232, No. 3.
Author Unknown, $FiO_2$, Wikipedia Encyclopedia, modified Oct. 30, 2007 . . . http://en.wikipedia.org/wiki/FiO2.
Author Unknown, Hospital Inpatient Chart, Publication information unknown, Undated.
Avance Innovating with you, shaping exceptional care, Brochure, GE Healthcare, pp. 8.
Centiva/5 Critical Care Ventilator, Brochure, GE Healthcare, pp. 8.
Cirignotta, Fabio, Cerebral Anoxic Attacks in Sleep Apnea Syndrome, Sleep, 1989, pp. 400-404, vol. 12 No. 5.
Critical Care Therapy and Respiratory Care Section Policy, National Institute of Health, pp. 7.
Curry, J. Paul, Threshold Monitoring, Alarm Fatigue, and the Patterns of Unexpected Hospital Death, APSF Newsletter, Fall 2011, pp. 32-35.
Datex-Phmeda Output Protocols Ohmeda Corn 1.0 Serial Protocol, Brochure, Datex-Ohmeda, Version 1.5, pp. 31.
Davidson Ward, Sally et al., Responses to hypoxia and hypercapnia in infants of substance-abusing mothers, The Journal of Pediatrics, 1992, pp. 704-709, vol. 121 No. 5 Pt. 1.
Diagnostic Apparatus, Bibliographic Data: JP63275325A, Publication Date Nov. 14, 1988, 12 pages.
Horne, Rosemary S.C. et al., Arousal responses and risk factors for sudden infant death syndrome, Sleep Medicine 3, 2002, Supplement, pp. S61-S65.
Horne, Rosemary S.C. et al., Effects of Prematurity on Arousal from Sleep in the Newborn Infant, Pediatric Research, 2000, pp. 468-474, vol. 47 No. 4.
Intensive Care Ventilators, Product Comparison by Healthcare Product Comparison Systems, Inc. published by ECRI, Apr. 2006, 71 pages.
International Application No. PCT/US2009/059102, Written Opinion of the International Searching Authority, dated Apr. 5, 2011.
Litvak, Eugene et al., "Rethinking Rapid Response Teams," JAMA, 2010, vol. 304(12), pp. 1375-1376.
Lung Volumes, Wikipedia, available at http://en.wikipedia.org/wiki/Tidal_volume, printed on Nov. 15, 2007, 4 pages.
Maddox, Ray et al., "Clinical Experience with Patient-Controlled Analgesia Using Continuous Respiratory Monitoring and a Smart Infusion System," Am. J. Health-Syst. Pharm., 2006, vol. 63, pp. 157-164.
McEwen, James et al., Detection of Interruptions in the Breathing Gas of Ventilated Anaesthetized Patients, Canadian Journal of Anaesthology, 1988, vol. 35, No. 6, pp. 549-561.
McKinney, "Alarm fatigue sets off bells, Mass. incident highlights need for protocols check," Modern Healthcare, 2010, vol. 40(15), pp. 14.
Moldenhauer, Kendra et al., "Clinical triggers: an alternative to a rapid response team," 2009, vol. 35(3), pp. 164-174.
Moses, James et al., "The correlation and level of agreement between end-tidal and blood gas $pCO_2$ in children with respiratory distress: a retrospective analysis," BMC Pediatrics, 2009, vol. 9(20), 6 pages.
Newman, N.M., Arousal defect: Mechanism of the Suddent Infant Death Syndrome?, Australian Pediatric Journal, 1989, pp. 196-201.
Nguyen, H. Bryant, et al, Severe Sepsis and Septic Shock: Review of the Literature and Emergency Department Management Guidelines, Annals of Emergency Medicine, Jul. 2006, vol. 48, No. 1, pp. 28-55.
Ochroch, Andrew et al., "The impact of continuous pulse oximetry monitoring on intensive care unit admissions from a postsurgical care floor," Anesth Analg, 2006, vol. 1 02(3), pp. 868-875.
Pae, Eung-Kwon et al., Neuroscience Letters 375, 2005, pp. 123-128.
Redline et al., "The Scoring of Respiratory Events in Sleep: Reliability and Validity," Journal of Clinical Sleep Medicine, 2007, vol. 3(2), pp. 169-200.
Rivera, Luis, MD et al., Dynamic Ventilatory Characteristics During Weaning in Postoperative Critically Ill Patients, Anesthesia & Analgesia, 1997, vol. 84, pp. 1250-1255.
Saper, Clifford et al., "The Sleep Switch: Hypothalamic Control of Sleep and Wakefulness," Trends in Neurosciences, 2001, vol. 24(12), pp. 726-731.
Shelley, Kirk, "Photoplethysmography: Beyond the Calculation of Arterial Oxygen Saturation and Heart Rate," The International Anesthesia Research Society, 2010, 30 pages.
Sieker, Herbert et al., "Carbon dioxide intoxication: the clinical syndrome, its etiology and management with particular reference to the use of mechanical respirators," Medicine, 1956, vol. 35(4), pp. 389-423.
Simmons, Daniel et al., "Hyperventilation and respiratory alkalosis as signs of gram-negative bacteremia," JAMA, 1960, vol. 174(18), pp. 2196-2199.
Smith, Gary et al., "Review and performance evaluation of aggregate weighted 'track and trigger' systems," Resuscitation, 2008, vol. 77, pp. 170-179.
Stock, Christine et al., "The $PaCO_2$ rate of rise in anesthetized patients with airway obstruction," J. Clin. Anesth., 1989, vol. 1(5), pp. 328-332.
Taenzer, Andreas et al., "Impact of pulse oximetry surveillance on rescue events and intensive care unit transfers: a before-and-after concurrence study," Anesthesiology, 2010, vol. 112(2), pp. 282-287.
Tufte, Edward R., The Visual Display of Quantitative Information (Graphics Press, 1983), p. 17, 21, 153.
Van Lieshout, Johannes et al., "Physical manoeuvres for combating orthostatic dizziness in autonomic failure," The Lancet, 1992, vol. 339, pp. 897-898.
White, David, "Opioid-induced suppression of genioglossal muscle activity: is it clinically important?" J. Physiol., 2009, vol. 587, pp. 3421-3422.
Wiedemann et al., The effect of sedation on pulmonary function Anaesthesist, 1995, vol. 44 Suppl 3, pp. S588-S593 (Abstract only).
Younes, Magdy, "Contributions of Upper Airway Mechanics and Control Mechanisms to Severity of Obstructive apnea," Am. J. Respir. Crit. Care Med., 2003, vol. 168, pp. 645-658.
Appeal Brief for U.S. Appl. No. 11/351,961, filed Sep. 24, 2009.
Caines et al: "Overlooking orthostatic hypotension with routine blood-pressure equipment" 1 Lancet the Lancet Limited. London, GB, vol. 352, No. 9126, Aug. 8, 1998 (Aug. 8, 1998), p. 458, DXP004832973, ISSN:0140-6736, the whole document.
Capuano, Terry Ann, et al., Remote Telemetry, Nursing Management, Vo. 26, No. 7, Jul. 1995, p. 26.
Diep, Binh An, et al., Polymorphonuclear leukocytes mediate *Staphylococcus aureus* Panton-Valentine leukocidin-induced lung inflammation and injury, PNAS, Mar. 23, 2010, vol. 107, No. 12, pp. 5587-5592.
Doctors use 'remote control' to monitor ICU patients, CNN.com. technology>computing, Aug. 21, 2000, http://www.cnn .com/2000/TEC H/computing/08/21/icu. t_t 1.
Earthrowl-Gould, T., et al.; "Chest and abdominal surface motion measurement for continuous monitoring of respiratory function," Proc. lnstn Mech Engrs, V215, Part H; pp. 515-520 (2001).
East, Christine E., et al.; "Fetal Oxygen Saturation and Uterine Contractions During Labor," American Journal of Perinatology, vol. 15, No. 6, pp. 345-349 (Jun. 1998).
Examiner's Answer for U.S. Appl. No. 11/351,961, dated Jan. 4, 2010.
Ferrari, A U, et al., Inverse Relationship between heart rate and blood pressure variabilities in rats. Hypertension. Nov. 1987, vol. 10, No. 5, pp. 533-537.
Final Office Action for U.S. Appl. No. 11/351,961, dated Apr. 24, 2009.
Finding Value in Intensive Care, From Afar, The New York Times on the Web, Jul. 27, 1999, www.Visicu.com/ companynews/0799_nytimes.htm.

(56) References Cited

OTHER PUBLICATIONS

Grundy, Betty L., et al., Telemedicine in Critical Care: An Experiment in Health Care Delivery, JACEP, vol. 6, Oct. 1977, pp. 439-444.

International Search Report and Written Opinion for application No. PCT/GB2010/001624 dated Dec. 7, 2010.

International Search Report, PCT/US2008/002253; dated Jun. 9, 2008.

International Search Report, PCT/US2008/002254, dated Jul. 28, 2008.

Johansson, A.; "Neural network for photoplethysmographic respiratory rate monitoring," Medical & Biological Engineering & Computing, vol. 41, pp. 242-248 (2003).

Johnston, W.S., et al.; "Extracting Breathing Rate information from a Wearable Reflectance Pulse Oximeter Sensor," Proceedings of the 26th Annual International conference of the IEEE EMBS, San Francisco, California; Sep. 1-5, 2004; pp. 5388-5391.

Kaplan, Simon M. and Geraldine Fitzpatrick, Designing Support for Remote Intensive-Care Telehealth Using the Locales Framework, ACM, 1997, pp. 173-184.

Lee, Ho Sung, et al., Remote Patient Monitoring Service through World-Wide Web, Proceedings—19th International Conference—IEEE/EMBS, Oct. 3D-Nov. 2, 1997, pp. 928-931.

Levy, Mitchell M., et al., 2001 SCCM/ESICM/ACCP/ATS/SIS International Sepsis Definitions Conference, Critical Care Medicine, 2003, pp. 1250-1256, vol. 31 No. 4.

Mabry, Susan L., et al., Integrated Medical Analysis System, Proceedings of the 1997 Winter Simulation Conference, , 1997, pp. 1167-1168.

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Members of the American College of Chest Physicians/Society of Critical Care Medicine Consensus Conference Committee, Definitions for sepsis and organ failure and guidelines for the use of innovative therapies in sepsis, Critical Care Medicine, 1992, pp. 864-874, vol. 20 No. 6.

Miksch, Silvia, Artificial Intelligence for Decision Support: Needs, Possibilities, and Limitations in ICU, 10th Postgraduate Course in Critical Care Medicine A.P.I.C.E. '95, Springer, 1995, pp. 1-11.

Nenov, Valeriy and John Klopp, Remote Access to Neurosurgical CU Physiological Data using the World Wide web, health Care in the Information Age, 1996, pp. 242-249.

Netzer, Nikolaus et al., Overnight Pulse Oximetry for Sleep-Disordered Breathing in Adults, A Review, Chest, vol. 120, #2, Aug. 2001, pp. 625-633, Northbrook, IL, USA.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Non-Final Office Action for U.S. Appl. No. 11/351,961, dated Aug. 19, 2008.

Notice of Allowability for U.S. Appl. No. 10/150,582, dated Feb. 13, 2006.

Notice of Allowance for U.S. Appl. No. 11/455,408, dated Jan. 23, 2012 8 pages.

Notice of Allowance for U.S. Appl. No. 11/455,488, dated Aug. 22, 2011 8 pages.

Notice of Allowance for U.S. Appl. No. 11/455,488, dated Nov. 29, 2011 8 pages.

Official Action for Canada Patent Application No. 2,678, 776, dated Feb. 8, 2012.

Official Action for Canada Patent Application No. 2,678,856, dated Feb. 2, 2012 3 pages.

Official Action for U.S. Appl. No. 10/150,582, dated Jun. 20, 2005.

Official Action for U.S. Appl. No. 11/274,960, dated Jun. 8, 2010.

Official Action for U.S. Appl. No. 11/274,960, dated Oct. 20, 2010.

Official Action for U.S. Appl. No. 11/280,559, dated Mar. 21, 2011 13 pages.

Official Action for U.S. Appl. No. 11/280,559, dated Oct. 5, 2011 12 pages.

Official Action for U.S. Appl. No. 11/280,653, dated Dec. 1, 2010 9 pages.

Official Action for U.S. Appl. No. 11/280,653, dated Jun. 13, 2011 8 pages.

Official Action for U.S. Appl. No. 11/280,653, dated Mar. 31, 2010.

Official Action for U.S. Appl. No. 11/351,787, dated Apr. 22, 2011 11 pages.

Official Action for U.S. Appl. No. 11/351,787, dated Nov. 12, 2010.

Official Action for U.S. Appl. No. 11/351,961, dated Apr. 24, 2009.

Official Action for U.S. Appl. No. 11/351,961, dated Aug. 19, 2008.

Official Action for U.S. Appl. No. 11/351,961, dated Jan. 4, 2010.

Official Action for U.S. Appl. No. 11/369,355, dated Aug. 18, 2011 8 pages Restriction Requirement.

Official Action for U.S. Appl. No. 11/369,355, dated Jan. 6, 2012 8 pages.

Official Action for U.S. Appl. No. 11/369,379, dated Jun. 20, 2011 8 pages.

Official Action for U.S. Appl. No. 11/455,408, dated Dec. 27, 2010.

Official Action for U.S. Appl. No. 11/455,408, dated Jul. 27, 2011 6 pages.

Official Action for U.S. Appl. No. 11/455,488, dated Dec. 28, 2010.

Official Action for U.S. Appl. No. 12/437,385, dated Apr. 5, 2011 22 pages.

Official Action for U.S. Appl. No. 12/437,385, dated Nov. 25, 2011 18 pages.

Official Action for U.S. Appl. No. 12/839,177, dated Nov. 21, 2011 12 pages.

Perednia, Douglas A., Telemedine Technology and Clinical Applications, JAMA, vol. 6, Feb. 8, 1995, p. 483.

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

Remote Monitoring of ICU Patients Lowers Mortality Rates, Complications, Johns Hopkins Newsrelease, Mar. 20, 2001, http://www.newswise. com/articles/2001/3/ICU.JHM.html.

Response to Non-Final Office Action for U.S. Appl. No. 11/351,961, filed Dec. 19, 2008.

Restriction Requirement for U.S. Appl. No. 11/369,355, dated Sep. 2, 2010.

Restriction Requirement for U.S. Appl. No. 11/274,960, dated Feb. 3, 2010.

Restriction Requirement for U.S. Appl. No. 11/280,559, dated Mar. 4, 2010.

Restriction Requirement for U.S. Appl. No. 11/280,559, dated Oct. 18, 2010.

Restriction Requirement for U.S. Appl. No. 11/455,408, dated Sep. 30, 2010.

Restriction Requirement for U.S. Appl. No. 11/455,488, dated Sep. 16, 2010.

Restriction Requirement for U.S. Appl. No. 11/351,787, dated Jul. 9, 2010.

Restriction Requirement for U.S. Appl. No. 11/369,355, dated Dec. 8, 2010.

Restriction Requirement for U.S. Appl. No. 11/369,379, dated Dec. 27, 2010.

Restriction Requirement for U.S. Appl. No. 11/369,379, dated Sep. 20, 2010.

Rosenfeld, M.D., Brian A., FCCM, FCCP, et al., Intensive care unit telemedicine: Alternate paradigm for providing continuous intensive care, Critical Care Medicine, vol. 28, No. 12, 2000 p. 3925.

Seelbach-Gobel, Birgit, et al.; The prediction of fetal acidosis by means of intrapartum fetal pulse oximetry, Am J. Obstet. Gynecol., vol. 180, No. 1, Part 1, pp. 73-81 (1999).

Seigel, Todd A., et al., Inadequacy of Temperature and White Blood Cell Count in Predicting Bacteremia in Patients D with Suspected Infection, 2010, Elsevier, Inc., The Journal of Emergency Medicine, pp. 1-6, 2010.

Spigulis, Janis, et al.; "Optical multi-channel sensing of skin blood pulsations," Optical Sensing, Proceedings of SPIE, vol. 5459, pp. 46-53 (2004).

(56) References Cited

OTHER PUBLICATIONS

U.S. Appl. No. 11/431,686, Amendment and Response to NF Office Action, filed Jun. 21, 2011.
U.S. Appl. No. 11/431,686, Final Office Action, dated Oct. 12, 2011.
U.S. Appl. No. 11/431,686, NF Office Action, dated Jan. 21, 2011.
U.S. Appl. No. 11/431,686, Office Action (Restriction Requirement), dated Sep. 30, 2010.
U.S. Appl. No. 11/431,686, Request for Continued Examination and Preliminary Amendment, filed Feb. 29, 2012.
U.S. Appl. No. 11/431,686, Response to Restriction Requirement, filed Oct. 29, 2010.
U.S. Appl. No. 11/431,686, U.S. Appl. No. 11/431,686, NF Office Action, dated Jan. 21, 2011.
U.S. Appl. No. 12/437,385, Amendment and Response to NF Office Action, dated Jan. 15, 2013.
U.S. Appl. No. 12/437,385, Amendment and Response to NF Office Action, dated Sep. 6, 2011.
U.S. Appl. No. 12/437,385, Final Office Action, dated Nov. 25, 2011.
U.S. Appl. No. 12/437,385, NF Office Action, dated Apr. 5, 2011.
U.S. Appl. No. 12/437,385, NF Office Action, dated Aug. 17, 2012.
U.S. Appl. No. 12/437,385, Request for Continued Examination and Preliminary Amendment, filed Feb. 7, 2012.
U.S. Appl. No. 12/437,417, Amendment and Response to NF Office Action, dated Nov. 5, 2012.
U.S. Appl. No. 12/437,417, Amendment and Response to NF Office Action, dated Sep. 6, 2011, 13 pages.
U.S. Appl. No. 12/437,417, Final Office Action, dated Feb. 14, 2013.
U.S. Appl. No. 12/437,417, NF Office Action, dated Aug. 3, 2012.
U.S. Appl. No. 12/437,417, Request for Continued Examination and Preliminary Amendment, filed Feb. 29, 2012.
U.S. Appl. No. 12/629,407, Amendment and Response to NF Office Action dated Sep. 25, 2012, filed Feb. 21, 2013.
U.S. Appl. No. 12/629,407, NF Office Action, dated Aug. 16, 2012.
U.S. Appl. No. 12/629,407, NF Office Action, dated Sep. 25, 2012.
U.S. Appl. No. 12/629,407, Response to Requirement for Restriction, filed Sep. 14, 2012.
Yoon, Gilwon, et al.; Multiple diagnosis based on Photoplethysmography: hematocrit, Sp02, pulse and respiration, Optics in Health Care and Biomedical optics: Diagnostics and Treatment; Proceedings of the SPIE, vol. 4916; pp. 185-188 (2002).
Campbell, Beverly, Arterial Waveforms: Monitoring Changes in Configuration, Hemodynamics, Heart & Lung, May/Jun. 1997, vol. 26, No. 3, pp. 204-214.
Alaris System, Brochure, Medication Safety System Focused at the Point of Care, Cardinal Health, Alaris Products, pp. 8, 2004.
Alian, Aymen et al., Evaluation of Rapid Response Team Flag-Alert Parameters, Published on www.cardiopulmonarycorp.com/pdf/rapidresponsealert paramers.pdf referenced in 2008, Internet Publication 2010.
Author Unknown, Chapter IV Oxygen Consumption During ADO, Introduction, pp. 40-46, Book Title Unknown, Study published 1980.
Author Unknown, Chapter X Effects of a 6-minute Period of ADO, Introduction, pp. 108-113, Book Title Unknown, Study published 1980.
Author Unknown, Hospital Inpatient Chart, Completed prior to 2011, not published.
Avance Innovating with you, shaping exceptional care, Brochure, GE Healthcare, pp. 8, 2006.
Bartolo, Anton et al., An Arrhythmia Detector and Heart Rate Estimator for Overnight Polysomnography Studies, conditionally accepted for IEEE Transactions, 19 pages, Nov. 3, 2000.
Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company I Sleep Apnea and Narcotic Postoperative Paln . . . http://www.thedoctors.com/risk/bulletins/sleepapnea.asp, 2002: 17:39.
Buckle, Patricia et al., Polysomnography in Acutely Ill Intensive Care Unit Patients, Chest, v. 102 n.1, p. 288 (4), American College of Chest Physicians, Jul. 1992.
Centiva/5 Critical Care Ventilator, Brochure, GE Healthcare, pp. 8, Oct. 2005.
CHI, Time-Series Matrices, University of Minnesota, http://www-users.cs.umn.edu/-echi/papers/infovis97/spread/node13.html, 1997, pp. 1-3.
Critical Care Therapy and Respiratory Care Section Policy, National Institute of Health, pp. 7, revised Mar. 2000.
Daley, Denise M., MD, Beware of All Sedatives in Patients With Sleep Apnea, Anesthesia Patient Safety Foundation Newsletter and posted on the Malpractice company's web site. The Doctors Company, Sleep Apnea and Narcotic Postoperative Pain . . . http://www.thedoctors.com/risk/bulletins/sleepapnea.asp, Letters to the Editor 2002-2003.
Datex-Phmeda Output Protocols Ohmeda Corn 1.0 Serial Protocol, Brochure, Datex-Ohmeda, Version 1.5, pp. 31. Aug. 14, 2001.
Dempsey, Jerome A. et al., Sleep and Breathing State of the Art Review Sleep-Induced Breathing Instability, Sleep, vol. 19, No. 3, pp. 236-247, American Sleep Disorders Association and Sleep Research Society, 1996.
Ferber, Richard et al., Portable Recording in the Assessment of Obstructive Sleep Apnea, ASDA Standards of Practice, American Sleep Disorders Association, vol. 17, No. 4, pp. 378-392, 1610 14th Street, NW, Suite 300, Rochester, MN 55901-2200, USA, 1994.
Fisher, Kyle S., MD, Value of Pulse Oximetry Monitoring on the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp, Fall 2002.
Henderson, L. J. et al., Blood as a Physicochemical System. II, pp. 426-431, Paper, 1924.
Jain, Sanjay S. et al., Perioperative Treatment of Patients with Obstructive Sleep Apnea, Current Opinion Pulmonary Medicine 10, pp. 482-488, 2004.
Kaplan, Joseph et al., Home Pulse Oximetry as a Screening Test for Sleep-Disordered Breathing, Chest, vol. 103, pp. 322S, Northbrook, IL, USA, 1993.
Lynn, Lawrence, Background of Oximetry Utilization for Sleep Apnea Diagnosis, Publication information unknown, Article Written 1994, Not published.
Lynn, Lawrence A. et al., History of Threshold Oximetry, First viewing of Article Apr. 11, 2009, Not published.
Lynn, Lawrence A. et al., Piercing the Panacea of Pulse Oximetry, Article Written Jul. 24, 2006, 8 pages, Not published.
Lynn, Lawrence, The Physiologic Parameters Defining the Oximetry Waveform Patterns in Sleep Apnea, Article Written 1994, Not published.
Lynn, Lawrence et al., Patterns of Unexpected In-Hospital Deaths: A Root Cause Analysis, Patient Safety in Surgery, vol. 5, No. 3, pp. 1-25, Feb. 11, 2011.
Final Official Action for U.S. Appl. No. 12/629,407, dated Jul. 17, 2013 14 pages.
Final Office Action for U.S. Appl. No. 13/603,659, dated Sep. 25, 2013, 8 pages, English.
Non-Final Official Action for U.S. Appl. No. 11/369,355, dated Sep. 17, 2013 8 pages, English.
Patil, Ramesh S. et al., Application of an Artificial Intelligence Program to Therapy of High Risk Surgical Patients, New Horizons, vol. 4, No. 4, pp. 541-550, 1996.
Redline, Susan et al., Hypopnea, a Floating Metric: Implications for Prevalence, Morbidity Estimates, and Case Finding, Sleep, vol. 20, No. 12, pp. 1209-1217, 1997.
Ruchala, Joanna B., Chapter 13, Applications of Pulse Oximetry, Book: Design of Pulse Oximeters, pp. 214-236, Oct. 1997.
Sadeh, Avi et al., The Role of Actigraphy in the Evaluation of Sleep Disorders, An American Sleep Disorders Association and Sleep Research Society, Sleep, vol. 18, No. 4, pp. 288-302, 1995.
Scharf, Steven M. et al., Cardiovascular Effects of Periodic Occlusions of the Upper Airways in Dogs, American Review of Respiratory Disease, pp. 321-329, Aug. 1992.

(56) References Cited

OTHER PUBLICATIONS

Shneerson J, Obstructive Sleep Apnoea, BMJ, pp. 315-367 (Aug. 9, 1997); http://bmLcom/Shneerson et al. (7104).
Siggaard-Anderson, O et al., Editorial: The Bohr Effect and the Haldane Effect, Publication information unknown, 1973.
Strohl, Kingman P. et al., Physiologic Basis of Therapy for Sleep Apnea, State of Art: Physiologic Basis of Therapy for Sleep Apnea, pp. 791-802, 1986.
Tatevossian, Raymond G. et al. Noninvasive Hemodynamic Monitoring for Early Warning of Adult Respiratory Distress Syndrome in Trama Patients, Journal of Critical Care, vol. 15, No. 4 Dec. 2000, pp. 151-159.
Thorpy, Michael et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377, 1994.
Wilkins, Robert L. et al., EGAN's Fundamentals of Respiratory Care, Analysis and Monitoring of Gas Exchange, Book, Eighth Edition, Chapter 16, Section III, Capnography/Capnometry During Mechanical Ventilation, pp. 383-389, 2003.
Williams et al., Screening for Sleep Apnea Using Pulse Oximetry and a Clinical Score, Chest, 100/3, Sep. 1991, pp. 631-635.
Herasevich et al., Designing and testing computer based screening engine for severe sepsis/septic shock, AMIA 2008 Symposium Proceedings, p. 864.
Herasevich et al., Enrollment into a time sensitive clinical study in the critical care setting: results from computerized septic shock sniffer implementation, J Am Med Inform Assoc. 2011, vol. 18, pp. 639-644.
Stenhouse C, Coates S, Tivey M, Allsop P, Parker T. Prospective evaluation of a Modified Early Warning Score to aid earlier detection of patients developing critical illness on a general surgical ward. State of the Art Meeting, Intensive Care Society, London, Dec. 1999.
Non-Final Office Action for U.S. Appl. No. 13/392,827, dated Mar. 27, 2015, 18 pages.
Non-Final Office Action for U.S. Appl. No. 13/677,295, dated Apr. 8, 2015, 15 pages.
Non-Final Office Action for U.S. Appl. No. 13/844,381, dated Apr. 9, 2015, 21 pages.
Non-Final Office Action for U.S. Appl. No. 13/844,212, dated Apr. 9, 2015, 21 pages.
Non-Final Office Action for U.S. Appl. No. 13/844,404, dated Apr. 9, 2015, 18 pages.
Final Office Action for U.S. Appl. No. 12/437,385, dated May 14, 2015, 31 pages.
Non-Final Office Action for U.S. Appl. No. 12/777,171, dated Mar. 5, 2015, 12 pages.
Non-Final Office Action for U.S. Appl. No. 14/193,757, dated May 8, 2015, 15 pages.
Non-Final Office Action for U.S. Appl. No. 14/193,829, dated May 22, 2015, 17 pages.
Fawcett, Tom, ROC Graphs: Notes and Practical Considerations for Data Mining Researchers, Hewlett-Packard Company, 2003, 28 pages.
Guven et al., Diagnostic Value of Procalcitonin Levels as an Early Indicator of Sepsis, Am JEmerg Med, 2002m pp. 202-206, vol. 20
Haumptman et al., Evaluation of the Sensitivity and Specificity of Diagnostic Criteria for Sepsis in Dogs, Veterinary Surgery, 1997, pp. 393-379, vol. 26
International Search Report for International (PCT) Patent Application No. PCT/US2012/065124, dated Jul. 23, 2015, 6 pages
Rao, Singiresu, Engineering Optimization Theory: Advantages of Random Search Methods, 2009, pp. 314-317.
PCT—International Preliminary Report on Patentability, for PCT application No. PCT/US2014/019530; dated Sep. 1, 2015; 8 Pages.
PCT—International Preliminary Report on Patentability, for PCT application No. PCT/US2014/019556; dated Sep. 1, 2015; 9 Pages.
PCT—International Preliminary Report on Patentability, for PCT application No. PCT/US2014/019572; dated Sep. 1, 2015; 6 Pages.
PCT—International Preliminary Report on Patentability, for PCT application No. PCT/US2014/019577; dated Sep. 1, 2015; 8 Pages.
PCT—International Preliminary Report on Patentability, for PCT application No. PCT/US2014/019637; dated Sep. 1, 2015; 8 Pages.
PCT—International Preliminary Report on Patentability, for PCT application No. PCT/US2014/019442; dated Sep. 1, 2015; 6 Pages.
PCT—International Preliminary Report on Patentability, for PCT application No. PCT/US2014/019582; dated Sep. 1, 2015; 7 Pages.
PCT—International Preliminary Report on Patentability, for PCT application No. PCT/US2014/019587; dated Sep. 1, 2015; 6 Pages.
PCT—International Preliminary Report on Patentability, for PCT application No. PCT/US2014/019625; dated Sep. 1, 2015; 15 Pages.
Non-Final Office Action issued in U.S. Appl. No. 12/629,407, dated Oct. 2, 2015, 19 Pages.
Dec. 20, 2016 U.S. Final Office Action—U.S. Appl. No. 14/528,645.
Graham, et al., "Monitor Alarm Fatigue: Standardzing Use of Physiological Monitors and Decreasing Nuisance Alarms," American Journal of Critical Care, Jan. 2010, vol. 19, No. 1, pp. 28-35.
Claise, Brian, "Alarm Fatigue and Its Management Have Become Serious Healthcare Safety Issues," Critical response Systems, Inc., 2011-2014, Document 14-077, Version 1.1, pp. 1-4.
Sendelbach, et al., "Alarm Fatigue—A Patient Safety Concern," AACN Advanced Critical Care, vol. 24, No. 4, pp. 378-386.
Sep. 21, 2016—U.S. Final Office Action—U.S. Appl. No. 12/437,385.
Richard J. Allen and Timothy C. Elston; "From Physics to Pharmacology?"; Department of Pharmacology, University of North Carolina at Chapel Hill, Chapel Hill, NC, US; Reports on Progress on Physics; Institute of Physics Publishing; vol. 74, No. 1; Dec. 3, 2010; pp. 1-19; stacks.iop.org/RoPP/74/016601.
Sergey M. Zuev, et al.; "Sepsis Progression and Outcome: A Dynamical Model"; Theoretical Biology and Medical Modelling, Biomed Central, Ltd.; London, GB; vol. 3, No. 1; Feb. 15, 2006; pp. 1-15; http://tbiomed.com/content/3/1/8.

* cited by examiner

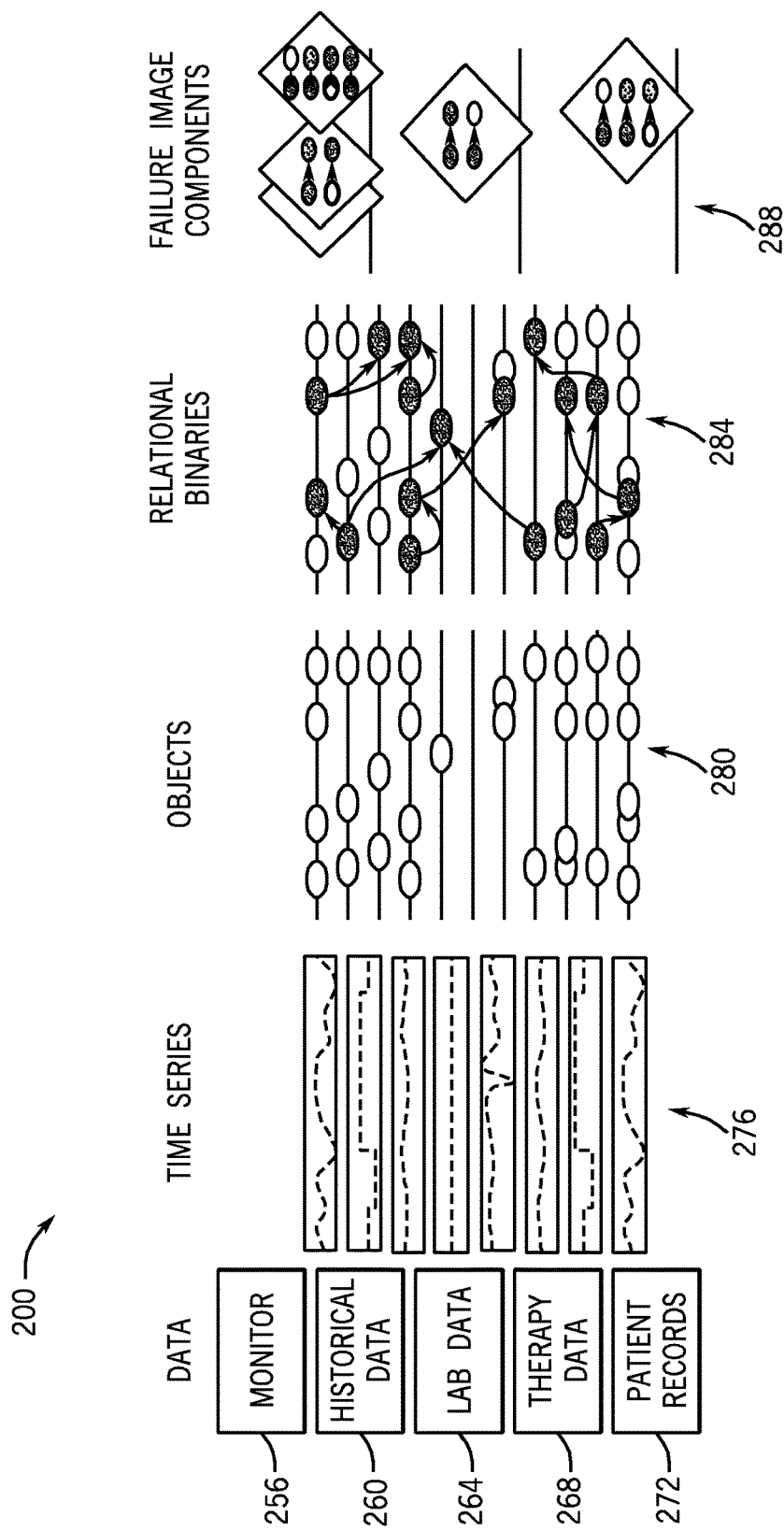

MEDICAL FAILURE PATTERN SEARCH ENGINE

CROSS-REFERENCE TO RELATED APPLICATIONS

This application is a continuation of U.S. patent application Ser. No. 12/437,385, which claims the benefit of U.S. Provisional Application No. 61/126,906, filed May 8, 2008 and to U.S. Provisional Application No. 61/200,162, filed Nov. 25, 2008, the disclosures of which are hereby incorporated by reference in their entirety for all purposes. This application is a continuation-in-part of U.S. patent application Ser. No. 12/437,417 filed May 7, 2009 entitled "Patient Safety Processor," the disclosure of which is hereby incorporated by reference in its entirety for all purposes. This application is also a continuation in part of U.S. patent application Ser. No. 12/629,407 entitled "Microprocessor System for the Analysis of Physiologic and Financial Datasets," filed Dec. 2, 2009 which is a continuation of U.S. patent application Ser. No. 10/150,842, entitled "Microprocessor System for the Analysis of Physiologic and Financial Datasets," filed May 17, 2002, now U.S. Pat. No. 7,758,503, the disclosure of which is hereby incorporated by reference in its entirety for all purposes, which claims the benefit of U.S. Provisional Application Ser. No. 60/291,687 filed May 17, 2001, the contents of which are hereby incorporated herein by reference and U.S. Provisional Application Ser. No. 60/291,691, filed on May 17, 2001. This application is also a continuation in part of U.S. patent application Ser. No. 11/369,355, entitled "Centralized hospital monitoring system for automatically detecting upper airway instability and for preventing and aborting adverse drug reactions", filed Mar. 7, 2006, which is a continuation of U.S. patent application Ser. No. 10/150,582 entitled "Centralized hospital monitoring system for automatically detecting upper airway instability and for preventing and aborting adverse drug reactions," filed May 17, 2002 now U.S. Pat. No. 7,081,095, which claims the benefit of U.S. Provisional Patent Application Ser. Nos. 60/291,691 and 60/291,687, both filed May 17, 2001 and U.S. Provisional Patent Application Ser. No. 60/295,484 filed Jun. 1, 2001, the disclosures and contents of which are incorporated by reference as if completely disclosed herein. This application is also a continuation-in-part and claims priority to U.S. patent application Ser. No. 12/152,747, entitled "Pulse Oximetry Relational Alarm System for Early Recognition of Instability and Catastrophic Occurrences," filed May 16, 2008, the disclosure of which is hereby incorporated by reference in its entirety and for all purposes.

BACKGROUND

The present disclosure relates systems and methods for detecting and monitoring patient conditions in clinical medicine settings.

Patients die unexpectedly on hospital wards under the careful watch of even knowledgeable and diligent healthcare workers at alarming rates. It has been argued that hospitals have a culture of failure tolerance. However, a more critical analysis reveals that this "tolerance" is actually resignation and that the high number of clinical failures comprises the unavoidable result of the ill-conceived attempt to manage the profound complexity of overlapping human pathophysiology without adequate technology. Unfortunately hundreds of common but subtle perturbations which combine to produce complex pathophysiologic failure cascades which progress to death can potentially occur with every patient in the hospital.

While the physiologic complexity of just one patient is often overwhelming, a single nurse may have twelve complex patients and a single hospitalist physician may have 30. In the present state of hospitals, most of the physiologic complexity resides in the electronic medical records (EMR) even as the patient progresses toward death. Unless an expert physician or nurse puts all the pieces together timely to see the evolving failure, the patient is often doomed even though healthcare workers are nearby.

Patient care in a hospital setting involves a complex management process because human pathophysiology is highly complex and healthcare workers address multiple patient issues simultaneously. Decisions about patient priority and care made by the healthcare workers are subjective to some degree and may vary depending on the level of expertise and experience of each person involved in patient care.

Because of the complexity involved in patient care, particularly in a hospital setting, healthcare workers have attempted to provide a level of uniformity to the process through protocol-based care. Such care may involve "if X-threshold-breach then Y-action" branching decision tree protocols. However, such protocols when considered in relation to the true level of pathophysiologic complexity often comprise a profound over simplification so that the healthcare worker can easily proceed down the wrong branch of a decision tree.

In addition to protocol-based care, healthcare workers often monitor various physiological parameters of a patient in order to obtain more information upon which they may base clinical care decisions. Many of these parameters may include blood oxygen levels, pulse rate, routine blood tests and vital sign tests, which may be recorded in a centralized electronic medical record. However, this testing may not be effective in the early detection of certain clinical conditions or in providing the healthcare worker with a clear picture of the patient's condition and care. Even subtle and minor levels of perturbation may lead to profound instability in certain clinical situations. For example, minor changes in the serum sodium in the setting of a stroke may lead to confusion and then obtundation, which may increase the risk of aspiration, pneumonia, and venous thrombosis. Indeed, the level of serum sodium decrement to produce such abnormalities may be as little as 8 mEq, a decrement which would otherwise not be likely to produce an adverse reaction in the absence of an acute stroke. Since an 8 mEq decline in serum sodium would normally be tolerated in the absence of a stroke, it may be easily overlooked as a cause of profound instability by a healthcare worker who may not be knowledgeable or diligent enough to recognize the entire relational complexity. It is very common that subtle or simple events or occurrences actually comprise linked components of a much larger, dangerous, but undetected expanding pathophysiologic failure process. Since simple pertubations are readily overlooked by the physician (or if they are identified, the pivotal linkage to other processes is commonly unrecognized), this allows the pathophysiologic failure process to progress, untreated toward death.

In another example of the challenges involved in the timely detection of evolving complex patient conditions, septic shock is often the end result of progression from the uncomplicated state of infection to progressive states of the inflammatory response syndrome, sepsis, severe sepsis, and finally septic shock. These distinctions of states are arbitrary and poorly defined at the bedside. The vast majority of patients have infection with fever without further progression and many even progresses to the inflammatory response syndrome without further progression to septic shock. Because routine blood testing and even continuous vital measurements may not always detect the pre-shock state, specialized blood tests and biomarker profiles specifically developed to detect the pre-septic shock state have been developed. However, specific blood test and profiles suffer from a lack of specificity, in part because the variable response of patients to physiologic perturbation. Whether or not a given patient progresses to shock depends on much more than the biomarkers present and their concentrations. Progression to shock may depend on a complex relationship of patient-specific physiologic responses to immunologic and inflammatory perturbation as well as the physiologic state of the patient at the onset and during the perturbation and the timeliness and adequacy of intervention (e.g. antibiotics and/or fluid). Since most of these factors are not captured by blood test measurements or biomarker profiles, even serial testing directed specifically toward the detection of the pre-shock state may not provide sufficient information to provide for reliable timely detection of the evolving state of severe sepsis or septic shock.

BRIEF DESCRIPTION OF THE DRAWINGS

Advantages of the present disclosure may become apparent upon reading the following detailed description and upon reference to the drawings in which:

FIG. 2 is a diagram depicting the levels of analysis in accordance with an exemplary embodiment;

DETAILED DESCRIPTION

Figure 1:
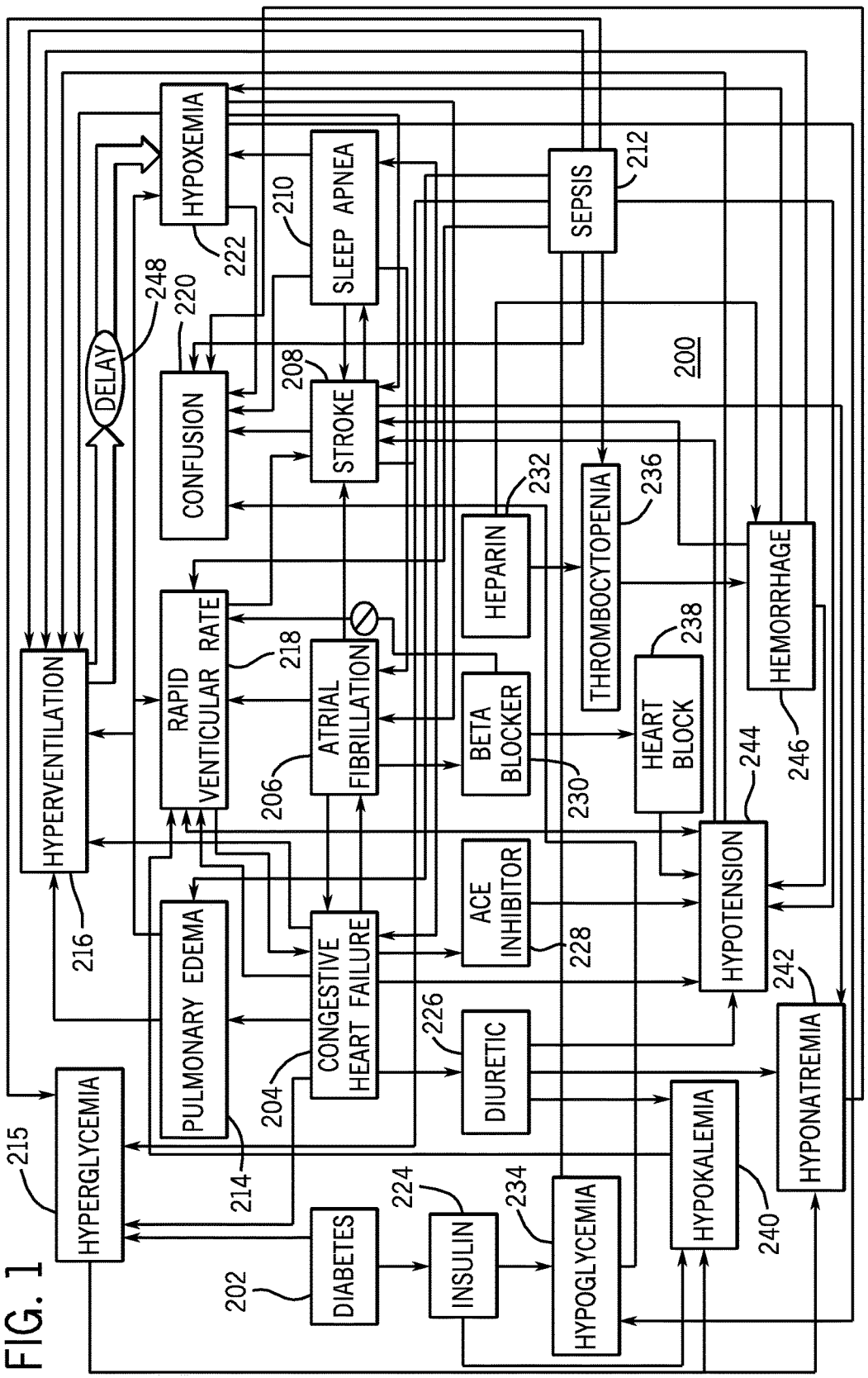
FIG. 1 is an exemplary component diagram of a patient demonstrating the overlapping patient complexities that may be used to construct relational binaries, image components and MPPC for searching and detection.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure provides systems and methods for diagnosis, monitoring, and treatment of certain clinical conditions.

One embodiment comprises a processor system including an electronic medical records database of a hospital or hospital system containing at least laboratory and physiologic data of at least one patient, a search engine programmed to automatically and repetitively search data within or derived from the database to detect complex patterns or images of evolving pathophysiologic cascades, and to further define the cascade, quantify the cascade, and to determine the relationships and cost of the cascade. According to one aspect of the invention a pathophysiologic cascade as detected by one embodiment comprises an expanding pathophysiologic process. Such expansion commonly occurs within the initially affected system as for example in the immune system (as an inflammation cascade) and then expands into other systems such as the respiratory and cardiovascular system often through chemical, neurological, and/or anatomical mechanisms of augmentation, up regulation, down regulation, compensation, compensation failure, and combined systems failure. The most important cascades detected by an embodiment of the present invention are cascades of evolving death (CED).

One embodiment comprises a search engine which automatically, intermittently and/or continuously searches for and detects pathophysiologic cascades and particularly cascades of evolving death (CED), and an alarm processor programmed to identify the patient which is generating the CED and to provide an alarm upon the detection of such a cascade at a site adjacent the location of the patient, to a care giver managing the patient, to a ward in which the patient resides, to a quality control center or patient safety management center, to the patient him or herself as by a pager or phone which may be configured to display an image of the cascade, the type of the cascade, and/or at least one characteristic of the cascade. The pager may generate a series of lights which are indicative of the severity of the failure and/or cascade detected. The wearing of the pager by the patient prevents the healthcare worker from discounting or ignoring the findings since the patient him or herself (or the patients family if the patient is not competent) is also notified by the processor.

According to one aspect of the present invention, cascades of evolving death (CED) are detected by the search engine as expanding aggregations of perturbations and variations of signals and/or tests derived from a biologic organism which spreads across signal and tests derived from different systems within the organism and commonly ends in death. Commonly, as the CED evolves, the number of perturbations, the number of different types of positive or negative trends or variations, and/or the number of different types of threshold breaches, and the number of perturbed systems, progressively rise.

One pathophysiologic process which commonly generates a widely expanded CED is severe sepsis. Severe sepsis commonly induces microcirculatory failure which eventually expands the CED across all systems dependent on microcirculation. In the lungs, evolving microcirculatory failure causes a progressive decline in the efficiency of gas exchange, minute ventilation rises to compensate or as a direct result of the factors (such as toxins) which are associated with the cause of the process. With many systems the response is biphasic, with an initial augmentation perturbation (with comprises a favorable or preparatory response of the system. As the cascade progresses, subsequent to augmentation, failure related perturbations develop expansively. In the sepsis CED example, metabolic system perturbation may initially be an augmentation perturbation comprising a simple preparatory fall in hydrogen ion, but later as the cascade evolves widespread failure related perturbations dominate.

Cascade of evolving death commonly contain smaller relational patterns which may progress virtually throughout the cascade and by themselves may portend death. For example the CED of severe sepsis contains the pattern of pathophysiologic divergence of ventilation and arterial oxygen saturation which is described in U.S. patent Ser. No. 10/150,842 (the disclosure of which is incorporated by reference as if completely disclosed herein). Despite the fact that such smaller relational patterns may progress virtually throughout the CED (and by themselves may portend death) these small patterns generally represent only a very small portion of the signal "bandwidth" of the death cascade, especially as the cascade matures and becomes widely expanded. The smaller relational patterns therefore are useful for detection of the likely presence of a CED but do not provide the specificity to determine the cause of the CED and may not be, especially early in their manifestation, specific for the presence of a CED.

Typical CED have at least one initiating apex or vertex which comprises the onset of the cascade. The apex or vertex is generally within a single physiologic system. The CED expands out from the apex or vertex across the initially affected system and/or into and across other systems. It is common for CED to expand within the initial system first. Like a progressively enlarging cone of perturbation projecting initially within and then beyond the initial system, the CED may expand to involve virtually all systems by the time the point of death is reached.

Cascades of evolving death, in 3D space can be represented by a cone with apex comprising the onset of the cascade, the length of the cone being defined by cascade duration, the angle of the come being defined by cascade expansion rate, and the cross-sectional area at a given point being defined by the magnitude of the cascade expansion at that point in time.

When, according to one embodiment of the present invention, the data sets are organized into a 2D format (such as a time series matrix which is compartmentalized such that each system defines a separate compartment of time series) the CED commonly produces a triangle with the angle at the vertex defining, in part, the speed of expansion of the CED. The CED, without intervention, will commonly end in death. In the 2D representation a death vertex is identified on the X axis and the triangle can be competed by passing a line vertically through all perturtubations or variations which remain at the time of death. This forms the base of the triangle of the CED.

If the patient achieves spontaneous or assisted recovery the cascade begins to contract. The point at which contraction begins forms the vertex and base of the cascade expansion triangle of the CED and the vertex and base of contraction triangle of the CED which eventually contracts to a stable state vertex point at the end of the contraction triangle. Even after a patient has recovered, the state of the physiologic components of the time series matrix of the stable state after the CED may be different from that which preceded the CED and this difference and its location in relation to systems and time series types is often a quantifiable indication of the extent and type of residual injury sustained by the patient due to the event which induced the CED, the CED itself, and/or due to treatment.

While the term cone and triangle is used herein for graphical representation of the expanding cascade, a preformatted matrix will be affected in a wide range of expanding patterns. Expansion may not be uniform or linear but rather the shape of the expanding cascade varies depending on a wide range of factors as will be discussed.

The processor may further be programmed to determine at least one of the type of cascade, the severity of the cascade, the duration of the cascade, the time of onset of the cascade, the maturity (as for example the stage) of the cascade. The severity may be determined by the number of perturbations or trends which comprise the cascade, the severity of the pertubations or trends (as for example by the slope and/or magnitude of the perturbations or trends which comprise the cascade in relation to the baseline values and/or statistical normal values by another severity measure), the number of systems affected by the cascade, the presence, number and/or severity of failure of compensation in response to perturbations associated with the cascade, the growth of the cascade, as for example by the number of new perturbations being added per unit time or the number of systems affected. The processor may also detect the events or components associated with or which are a part of the cascade. The alarm processor may be programmed to provide an indication of each of the forgoing. Alarm display may be provided for presenting any of the forgoing in textual, auditory, graphical, or other formats. The search may be reinitiated each time new data is added, each time a particular type of data is added, or at a preselected or adaptive frequency. For example the searching frequency may increase when early components of a possible cascade have been identified or when an actual cascade has been identified.

One embodiment retains the images and relationships detected during the previous search(s) so that the subsequent new search cycle of the data set is less processor intense involving, for example, only the comparison of the new data (with or without prior formatting) to the previous processed data sets to determine if a new cascade is developing, an existing cascade is becoming more severe or improving, or if another event in relation to a cascade (such as a treatment event) has occurred.

One embodiment comprises a patient data processing system for converting the global electronic medial record (EMR) of a patient or patients into a real-time patient monitor comprising a pathophysiologic cascade search engine configured to repetitively and/or continuously search the EMR for evolving complex pathophysiologic cascades and an alarm processor for outputting a warning upon detection of a cascade. The pathophysiologic failure cascade search engine may be programmed to continuously search the EMR for evolving complex images of physiologic failure such, for example a sepsis cascade, the alarm processor may be programmed to provide an alarm upon detection of the pathophysiologic failure cascade, and the image processor programmed to output an image of the evolving failure cascade. The data processing system may also be programmed to quantify the cascade, track the progression of the cascade, identify, highlight and/or alarm associated events in relation to the cascade, determine the cost associated with the cascade, determine the timing of treatment in relation to the cascade, and determine the response of the cascade in relation to treatment.

In another embodiment the processor is programmed to convert the electronic medical records into a particular format favorable for searching for pathophysiologic cascades. In one example such a format comprises sequential and timed trends comprised of at least positive trends and negative trends of both the physiologic parameters and the laboratory data, detect relational trends comprised of a combination of positive and/or negative trends, detect complex cascade patterns comprised of a plurality of combinations of relational trends, automatically output a display of the image of the detected complex cascade, automatically output a warning indicating the detection of the complex cascade, track the growth or decline of the complex cascade and output an indication indicative of growth or decline, the cascade pattern may be indicative of a single or multiple physiologic failures such as at least one of sepsis, severe sepsis, septic shock, and microcirculatory failure, a shock cascade, and a septic shock cascade to name a few. The processor may be programmed to determine and output an indication of the type of the cascade detected, to determine and output at least an indication of the timing and type of the trends along the cascade, to determine and output at least an indication of the length of the cascade, to detect the onset of therapy and to determine and output at least an indication of timing of therapy in relation to the cascade. The patient data processing system may comprise a computer be programmed to search the EMR to detect sequential and timed trends comprised of at least positive and negative trends of both the physiologic parameters and the laboratory data, determine relational timing of the detected positive and negative trends, detect complex cascade patterns comprised of a plurality of combinations of positive and negative trends evolving in sequential timed relation to each other, and output an indication of the detected complex relational cascade pattern.

In another embodiment, the processing system may comprising a computer programmed to convert the electronic medical records into sequential and timed trends comprised of at least positive trends and negative trends of both the physiologic parameters and the laboratory data, detect relational trends comprised of a combination of positive and/or negative trends, detect complex cascade patterns comprised of a plurality of combinations of relational trends, output an alarm indicating the detection of the complex cascade pattern.

Another embodiment comprises a patient data processing system for processing electronic medical records of at least physiologic parameters and laboratory data of at least one patient comprising a computer programmed to identify positive and negative trends comprising at least a combination of inflammatory trends, metabolic trends, hemodynamic trends, hematologic trends, and respiratory trends, identify the relational timing of the positive and negative which relationally or collectively are indicative of the septic shock or pre-septic shock failure cascade, and identify and output an indication of the septic shock or pre-septic shock failure cascade. The may be further programmed to identify the onset of treatment, and identify the timing of treatment in relation to at least one component of the cascade and to analyze the relational pattern to identify the earliest trend comprising a component of the cascade, identify the onset of treatment, and identify the timing of treatment in relation to said earliest trend. In another embodiment for processing electronic medical records of at least physiologic parameters and laboratory data comprising a computer programmed to generate a large set of time-series of data of a patient including at least data relating to the physiologic state and/or care of a patient, convert the datasets, including at least the monitored datasets and laboratory datasets into parallel and overlapping time series, identify occurrences comprising at least, inflammatory occurrences, metabolic occurrences, volumetric occurrences, hemodynamic occurrences, therapy occurrences, hematologic occurrences, respiratory occurrences, identify the timing of the occurrences, identify at least one relational pattern of occurrences along a plurality of time series which is indicative of failure cascade of at least one of a sepsis cascade, a pulmonary embolism cascade, a metabolic cascade, and a microcirculatory failure cascade, output at least one of an indication of the cascade, the timing and type of the occurrences along the cascade, and length of the cascade. Another embodiment comprises a method for converting the global electronic medial record into a patient monitors the method the electronic medical record system having a display comprising steps of converting the electronic medical records into sequential and timed trends comprised of at least positive trends and negative trends of both the physiologic parameters and the laboratory data, detecting relational trends comprised of a combination of positive and/or negative trends, detecting complex cascade patterns comprised of a plurality of combinations of relational trends, outputting a display of the image of the detected complex cascade, outputting a warning indicating the detection of the complex cascade pattern, and tracking the growth or decline of the complex cascade and output an indication indicative of growth or decline.

In another embodiment the patient data processing system for processing electronic medical records of at least one patient comprising a computer programmed to convert at least the physiologic and laboratory data of the electronic medical records into a predetermined format for imaging, imaging the formatted electronic medical record, detect an image indicative of at least one of patient physiology and patient care, output an indication of the presence of physiologic failure. The computer may be further programmed to analyze the images to detect relational patterns of the detected physiologic failure to determine the severity of the physiologic failure and/or to detect relational patterns indicative of the patient response to the detected physiologic failure to determine the severity of the physiologic failure and/or to detect relational patterns indicative of patient care in response to the detected physiologic failure to determine at least one of the timeliness and efficacy of the care. The physiologic failure can for example be at least one of sepsis, severe sepsis, septic shock, a sepsis cascade, microcirculatory failure, a shock cascade, a septic shock cascade to name a few.

The predefined format may comprise a time series matrix, an objectified time series matrix, or anther format. The predetermined format may include at least one region comprised of at least one collection of time series of specific physiologic components. For example at least one of inflammation indicators, respiratory indicators, cardiovascular indicators, and metabolic indicators to name a few. The predefined format can comprise a plurality of regions comprised of a plurality of collections of time series of different specific physiologic components. The images may be comprised of aggregations of variations of physiologic data and laboratory data, the variations having positive or negative slopes, and/or aggregations of relational variations of positive and/or negative trends of physiologic data combined with positive and/or negative trends of laboratory data.

The patient data processing system may include an image archive system for archiving images of physiologic failure and for sharing these with other processors to grow the general archive and knowledge of the different images and variations of the images of failure. The patient data processing system may convert the time series matrix into a predetermined format of the time series matrix and image the formatted time series matrix to detect an image indicative of physiologic failure.

One embodiment comprises a patient data processing system having an object recognition system, for processing medical records of at least one patient comprising a computer programmed to convert the medical records of at least the physiologic and laboratory data of at least one patient into a time series matrix defining vertical and horizontal axes, and, using the object recognition system, search the time series matrix continuously or intermittently for a cascading plurality of relational patterns indicative of evolving physiologic failure along both the vertical and horizontal axes of the matrix.

Another embodiment comprises a patient data processing system for analyzing electronic medical records for real-time detection of physiologic failure comprising steps of continuously or intermittently search the medical records to detect events along the time series matrix, detect relational events along the time series matrix comprised of the detected events, detect relational cascade patterns comprised of a plurality of combinations of relational events, take action based on the detection of the at least one pattern wherein, for example, the pattern is indicative of physiologic failure.

In one embodiment the search engine is programmed to detect cascades comprised of at least a plurality of linked perturbations and trends of physiologic and laboratory data associated with relational compensation creating a progressively enlarging aggregation of progressively greater numbers of perturbed physiologic and laboratory data. The processor may be further programmed to determine at least one characteristic of the cascade, the characteristic comprising at least one of, the severity of the cascade, the duration of the cascade, the time of onset of the cascade, and the maturity of the cascade, the timing relationship of the cascade to other events or other cascades, the cost associated with the cascade, the global pattern of the cascade, the time of termination of the cascade, the components of the cascade, the state of evolution of the cascade, the length of stay subsequent to or in association with the cascade, the treatments associated with the cascade. The characteristic of the cascade may be defined by, for example, the number of perturbations and/or trends which comprise the cascade, the severity of the perturbations and/or trends, the number of systems affected by the cascade, the presence, number and/or severity of failure of compensation in response to perturbations associated with the cascade, and the growth of the cascade to name a few. The processor may be programmed to determine the rate of growth of the evolving cascade as by for example one or more of the increase in number and/or severity of new perturbations being added per unit time, and the increase number of systems affected, and/or the increase number of perturbations present in different systems, to name a few.

The processor may be programmed to detect the events or components which are temporally and/or spatially associated with the cascade but which are not part of the cascade for example treatment, surgical procedures, transport, injections, blood transfusion, sedation, IV assess, catheterization, manipulation, to name a few.

A processor-based system may characterize and quantify patient physiological conditions by analyzing data relating the patient into time series data and then generating an image or moving image of the abnormal components of the time-series that may be further processed into operator-interpretable data. According to one embodiment, this may be accomplished by generating a large set of time-series of data relating to the physiologic system, converting the datasets (including monitored datasets, laboratory datasets, and historic datasets) into parallel time series of each data component, separating the unperturbed time-series components from the perturbed time-series components, aggregating the abnormal components into a real-time motion pictures of the abnormal components, and recognizing and interpreting the motion pictures and the events relational events and image components of the motion picture.

In one embodiment, data from the electronic medical records and patient monitors are used to generate graphical displays, which may include moving pictures of the patient condition. In an embodiment, such moving pictures, or animated displays, may be referred to as "motion pictures of physiologic condition" (MPPC). Provided herein is a processing system and method for generating real-time MPPC of clinical data. The data and/or images may also be analyzed to detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate the MPPC. In addition, the MPPC may also include a graphical representation of any treatment applied in association with the clinical condition.

Once the image or moving image (i.e. an image that includes more data over time as the patient monitoring progresses) MPPC of the patient condition has been generated, this image may be further processed to create an operator-interpretable indicator to assist in patient diagnosis and/or treatment. For example, the image may be directly compared to a database of similar images taken from patients with clinically confirmed diagnoses. The database image or composite of multiple images with the greatest similarity to the generated image may indicate the correct diagnosis for the patient. For example, if the generated moving image, particularly as the image progresses over time, has the greatest similarity to a database image indicating "myocardial infarction," a processor may generate a text or other indicator to a healthcare provider indicating such a diagnosis. The processor may also indicate that additional tests should be ordered to confirm the diagnosis. The processor may also indicate and/or provide orders for specific treatments in light of the diagnosis. In an embodiment, a moving image may be indicative of two or more clinical conditions. The processor may indicate tests that may rule out one or more of such conditions. In addition, over time, one condition may be determined by the processor to be more likely while additional time-series data may also rule out another condition.

These database images may be formed from retrospective clinical data. In an embodiment, the images may be analyzed for similarity by any suitable technique, including image registration. In an embodiment, the individual time-series objects that make up the image may be processed as a group for similarity to other groups of time-series objects associated with a particular diagnosis or clinical condition. The MPPC may, for example, include abnormal and/or perturbed components and in particular "Motion Pictures of Physiologic Failure" (MPPF) of the physiologic system and of exogenous forces relating to that system.

Also provided herein is a processor and processing method for the automatic generation and/or analysis of the images of physiologic and/or clinical condition and the characterization and aggregation of the image components of complex dynamic systems, such as physiologic systems and medical care systems. The processing system may generate real-time MPPC of healthcare signals and processing those images to timely detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate and then recognize motion pictures of physiologic failures and of the treatment applied in association with the failures. According to one embodiment, a processor first renders parallel time-series from each of a plurality of sensors and testing sources, which are applied to broadly monitor the dynamic system for failure. In an example, a processor programmed with instructions for time series objectification of patient data detects patterns along the parallel times-series, converts these patterns into time series of discrete objects, then organizes these objects into discrete relational objects (such as binary objects, or relational binaries, derived of relational object pairs). The processor then organizes the relational binaries to render a unifying programmatic image of the physiologic system and the care provided. The processor then automatically recognizes objects in the image components and may be able to perform analysis on the images.

One embodiment may a patient safety processor having a single processor or a combination of processors programmed to generate time series objects, a relational binaries, moving images, patient safety images, and/or patient safety visualizations. The patient safety processor outputs images of the patient's physiologic system and medical care. In an embodiment, the processor includes processing functions for time series objectification, relational binary processing, and an imaging processing. In an embodiment, the imaging processing includes a single matrix construction processor.

According to an embodiment, perturbations detected by the processor are converted to image components that may be used to generate a moving image. In an embodiment, an MPPC may be representative of a "motion picture of physiological failure" (MPPF) when a failure image becomes progressively more complete and recognizable by the processor as each additional failure image component is added. One embodiment may involve building a dynamic real-time image of disease, injury, and/or drug reactions, the care provided, and the expense associated with that care. The image is initially associated with initial image components including one or more minor perturbations, which may for example be caused by circulation of one or more toxic and/or immunogenic material of endogenous or exogenous origin. At first these perturbations, such as toxins, inflammatory and/or thrombogenic mediators, may induce and/or cause only minor changes in cell permeability, ion flux, and trigger various minor physiologic perturbations and responses each of which may produce an image component. The measurements of various mediators, ions, biologic profiles, as well as standard blood tests, and the outputs of vital sign monitors may begin to vary as a function of these early physiologic perturbations and responses, and it is these variations that enlarge the group of image components from which the larger image (i.e. the MPPF) is derived. Early in the process, each of these alterations in permeability, cell injury, mediator production, and physiologic perturbations, when considered in isolation, are often minor. However, collectively they may represent the early manifestations of a nascent and evolving moving image of a serious clinical condition.

According to one embodiment, each perturbation is programmatically organized to form an image component of the MPPC. Many of these detected images components may be isolated because they are related to a benign process, and the image may self-extinguish or may not develop into an image associated with a clinical condition involving intervention or an MPPF. Yet, as noted above, others may represent the first image components of an early moving image. Provided herein are systems and methods for the detection of the early image components of an evolving moving image to provide timely detection of physiologic failures before these failure progresses to shock (including, for example, hypovolemic, obstructive, septic, toxic, cardiogenic, hypoxic, and/or hypercarbic shock.) In one embodiment, it is advantageous to detect the early image components of the moving image before shock develops to improve the prognosis for the patient and to apply goal-directed therapy while clinical intervention is still beneficial.

According to one embodiment, a patient safety processor generates a MPPC, which may be used for processor-based protocolization of care. This motion picture may be comprehensive of multiple data sources, including not only the events comprising a single or few parameters, such as heart rate, but also other parameters that may include, for example: the slope and pattern of the heart rate, the slope and patterns of the systolic pressure variation, the slope and patterns respiration rate, the slope and patterns $SPO_2$, the slope and patterns ventilation-oximetry index, the slope and patterns drug and fluid infusion rate, the slope and patterns blood pressure, the slope and patterns of the Neutrophil count, and the slope and patterns of inflammatory and/or thrombotic markers, and various other blood, urine and/or exhaled gas test to name a few. The signals from all of these sources may be converted to time-series and/or step functions and may, for example, be physiologic signals, therapy signals, laboratory signals, or historical signals, which may be objectified, as by an objectification processor, to produce the discrete programmatic objects (events). According to one embodiment, the processor detects a first discrete event that includes a pattern or value of at least one medical signal, and a second discrete event that includes a second pattern or value of at least one medical signal, the processor then aggregates at least the first event and the second event to produce a first relational object, the processor further detects a third event that includes a pattern or value of at least one medical signal, and a fourth event that includes a second pattern or value of at least one medical signal, the processor then aggregates at least the third event and the fourth event to produce a second relational object. The first relational object and the second relational object are then aggregated to produce a first image component. Additional image components are built accordingly and the image components are then aggregated according to the time of occurrence to derive the moving image and care.

In an example, the pulse related components of the typical motion picture of sepsis failure cascade would include occurrences such as early rise in heart rate, rise in pulse amplitude, and rise in slope of the pulse upstroke (as measured at the finger tip) in combination and typically proceeded by a brisk rise in inflammatory markers. In contrast the typical motion picture of occult hemorrhagic failure cascade (as for example due to heparin related retroperitoneal hemorrhage) would include occurrences of an early rise in heart rate, a fall in pulse amplitude, and a fall in slope of the pulse upstroke (as measured at the finger tip) and a rise in the respiratory related pulse pressure variation and a fall in hemoglobin. According to one aspect of the present invention all of these occurrences along the image of an occult hemorrhagic failure cascade can all be derived from a multi wavelength pulse oximeter.

According to an embodiment, a relational binary processor is provided that divides detected variations into discrete alpha events and beta events, which are combined by the relational binary processor to construct the relational events which are termed relational binaries. These relational binaries are aggregated according to timing to construct image components. These image components are then further aggregated according to timing to construct and progressively build MPPC (from which visual images or electronic representations may be derived as desired). These MPPC are often moving images of catastrophic cascading failures, thereby allowing more reliable detection to allow timely rescue of the patient.

The signals may be chemical or physiologic measurements, as provided by patient monitors, recorded in the electronic medical record, and/or may be biomarkers specifically ordered, either automatically by the processor or manually by the clinician to indicate the potential presence of the sepsis (as those, for example, disclosed in U.S. patent application Ser. Nos. 10/704,899, 11/647,689). The presence and/or concentration of such markers may be presented in the context of the MPPC with the timed positioning relative to the others parameters, which then allows the relevance of the biomarker to be much more readily identified. According to an embodiment, the temporal and relational pattern of inflammatory markers and temporal and relational patterns of contemporaneously measured or associated physiologic parameters are aggregated to produce a progressively enlarging MPPC of an evolving patient condition.

Therefore, to achieve the detection of various pre-shock states as well as earlier detection of failures, one embodiment detects early variations and aggregates them to provide an MPPC to dynamically present expanding failure cascades of pre-shock and shock states. This allows separation of expanding images from the smaller and less expansive image components having benign characteristics, and further allows separation of the images of minor isolated failures from failures that progress to generate an expanding MPPC heralding the potential for transition to one of the shock states. Each group of images as well as the complete MPPC and care may be analyzed for the purpose of assessing patient care in a hospital, a ward, or under the care of a given healthcare worker.

The occurrence of a large number of image components indicating non cascading failures which self extinguish may be indicative of an unstable patient population or poor health care delivery. In the alternative a large number of cascading failures are indicative of major risk of a high rate of death or injury in that environment or under that healthcare workers care. The MPPC and the image components may be used to determine if that is due to the patient population or the quality of the care.

One embodiment detects failure cascades along with the determination of the specific fundamental perturbations, or treatments, or lack of treatments that occur early in a failure cascade. Specific fundamental failures are detected before they progresses to complex failures and particularly before they progresses to the pre-shock or shock state. Furthermore, the processor builds an image derived of the relational perturbations and treatments as the cascade expands. According to one embodiment, each time series is processed to separate expected events from unexpected events. The unexpected and/or abnormal events are then aggregated further to repetitively generate relational events, image components and finally the MPPC which comprises a motion picture of the cascade (if present) as well as the treatment applied in association with the cascade. This MPPC is further processed to allow the detection of the probable cause or causes of the occurrence of the moving failure images well as the image components of the MPPC as it evolves thereby allowing detection of the nature and cause of the failure cascade.

As noted above according to one embodiment, an analysis is provided wherein the fundamental components of the analytic process comprise a basic relational variable that includes a plurality of events. In a preferred embodiment, the basic relational variable is that includes two events (a relational pair) and this is called a relational binary. In one embodiment, the relational binaries are initially selected by the users as from a menu (or by a drag and drop interface) of relational binaries and/or of events from which the user builds the desired object binaries the binaries are then used as by drag and drop to build the image components and MPPC for detection. This may be performed by, for example, by national or regional expert groups, or by specific departments in a hospital, or by an individual physician to provide custom management. This may also be automatically performed by the processor (as, for example, through the investigation of a large number of historical data sets that have been comprehensively analyzed and categorized according to outcomes. The objectified time series matrix and/or the MPPC may be may be outputted in various interactive, hierarchical, and relational formats for review and automatic or manual adjustment.

The MPPC may detect a wide range of failures. For example: "physiologic failures, treatment occurrence failures indicating the absence of expected treatment in relation to a given perturbation, testing occurrence failures indicating the absence of expected testing in relation to a given perturbation, treatment response failures indicating the absence of the expected correction of perturbation or the occurrence of a new potentially complicating perturbation in relation to a given treatment and/or dose.

The processor combines the complex data of the electronic medical record into a single motion picture of perturbations, treatments, physiologic responses, diagnostic testing, recoveries, diagnoses, missing data, patient locations, and/or other datasets. Dynamic images are generated of relational variations of a set of time series associated with a complex system to generate a real time motion picture of a failure of the system and/or of forces applied to the system. According to one embodiment of the present invention, the patient safety processor automatically outputs a unified timeline, for example, derived of detected images of a given type. According to another embodiment of the invention the processor, upon detecting a failure cascade, may present and highlight the evolving MPPC in real time on an outputted display of an image diagram for the physician to review. The portion of the motion picture, which has already been completed, may be reviewed backward and forward to review in a single summary snap shot view.

In one embodiment, an electronic medical record may be converted to an MPPC. A patient data processing system comprising a processor programmed with instructions for converting an electronic medical record into trend data, such as sequential, timed data, for example trends of physiologic parameters and laboratory data over time. When the data is converted into trend data, the processor may detect relationships between the trend data. For example, such relationships may include positive and/or negative trends. The relationships may be relational trends (i.e., when one parameter goes up, another parameter goes down). Complex cascade patterns of physiological conditions may be formed from a plurality of combinations of relational trends. The complex casade may form an MPPC, for example of sepsis, severe sepsis, septic shock, and microcirculatory failure, a shock cascade, and a septic shock cascade.

For example, a processor may process the electronic medical record and search to detect sequential and timed trends including positive and negative trends of physiologic parameters and laboratory data. Then, the processor may determine relational timing of the detected positive and negative trends to detect a complex cascade patterns that include a plurality of combinations of positive and negative trends evolving in sequential timed relation to each other. The processor may output an indication of the detected complex relational cascade pattern. For example, the indication may be physiologic failure, such as sepsis, severe sepsis, septic shock, and microcirculatory failure, a shock cascade, and a septic shock cascade. The processor may also provide detailed information about the individual trends, such as the length of each trend or the timing of the entire cascade. If therapy information is included in the electronic medical record, the image may include an indication to mark the onset of therapy and to determine and output at least an indication of timing of therapy in relation to the cascade. If the electronic medical record is from a patient that is still in care, the processor may include an alarm functionality to indication early points in a failure cascade.

In another embodiment, a patient data processing system may identify specific positive and negative trends, such as a combination of inflammatory trends, metabolic trends, hemodynamic trends, hematologic trends, and respiratory trends. After the identification of the trends, the processor may identify the relational timing of positive and negative trends, which relationally or collectively are indicative of the septic shock or pre-septic shock failure cascade to identify and output an indication of the septic shock or pre-septic shock failure cascade.

During a failure cascade, the earliest point in the cascade may include an earliest trend (e.g., a respiratory, immunologic, hemodynamic, or other patient trend) that marks the beginning of the cascade. Therapy intervention at this point may have the highest chance of success. In one embodiment, a processor may analyze the relational pattern to identify the earliest trend of a component of the cascade, identify the onset of treatment, and identify the timing of treatment in relation to said earliest trend. Such analysis may benefit caregivers in determining which therapies have the highest success rate for a particular physiological condition cascade. Alternatively, such information may also help a physician determine which types of cascades are likely to be self-limiting.

Many physiologic failures such as, for example septic shock, pulmonary embolism, congestive heart failure, respiratory arrest due to narcotics in the presence of sleep apnea, thrombotic thrombocytopenia purpura (TTP), hemorrhage due to anticoagulation, respiratory failure due to broncho spasm, and adult respiratory distress syndrome, but not limited to these clinical conditions, begin with one or two non-specific perturbation(s). Physiologic failure is commonly a relational expansion, often beginning with a fundamental physiologic perturbation at a single focal point in time. In fact, this initial perturbation is often completely masked once the cascade has progressed past a certain point. In such cases, testing or monitoring for the single perturbation may not be useful for making a diagnosis. In many cascading clinical conditions, the first perturbation(s) of the cascade may often only be detected in retrospect after the cascade has further progressed when the first perturbation(s) is no longer present. This provides a basis for optimizing the detection of the first point(s) by real-time imaging of the cascade as it develops and then examining the image to determine the first perturbation(s).

While a pattern of a single time series provides a larger image of a dynamic process than a single value or range, such a pattern is still only a tiny image fragment of the process. The determination of thresholds and even the detection of various patterns of perturbations comprise incomplete analysis, which will inevitably allow an unacceptable rate of progression to catastrophic failure. Even in situations wherein a measurement or test may seem definitive as a stand-alone test, action or conclusions based on a single value (or an average of a plurality of values) will have a reasonable probability of being incorrect. Consider, for example, a single measured spot $SPO_2$ value of 94. This value is largely meaningless without knowing if the $SPO_2$ is rising, falling, or cycling. Yet this infinitesimal image fragment of a patient's complex physiologic system is used everyday in hospitals to determine care. Furthermore, even if the pattern of the $SPO_2$ is known (for example the $SPO_2$ has been stable at about 94 for at least 12 hours) this is an incomplete image, which is largely useless and, in fact, a potentially misleading piece of information. Without knowing the relational pattern of the minute ventilation during the related time interval of the measured $SPO_2$ pattern, the healthcare worker may be lulled into a false sense of security even as the patient is dying of septic shock or heart failure. Furthermore, an alarm or interpretive output which is based on a programmatic image of both the patterns of both the $SPO_2$ and the related minute ventilation without additional relational elements of the image, such as, for example, the associated pattern of the white blood cell count, temperature, pulse, blood pressure, microbiologic values, and medications will be incomplete leaving too much synthesis for the healthcare worker. In another example, consider the detection of a pattern of a sustained rise in pulse or respiration rate. Each such pattern represents a tiny fragment of the present physiologic state and each pattern may be benign or alternatively may be an early image component of a much larger dynamic process of failure often associated with an evolving failure cascade. The difference between a benign or pathologic rise in pulse or respiration rate cannot be determined with this tiny image alone and often cannot even be known at the time of the onset of the rise. Therefore a tree diagram protocol with a branch based on a rising pulse or rising respiration rate adds a great degree of programmatic complexity with a high risk that the protocol will precede down the wrong pathway.

As noted above when the detection and the determination of the mode of potentially fatal but profoundly complex physiologic failures is left to a population of heterogeneous healthcare workers, an unacceptable rate of death may be anticipated.

As well, an incomplete analysis of the physiologic system will often cause the healthcare worker to generate a large amount of investigation, testing, analysis and evaluation that is not necessary and therefore increases the cost of overall care. Further, these false paths of treatment and evaluation may distract the care worker from the determining the actual operative failure modes, which will ultimately induce adverse outcomes.

Prior to shock, a patient's physiologic system is perturbed by both disease and treatment. A given treatment provided to correct a perturbation might reduce the perturbation, have no effect on the perturbation, exacerbate the perturbation, cause another perturbation and/or make another perturbation worse or better. To determine which effect a treatment is having and to assure that this determination of treatment effect is complete, it is necessary to collect and, just as importantly, as provided by one embodiment, organize and analyze large amounts of relational data in a timely manner.

Another problem is that, within present hospital systems the healthcare worker is forced to do a great deal of archeology (digging, isolating, identifying, etc.) before synthesis may be effectively completed. For this reason, the synthesis of information by the healthcare worker is often not executed in a manner, which allows immediate searching, filtering, re-analysis, etc. This friction combined with the typical workload of healthcare workers limits the number and range of high-level scenarios, which may be investigated. Also the healthcare worker may, because of lack of available organized data and time, execute decisions without a complete set of synthesized information and worse, may not realize that this is the case.

For these reasons, even with conventional electronic medical record embedded protocols, patients remain subject to a range of failures across a broad range of failure modes based on the complexity of their individual condition and the complexity of the environment facing the care giver. In fact, because failures often overlap, one protocol may reduce the risk of one failure while increasing the risk of another. For example, oxygen given to treat hypoxemia under one protocol may delay the detection of pulmonary embolism by stabilizing the SPO2 and hiding the early signs of impending shock from the healthcare worker.

Although the number of potential modes of failure is very high in any hospital environment, the occurrence of certain modes of failure is reasonably likely under a given set of circumstances in the hospital. A failure mode diagram illustrating common modes of failure given a combination of a group of diseases is shown in FIG. 1. The number of potential failures may be very large (in the hundreds) for a given patient in a hospital setting and the nurse or physician is often expected to monitor many such patients on the floor while timely detecting the failures such that the nurse is expected to timely detect even a single failure from as many as a thousand failures which may occur among the patients under his or her care. For this reason, processor based failure imaging and detection is desirable.

FIG. 1 illustrates a complexity diagram 200 of an exemplary patient on a medical hospital ward. The diagram 200 demonstrates the level of complexity that may be modeled into moving images as provided herein to determine the nature of and origin of perturbations within this level of complexity. The diagram 200 is one type of failure mode diagram which may be constructed by an expert panel and then used according to one embodiment to facilitate the construction of the various components the moving images provided herein, including the events, relational binaries, and image components. The failure image component diagram 200 includes a number of overlapping diseases present for this single patient including diabetes 202, congestive heart failure 204, arterial fibrillation 206, stroke 208, sleep apnea 210 and sepsis 212. The diseases may induce physiologic failures, such as a divergent rise in ventilation 216, a rapid ventricular rate 218, pulmonary edema 214, and fall in oxygen saturation (hypoxemia) 222. Furthermore the treatments are potentially associated with medication failures such as a high threshold breach of the partial thromboplastin time (PTT) or a low threshold breach of the glucose (hypoglycemia) 234. Additionally, the administration of a treatment (for example, insulin 224, a diuretic 226, an ACE inhibitor 228, a beta blocker 230 and/or heparin 232) to a patient may lead to additional physiologic failures (for example, a fall in platelet count (thrombocytopenia) 236, the occurrence of heart block 238, a fall in serum potassium (hypokalemia) 240, a fall in serum sodium (hyponatremia) 242, a fall in blood pressure (hypotension) 244. In one embodiment, a single patient may have early high blood glucose (hyperglycemia) 215 followed by later low blood glucose (hypoglycemia) 234. As shown, the interrelationship of progression of multiple diseases, the patient symptoms, and multiple treatments may lead to treatment delay 248 or confusion 220.

FIG. 2 depicts an overview of the flow of analysis for modeling complex patient physiological condition in one embodiment. A wide range sources may provide inputs to the modeling. For example, patient monitors 256, patient records 272, historical patient data 260, lab results 264 and therapy data 268 may provide the raw data input into the analysis stream. These inputs are converted to a set of parallel time series 276. Patterns and threshold violations along this plurality of parallel time series identified, coalesced, synthesized and organized into discrete objects forming object streams 280 within each channel. These discrete objects are analyzed to identify known relational patterns into instances of relational binaries 284. In one embodiment, expert systems then further refine the analysis by organizing and synthesizing these relational binaries into a set of failure images 288, which as an aggregate whole make up a unified programmatic image of the complex and dynamic state of a patient and/or a patient population.

Figure 3A:
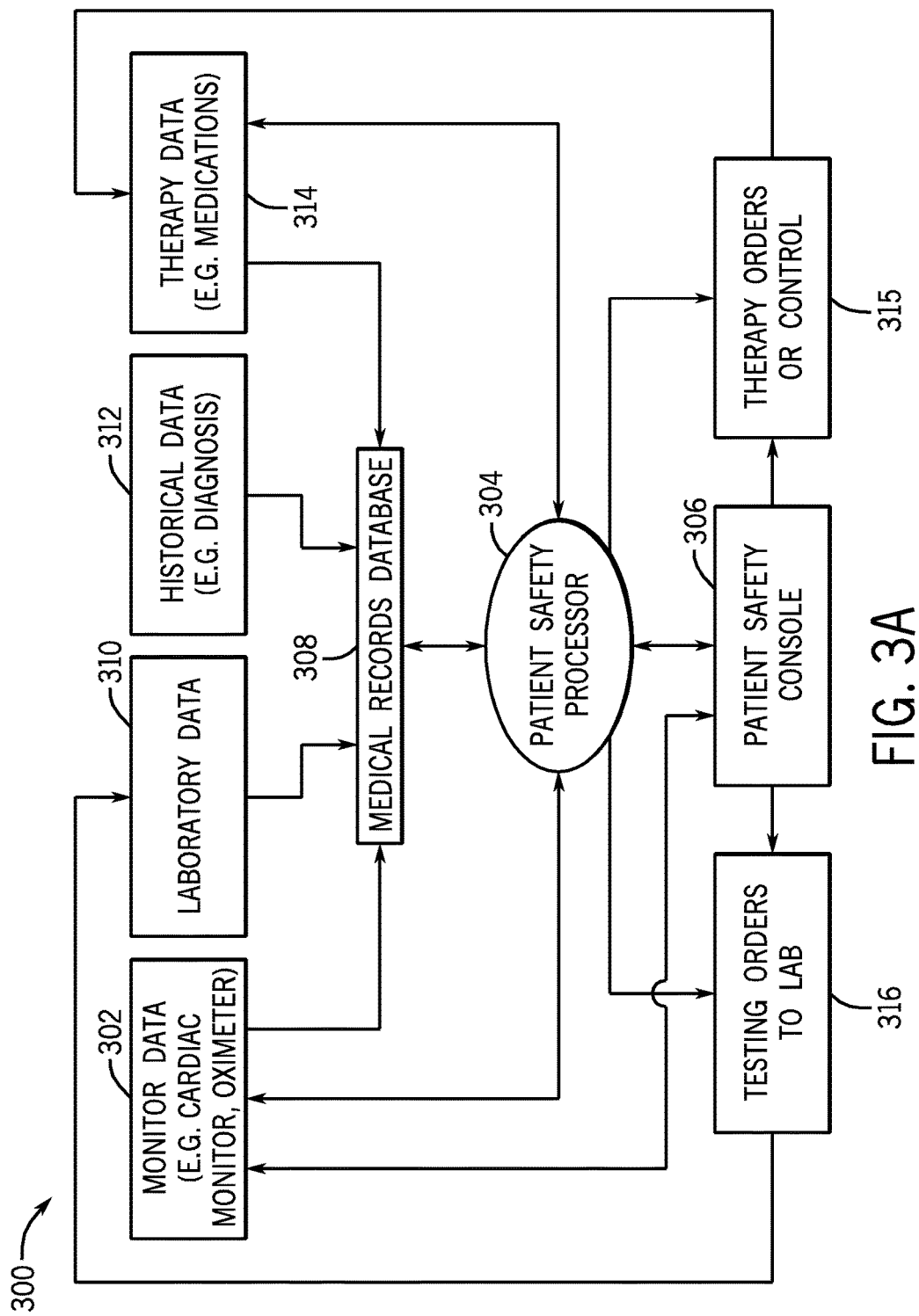
FIG. 3A is a data flow diagram in accordance with an exemplary embodiment.
Figure 3B:
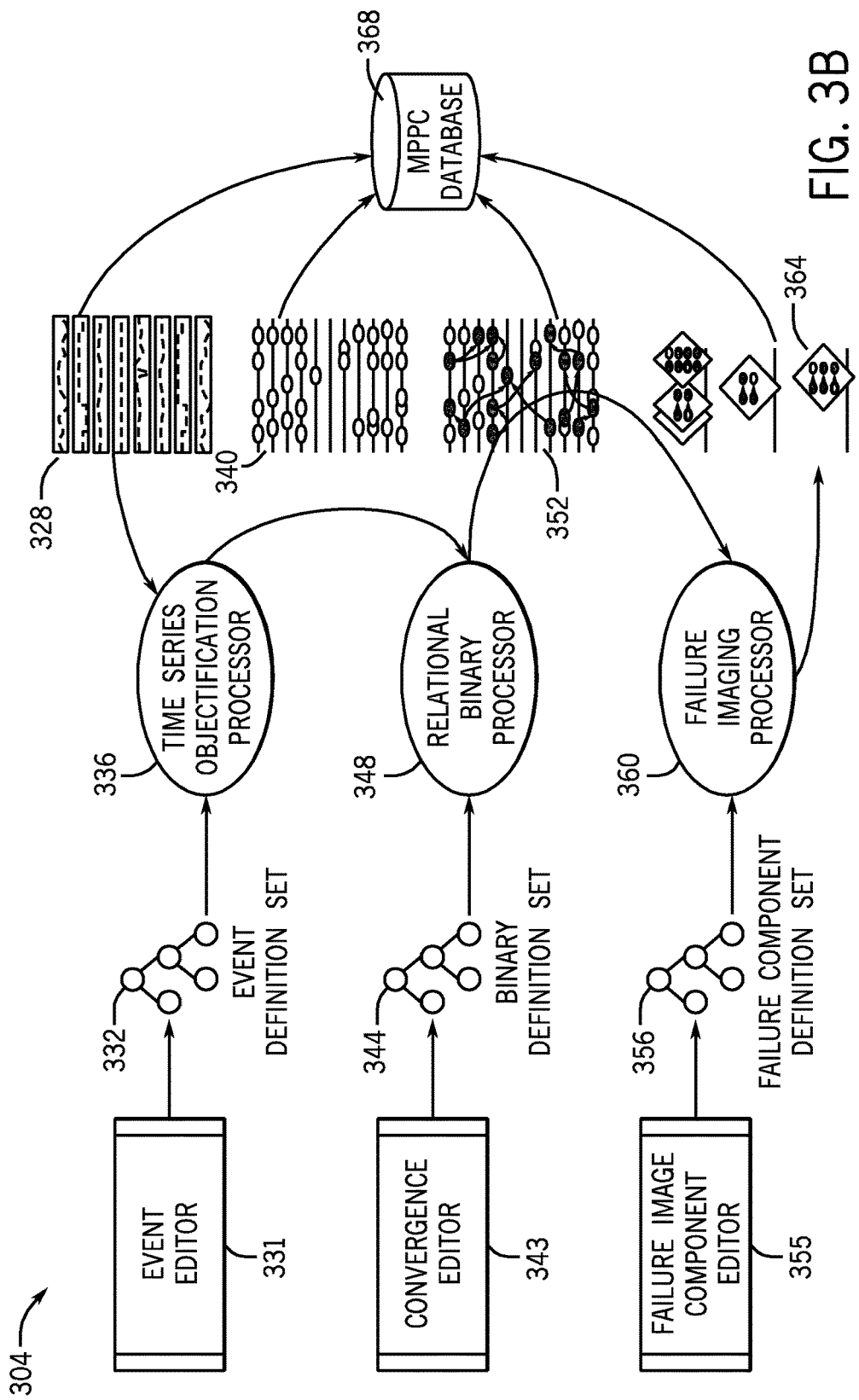
FIG. 3B is a diagram of an exemplary system in accordance with an exemplary embodiment.
Figure 3C:
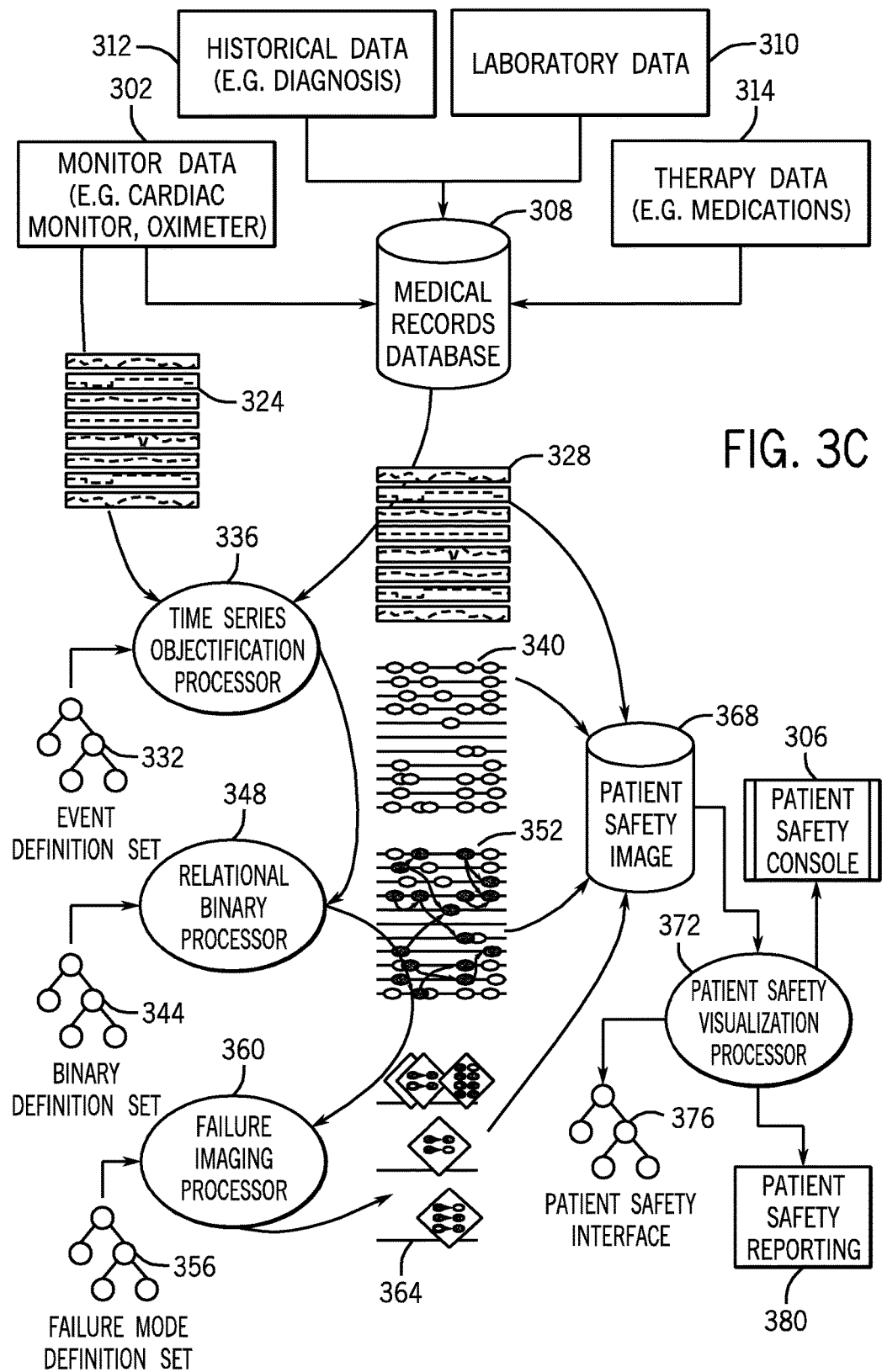
FIG. 3C is a data and action flow diagram in accordance with an exemplary embodiment.

FIG. 2 depicts the flow of analysis 240 from raw data to the aggregate of images, while FIG. 3A and FIG. 3B includes some of the data stores, data flow, processors and output mechanisms within the exemplary embodiment. FIG. 3A depicts another data flow of one embodiment. The data management system 300 includes a monitor 302, a processor 304 that may include, for example, time series objectification processor 336, relational binary processor 348, and failure imaging processor 360. Alternatively, processors 336, 348, and 360 or instructions for performing the processing steps of time series objectification, relational binary processing, and/or failure image processing may be located on one or more additional processing components in communication with processor 304 that are part of the system 300. The processor 304 is adapted to provide output of the analysis to a device 306, which provides an interface for a healthcare worker. The data flow involves inputs from a wide range of sources (304, 308, 310, 312, and 314). As shown, the inputs may be sent to a processor 304 that may direct further action for the patient, including testing orders 316, indicators to the healthcare provider that may be displayed on a console or device 306, and therapy orders 315. Accordingly, the healthcare worker may use the device 306 to control and oversee the entire hospitalization process. In one exemplary embodiment, the processor 304 may be used to drive the device 306. The processor 304 may be adapted to constantly process all of the real-time data of all of the patients regardless of the status of the viewing console and to automatically send testing orders 316 and/or therapy orders 315 based on the analysis of the images derived from the processor 304, as will be discussed.

The data management system 300 may include one or more processor-based components, such as general purpose or application-specific computers. In addition to the processor-based components, the data management system 300 may include various memory and/or storage components including magnetic and optical mass storage devices and/or internal memory, such as RAM chips. The memory and/or storage components may be used for storing programs and routines for performing the techniques described herein that are executed by the processor 304 or by associated components of the data management system 300. Alternatively, the programs and routines may be stored on a computer accessible storage medium and/or memory remote from the data management system 300 but accessible by network and/or communication interfaces present on the computer.

The data management system 300 may also comprise various input/output (I/O) interfaces, as well as various network or communication interfaces. The various I/O interfaces may allow communication with user interface devices, such as a display, keyboard, mouse, and printer that may be used for viewing and inputting configuration information and/or for operating the system 300. The various network and communication interfaces may allow connection to both local and wide area intranets and storage networks as well as the Internet. The various I/O and communication interfaces may utilize wires, lines, or suitable wireless interfaces, as appropriate or desired.

In an exemplary embodiment, the device 306 is turned on as for continuous viewing (with a notification) by the processor 304 when images are indicative of a significant potential failure and/or cascade process or at a point wherein the patient's risk class exceeds a threshold value. The risk class may, for example, be derived as a function of a calculated instability index or a detected instability index pattern and/or detected failures. The instability index may be, for example, a confidence metric correlated with a matched image. For example, when an MPPC has a high likelihood of being associated with a serious condition, the instability index may be high. The instability index may be a numeric index, a color or graphic indicator, and/or an audio or text message.

In accordance with an exemplary embodiment, the device 306 includes an interactive single screen displaying items, such as one or more working diagnoses, differential diagnosis, parameters derived from patients including laboratory parameters, monitored parameters, and subjective parameters (e.g., sedation scale, confusion scale, or pain scale) or the like. In an embodiment, the term "parameter" herein may refer to an absolute or relative data point or set, a pattern, or a deviation, a range of such data points or sets, a pattern of such data, a relationship along a single set of data and/or or between a plurality of sets of data, and/or patterns of data. The data may be an objective data type or subjective data type and may be directly and/or indirectly derived or historical in origin. In addition various outputs from the failure imaging processor 360 (FIG. 3B) may be displayed. According to on embodiment, the processor 304 may provide data for display present on the device 306 or through a report (either electronic or paper) or within an electronic representation that may provide an interface to external systems.

The data management system 300 further includes a medical records database 308 including laboratory data 310, historical data (e.g., diagnosis) 312 and therapy data (e.g., medications) 314. The medical records database 308 is coupled to the processor 304 and to the monitor 302 so that those systems may have access the data stored in the medical records database 308. The processor 304 may include a component or direct link to the centralized patient medical record, which contains real time data and receives data input from all hospital sources. Thus, a database containing substantially all of the components relating to the patient available to the hospital may be directly accessible to the processor 304 in real time to allow the embedded relational processor render relational binaries, and construct and detect failure image components which include these data from varied sources.

In accordance with an exemplary embodiment, the processor 304 is adapted to comprehensively engage the medical records database 308. As discussed further below, the processor 304 may be programmed to provide for formal, automatic simultaneous engagement, of physiologic failure image components, medication failure image components, testing failure image components, aggregate failure image components as derived from the relational processor and to render them in a timeline for viewing.

The processor 304 may be adapted to provide an immediate review of all failure image components and to take action based on the detection of specific failure image components. The processor 304 may be capable of responding faster and more reliably than the healthcare worker because it may be adapted to constantly monitor the evolving failure image components form the earliest onset of the first divergent binary. The processor 304 may therefore detect failure image component cascades, which originate from single divergent binaries, which might easily be undetected by the healthcare worker until it is too late. The processor 304 may also be programmed to alarm on divergent or null binaries upon which no action has been taken or upon which the action has not corrected the evolving divergent binary or failure image component. For example, in a scenario in which the processor 304 has been updated by the nurse that a blood culture has been obtained, the presence of a null binary may be generated indicating testing failure image component if after a pre-selected time the result is not available to the processor 304 whereas the presence of a divergent binary indicative of a physiologic failure image component may be detected if the culture is positive. If testing failure image component is detected the processor 304 notifies the lab of the apparent delay. The notification is an alpha event and a receipt response to that notification is a true beta event. Therefore the failure of the lab to indicate receipt may cause the occurrence of a divergent binary, which may trigger the notification of the nurse in the same manner until a convergent binary concludes the sequence. If on the other hand, a physiologic failure image component is detected (the culture is positive), the processor 304 notifies the nurse again in the same binary generating fashion.

While a positive blood culture is the beta event of the culture testing binary, it is the alpha event for another group of testing binaries such that the initial divergent testing binary may cause the processor to assure acquisition of a complete blood count, a comprehensive metabolic profile, increased frequency of blood pressure and pulse measurements, ventilation indexing oximetry and other testing as programmed into the processor 304 in response to the specific divergent binary detected (in this case a positive blood culture). These new testing binaries may generate unexpected beta events (such as a low blood pressure, a high pulse, or high ventilation to oximetry index) and these beta events may thereby define a new set of divergent physiologic binaries. This new set of divergent binaries (in aggregation) may be sufficient to meet the pre-selected criteria of an aggregate failure image component suggestive of early septic shock, which diagnostic consideration now comprises an alpha event to a plurality of new binaries which have been programmed into the processor to assure timely and proper monitoring, timely proper patient location, and timely proper diagnostic testing, and timely and proper intervention in the event of the detection of this type of aggregate failure image component. In addition, the beta events of the divergent physiologic binaries which comprised the aggregate failure image component now become alpha events for new physiologic binaries wherein the beta event of each of the new binaries comprises the return of each these values back to a normal range within a pre-selected time period (thereby assuring, that the aggregate failure image component is corrected timely, if possible). In additional, the positive blood culture is also the alpha event for a treatment binary such that the processor 304 may be expecting to see the correct antibiotic in response to positive blood culture administered within a pre-selected time interval. If this does not occur a divergent binary indicating treatment failure may be identified and assured nurse notification may proceed by the binary building method previously discussed.

According to one embodiment, in response to the detection of any significant divergent physiologic binary, the device 306 may be programmed to prevent the failure of notification by building a set notification binaries, which must end with convergence. The device 306 may also be programmed to prevent failure to timely treat by building a set of treatment binaries, which must end with convergence. Further, the device 306 may be programmed to prevent failure test by building a set of testing binaries, which must end with convergence. The device 306 may also be programmed to detect associated physiologic failure image components by identifying divergent physiologic binaries in associated with the initially discovered divergent binaries.

According to one embodiment, the PSP includes an associated, connected and/or embedded eventing system. In this eventing subsystem, users may designate actions to be initiated or data to be recorded when a specific occurrence is identified. This eventing system may interface with other internal or external systems including notification systems, workflow systems, asynchronous communication systems, reporting systems, decision support systems, dashboards, data warehousing and/or data mining systems to name a few.

According to one embodiment the relational processor is self-modulating and provides an automatically expanding analysis, which is rapidly responsive to the occurrence of even a minor failure image component. The analytic activity of the processing system is capable of multidimensional growth and diminishment in direct response to the magnitude and number of failure image components detected. In this regard, the processor 304 upon the occurrence of a physiologic failure image component may generate a cascade of notification, testing, treatment, and physiologic binaries even if that failure image component comprises only a single physiologic divergent binary. The beta event of the physiologic binary may comprise the alpha event of each of a new generation of notification, testing, treatment, and physiologic binaries. Each of these new binaries also have a beta event, each which may induce the formation of other binaries wherein the beta event comprises the alpha of another binary of the same or another type. A spontaneously growing cascade of binaries thereby evolves toward assuring timely notification, timely testing, and timely restoration of physiologic stability.

A rapidly expanding, cascade of these types of divergent binaries indicates evolving patient instability of the patient or poor performance of the healthcare system. An analysis (as by objectified pattern recognition or statistical analysis) of the timed patterns of the types and sequence of the divergent binaries may allow the determination of poor health or poor responsiveness of the healthcare worker is causing the cascade to be propagated. As health is restored, and provided the healthcare workers are timely responsive, the binary cascade may automatically diminish and the various failure image components may no longer be detected. The outputs of the relational binary object processor therefore provides a self modulating processing system which may be readily used and further analyzed to track the health of a single patient, or the patients on a given floor, or the patients hospital wide. The outputs of the object binary processor also provides a self modulating processing system indicative of the quality of healthcare delivery provided to a given patient, on a given floor, or hospital wide.

The processor 304 may be applied to other complex dynamic data sets other than medical data wherein a self-modulating relational analysis and control would be useful. The processor 304 has utility for the data mining, for example in association with the processing of archived datasets to identify the failure image component process from the initial spark (the first divergent binary) to extensive system failure. The processing of archived datasets provides the opportunity to review the automatic modulation of the binary cascades which are derived of various failures and to facilitate the construction of dynamic failure image component diagrams for complex processes in the hospital, as well as in industrial processing such as the food, chemical, or pharmaceutical processing. The processor may be programmed such that the user may select each alpha event and allow the processor to detect, offer, and/or derive events and relational binaries, which have specified temporal, frequency, or spatial relationships with the selected event object. Alternatively the processor 304 may be programmed to construct its own set of convergent object binaries with a learning dataset by processing the outputs of healthy individuals and then the processor may be used to detect divergent binaries when applied to patients by identifying the lack of the expected beta events (which were defined by the learning dataset). Sensitivity for cascading (the initiation of further processing based on the detection of a divergence or a failure image component) may be adjusted by modifying the sensitivity for trueness of the beta event or by modifying the criteria such as slope, or magnitude of the objects during the objectification process. This provides a high degree of flexibility in defining sensitivity to the designation of a binary as divergent and this therefore allows a high degree of control over the sensitivity to cascade initiation, propagation, and extinguishment. Cascades may be modular or divergent or failure image component specific. A modular group of cascades may be selectable from a menu and then each one in the group modified as desired.

As shown in FIG. 3B, the processor 304 may include instructions for any number of processing functions. As shown the processor 304 may include an event editor 331 (creates event definitions 332), a convergence editor 343 (creates binary definitions sets 344), and a failure image component 355 (creates failure components 356). The event definitions 332, binary definitions 344, and failure components 356, may be used an inputs for the time series objectification processor 336, the relational binary processor 348, and the failure imaging processor 360. The time series Objectification Processor 336 is programmed, with the rules and parameters provided by the event definition set 332, to convert parallel time series (324, 328) of the electronic medical record 320. The relational binary processor 348 then, with the rules and parameters provided by the binary definition set, processes the object streams 340 to generate streams and cascades of relational binaries 352. Further then, the failure imaging processor 360, with the rules and parameters provided by the Failure image component definition set 356, synthesizes the relational binaries, and in some cases isolated objects from the object stream, into one or more images 364. The output of each of these three processors (336, 348 and 360) as well as the original time series upon which they were applied are stored in an MPPC database 368. In an example, the processor 304 may be programmed so that detection of one or more events, binaries, image components or detection of a specific MPPC, may cause the processor to take action such as provide an outbound notification of the detection, orders for testing or treatment, or direct control signals to a treatment and/or testing device to change, cease or initiate testing and/or treatment.

According to one embodiment, the relational binary processor 348 and the time series objectification processor 336 may adapt to the output of each other to modify the analysis. For example, the detection of an event, a reciprocation, an incomplete reciprocation or other objects or patterns by the time series objectification processor 336 may cause an adjustment to the cascade responsive to the detection of a divergence. Alternatively or in combination the criteria for designation of a wave segment as an event object within the time series objectification processor 336 (for example the slope criteria for identifying a fall event object of serum sodium) may also be adjusted based on the presence of a specific alpha event. In an example, when an alpha event comprising a diagnosis of cerebral vascular infarction (CVA) is detected, this may cause the time series objectification processor 336 to reduce the absolute slope (less negative slope) for designating a fall event object of serum sodium, which, is preferably one of the betas in such patients. By automatically reducing the absolute slope for the designation of the beta event the alpha diagnosis of cerebral vascular infarction is adjusting the sensitivity of the diagnostic process allowing automatic and dynamic adjustment upon the occurrence and detection of different physiologic vulnerabilities. In this example, the increase in sensitivity for detection of a fall event object in serum sodium (which, combined with the alpha that includes a CVA diagnosis) would comprise a divergent binary), which may trigger a diagnostic cascade for close monitoring of the serum sodium and/or the evaluation of additional laboratory studies and/or the reduction of free water delivery. This is desirable due to the unique vulnerability faced by patients with CVA as a function of the potential for inappropriate increase in anti-diuretic hormone due to the CVA.

Since the relational binary definitions within the binary definition set 344 may be individually defined and refined by processing large populations of historical data, correlations may be verified, rather than being simply proposed and maintained as a function of consensus or expert opinion. In one embodiment, cascades originated by criteria for divergence provided by an expert, which untimely lead to extinguishment without intervention may be automatically adapted to either change the sensitivity for the detection of the divergent beta or to change the cascade resulting for the divergent binary. In another example, cascades originated by criteria provided by an expert which continue self propagate and expand despite timely action and without progression of the physiologic divergence may be automatically adapted to either change the sensitivity for the detection of the divergent beta or to change the cascade resulting for the divergent binary. The sensitively and specificity may be further enhanced because the system may be applied to archived training data sets wherein the outcomes are known so the magnitude and direction of the cascades may be compared to the desired magnitude and direction of the cascades and adjusted accordingly. With applied archived datasets the application of auto-adaptive adjustment in event criteria, divergence criteria, or cascade generation may be applied until the cascades proceed without premature auto extinguishment and excessive propagation. Furthermore the system may be applied to hypotheticals on the missing data to allow determination as to how they might affect incomplete (null) binaries.

According to one embodiment the processors, including the time series objectification processor 336, the relational binary processor 348 and failure imaging processor 360, may output the results of their analysis into the MPPC Database 368. The MPPC Database 368 contains the time series 328 on which the analysis was performed as well as the results of analysis including the event streams 340, the relational pairs 352, the aggregate failures 364 as well as aggregations, relationships and alternative images of these elements. In one embodiment, the metadata rule-sets (both primary and alternative and/or temporarily overridden or altered elements) are persisted as XML (Event Definition Set 332, Binary Definition Set 344, Failure image component Definition Set 356) in the Patient Safety Image Database 368.

Time Series Objectification Processor

A time series objectification processor 336 may contain instructions as provided in U.S. patent application Ser. Nos. 11/280,559, and 11/351,449 the specifications of which are incorporated by reference herein in their entirety for all purposes. Accordingly, such processors may function by constructing a time series of each parameter derived during the process of the hospitalization and then objectify each time series. These time series may, for example, include objective measured values, drug dosing, infusion rates, and subjective clinical scores to name a few. At least some of the time series may be provided as a step function. For example, time series of the weights, serum sodium values, $SPO_2$, respiratory rate, heart rate, drug infusion dose, sedation score, pain score, stupor score, working diagnoses, an instability score, a severity of illness score, to name a few, may all be included. From these time series, the time series objectification processor may render an aggregate "object cylinder" or time series matrix for example, which may include parallel streams of objects derived from all of these time series.

In an embodiment, a time series objectification processor converts a set of time series into a stream of sequential and overlapping discreet elements or objects such that substantially the entire time series of data is converted to a time series of objects in a relational hierarchy of ascending complexity. The objects into which the time series is converted may be predefined by the user and/or adaptively defined. The discrete objects which are created represent and characterize an occurrence providing a time location and a set of properties derived from the aggregated data within the boundary defined. This process when applied to a plurality of parallel time series generates an Objectified Time-series Matrix (OTM). Objects may be very simple such as a brief rise or fall along a single time series, or highly complex such as a sepsis cascade object comprised of and inheriting hundreds of simpler objects of relational physiologic variation, treatment, and response to treatment to name a few across a large OTM. These objects along the OTM are differentiated by location and the properties derived and therefore individual objects can be qualified and the objects of the OTM can be searched against. The conversion of the time series matrix to form an OTM provides for identification, qualification and search ability of relationships between substantially all patterns and relationships which is embodied in the data of the EMR. Objectification is therefore one means of converting an electronic medical records into a particular format for imaging or searching for images. The objectification processor may for example be programmed as a continuous search engine to continuously search for predetermined complex objects which at this level of complexity comprise images (such as the image of an evolving sepsis cascades) along both the vertical and horizontal dimension across multiple parallel time series of the OTM). When the electronic medical records (EMR) of a patient is converted into an OTM, the continuous search engine may linked to an alarm processor to thereby provide an automatic alert upon detection of specified images (such as the image of a sepsis cascade, the image of failed or missed treatment, or the image of a drug reaction to name a few). This converts the EMR into a real time image generator with real-time detection of both complex and simple failures. The wide range of simple and complex relational patterns or images which are provided in an inheritance hierarchy of ascending complexity and are continuously searchable are derived of for example physiologic process, pathophysiologic failure, and the care of the patient, to name a few, are all exposed for continuous or intermittent searching or imaging along the OTM As discussed, one embodiment includes a patient safety processing system, which includes a time series objectification processor 336 and a relational binary processor 348. The relational binary processor 348 may be embedded into, or communicate with the time series objectification processor 336. The time series objectification processor 336 is programmed to convert parallel time series of the electronic medical records from a central source or a wide range of sources as well as from other processors (e.g., the Patient safety processor), into parallel object streams. The relational binary processor 348 then processes the object streams to generate streams and cascades of relational binaries. According to one embodiment, the processor 304 automatically outputs a unified timeline, for example, derived of detected failure image components of a given type. According to another embodiment the processor, upon detecting a failure cascade, may present and highlight the evolving MPPC in real time on an outputted display of a failure image component diagram for the physician to review. According to another embodiment, the processor 304 persists failure image components and all other results of the analysis into the MPPC Image Database 368, which may be the source for visualization, reporting, and interfaces into other systems. The portion of the motion picture which has already been completed may be reviewed backward and forward to review in a single summary snap shot view.

As discussed, according to one embodiment, the relational binary processor 348 generates relational binaries. Such relational binaries include an alpha event object and a beta event object. An early step in this process includes the defining the relational binaries by the user or by the processor. To define a relational binary, first, the alpha event is defined (as by the user or adaptively). The alpha event is defined both in terms of its channel and the object along the channel. In one embodiment, the objects along each channel are defined by characteristics (such as the slope, amplitude, or other features defining the object as discussed in the aforementioned patent applications). Alternatively, threshold violations may be identified as an alpha event. A beta event is defined, again in terms of its channel and its characteristics and may be either a pattern or a threshold event. Both alpha and beta events may also be defined in terms of the relationship of its characteristics to the characteristics of other events, such as those, which preceded the specific event. In one embodiment the user may define the relational objects, (as by using a drag and drop designer), by selecting the channel (which defines the time series type), and by selecting the event objects (for example a fall event or a rise event) which meet specified range of criteria, and by identifying the timed relationship (such as the time interval) of the beta event in relation to at least a portion of the preceding alpha event, and/or by identifying the spatial relationships and/or frequency relationships of one event to the other event. In one embodiment, alpha objects and beta objects are defined by the criteria provided to the time series objectification processor 336 alone for the detection of event objects such that the Relational Binary Processor may be concerned only with the detecting the presence and timing of detected event objects not with modifying or affecting the criteria for event detection if desired. (The detection of event objects by a time series objectification processor 336 may be as disclosed in U.S. patent application Ser. No. 11/280,559 and U.S. Pat. No. 7,081,095, the specifications which are incorporated by reference in their entirety herein for all purposes.) This is not to limit the functionality of the relational binary processor 348 (since processing systems, which incorporate the programming of the relational binary processor 348 to specify criteria, are included in an embodiment) to detect objects as a function of basic time series patterns by the objectification processes where these basic patterns are converted to discrete objects. The relational binary processor 348 then aggregates the relational binaries according to their time of occurrence and/or to specific criteria for aggregation set by the user or processor to derive image components and the image components are aggregated according to their time of occurrence and/or to specific criteria for aggregation set by the user or processor to derive the MPPC and care derived of events and patterns across hundreds of parallel time series. In a sense, the relational binaries and events become the discrete "pixels" from which MPPC of a patient's physiologic system are constructed by the processor 304.

According to one embodiment, the processor 304 or is also programmed to organize the events and relational binaries into larger aggregate factorable objects, which may also be constructed as a unified object timeline rather than a motion picture. Each aggregate factorable object includes a specific aggregation of events and relational binaries objects. In some aggregate factorable objects, the individual relational binary and event objects occur in a specific sequence or range of sequences (which may be overlapping) and the objects have a specific temporal relationship (or range of temporal relationships) with respect to each other. One specific type of object timeline may be specified as simply a grouped set. In another example, relational binaries are ordered in specified sequence in which the event and relational binaries objects were detected thereby defining the object timeline.

According to one embodiment objects of specified types may also be combined derived to render a "unified patient timeline" which is a simple summary of the patient's physiologic system and care. The MPPC and care provides the information at more comprehensive level. Both may be configured to provide further simplified summarization or image detail revealing drill down. The unified patient timeline may for example, represents an instance of at least one factorable aggregate object derived from a plurality of parallel time series into a single time-series or time line, often of relational binary objects of a specific type or plurality of types. In one instance the unified patient timeline and/or the MPPC and care is constructed to be a life long time line and/or motion picture, which preferably is recorded whenever signals are available, such as during a hospitalization or when connected to a home monitor or when blood testing is made. The beginning of the motion picture or time line is defined by the time of the earliest date of data (which may be derived from archived patient data) the unified patient timeline does not end until a patient dies. Segments of the timeline (or motion picture) may be separated for examination by location of the patient such as a hospitalization segment, or by actions taken to treat the patient, such as a peri-operative segment, or by events relating to altered patients states such as the segment immediately preceding death or while sleeping. According to one embodiment, an object nomenclature is provided which designates the timed and sequence relationships of the binary objects and events of a plurality the parallel patient related time series, thereby converting a large plurality of datasets into this single time series of factorable objects, which is readily outputted interpretable through application of a succinct nomenclature.

In one embodiment the physician may mark a test result or other data point as mistaken or anomalous. In this case the processor splits the analysis into two—the working analysis (which removes or alters the test result or other data point) and a background analysis (which maintains the original data). The processor may run scenarios in which the original test result stays in effect to determine if conditions occur that might have been expected from the "so-called" anomalous test. The background will not affect the working analysis but notification may be generated if a correlation of events is found in a sufficiently suggestive pattern to warrant a consideration that the original test results may not have been mistaken and, in fact, would account for conditions that do not fit the current working state (e.g., the state with the test results removed). Background analyses may be deleted according to time (e.g., after a certain amount of time in which no correlation to following events is found) or at the request of the user or system operator (e.g., to reduce resource utilization).

In another example the processor may be programmed to generate more frequent testing binaries to confirm or exclude an apparently evolving image. In this way the processor is trying to look as far forward as possible with additional testing to confirm the motion picture of a particular failure as early as possible so that the delay associated with waiting for the detection of a failure cascade as by various traditional threshold breaches is eliminated.

In an example, as part of assuring that the future image is complete, the testing binaries are designated such that the addition of certain drugs (the alpha event) into the image, may cause automatic orders for testing to monitor for complications related to the drug (the beta event) if selected, events, binaries, image components, or MPPC are present. In an example, if the physician orders heparin, a testing binary is generated and added to the image which includes automatic order for a platelet count every 48 hours. According to one embodiment, the time series objectification processor 336 is objectifying the time series of platelet counts to detect a least one fall event (as for example defined by a negative slope and/or a magnitude of fall and/or a threshold fall), if a declining slope is detected a divergent binary is generated and a marker indicating a fall is added to the image along the platelet count time series, the processor may generate more frequent platelet testing binaries, to confirm the presence of these divergent binaries in the image. If multiple divergent binaries are detected then the processor may generate different types of testing binaries wherein the alpha event is the fall in platelet count. This may trigger a cascade of testing binaries such as, for example, wherein the alpha event is a binary that includes a heparin treatment and a fall in platelet count t and the beta event is, for example, a platelet factor 4 assay or/and another assay.

In this way, using the failure imaging processor 360, the delay associated with waiting for an absolute or relative threshold drop in the platelet count is reduced. In addition the cascade may include additional testing binaries (as for hepatic function tests, to determine the safety of Argatoban, a medication which may be ordered if the image components are consistent with heparin induced thrombocytopenia. Here the advantage of having these binaries and image components as part of a MPPC is evident, because the processor will be examining the images of the motion picture for other causes of the fall in platelet count which may include cascades indicating TTP as will be discussed and/or occult hemorrhage.

One embodiment programmatically images the parallel physiologic time-series to render a relational pyramid of data with the top of the pyramid representing data at the highest level of analysis and abstraction while data moves down through layers of analysis, the bottom layer being the raw data streams. The healthcare worker may investigate the pyramid in the following ways to name a few:
 1) Drilldown—the care worker may navigate into the details of the data and the rationale of the analysis (i.e., both the conditions that exist and the rules by which the analysis has arrived at its conclusion)
 2) Aspects—viewports into the system which emphasize certain elements/conditions and de-emphasize (and/or filter out) other elements/conditions These two examples above may be used together allowing the healthcare worker to navigate through the relational pyramid vertically (drilldown through levels of analysis) and horizontally (through filters/aspects).

In one embodiment the relational pyramid may be manipulated by the healthcare worker and/or researcher to consider hypothetical scenarios or scenarios based on the rejection of certain test results or events which may be considered in error, anomalous or otherwise inaccurate. Alternate pyramids may be stored in whole or as differential images. Alternate pyramids may be compared against the working pyramid to understand the results of the altered data.

In one embodiment, the processor 304 will automatically consider alternate pyramids under certain conditions—such as the existence of perturbation for which no precursors may be identified. The sudden existence of perturbation or of divergence may, by considering the range of possible precursors, suggest anomalous conditions: inaccurate diagnosis, faulty monitoring equipment, labeling mistakes, the failure of a patient to take medication as prescribed, to name a few.

According to one aspect, the values and/or patterns of the blood tests such as the inflammatory mediators is/are compared to the image(s) of physiologic perturbation or to the pattern(s) or values of at least one physiologic parameter, such as the pulse rate, respiration rate, and/or ventilation oximetry index to name a few. Upon the detection of an apparent relationship, the processor may automatically order a sufficing number of sequential blood tests to confirm that the pattern of the parameter is convergent with the pattern of the blood test thereby providing strong supporting evidence, reinforcing redundant evidence, that the physiologic parameter and the mediator have a common physiologic failure based linkage, such as the failure of sepsis for example. One embodiment extends that analysis to incorporate specialized inflammatory mediators into the moving picture of failure so that comprehensive comparison of the marker or indicator to the image of the physiologic parameters and treatment is provided.

Figure 4:
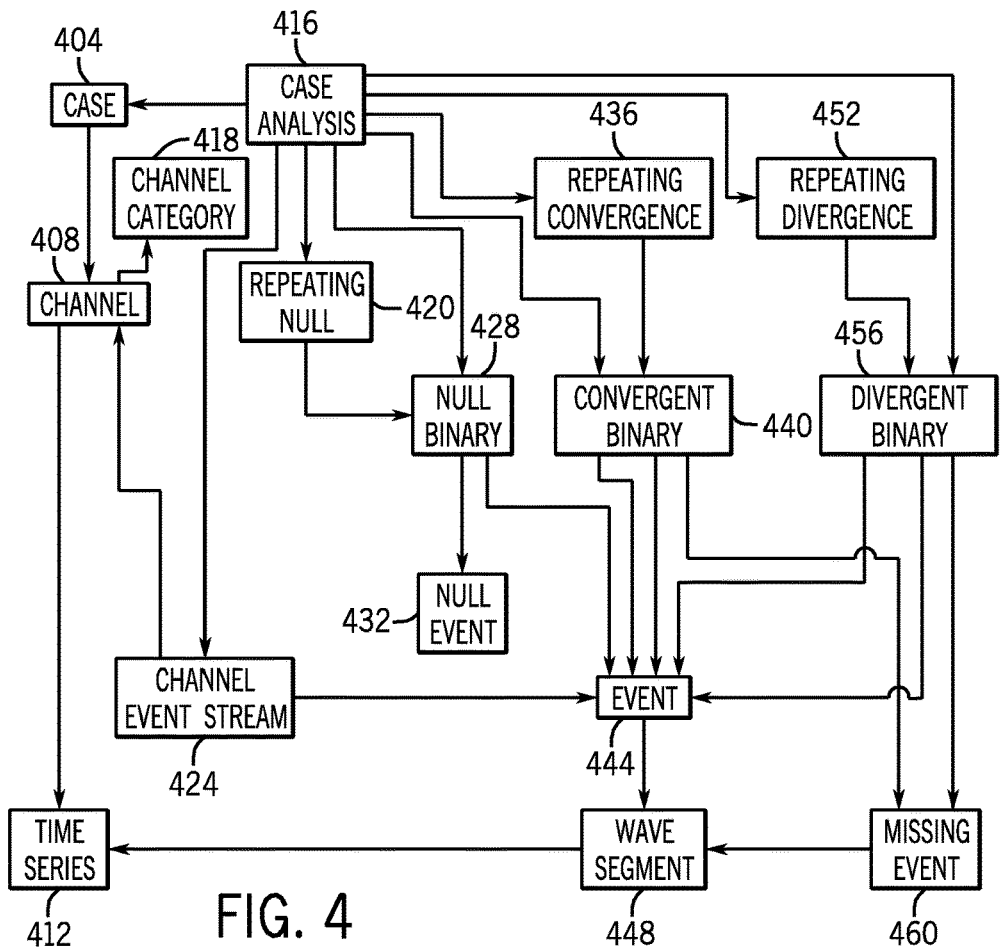
FIG. 4 is an exemplary UML Static Diagram of the primary classes within one embodiment of a relational binary processor.

FIG. 4 shows a UML Static Diagram of one embodiment of the relational binary processor 348, which defines relational binaries to thereby organize the complexity of the electronic medical record for the timely detection of failure image components. According to this embodiment a relational binary is defined by first detecting an alpha event object, which is defined in terms of its channel (e.g., oximetry) and its characteristics (e.g. slope, magnitude, duration). Then the companion (relational) beta event object is defined, again in terms of its channel, (e.g., pulse or oximetry) and its characteristics (e.g. slope, magnitude, duration) including the spatial and/or temporal relationships to the alpha event. In other words, the beta event may also be a specified as function of the magnitude, slope, timing, or other relationships of the alpha event. Alternatively or in combination the beta event may be identified as a being between two values each of which may be a function of the magnitude of the alpha event.

The actual relationship between the alpha and beta events, which comprise the object binaries, is not defined by cause and effect (which may not be known with complete certainty) but is rather defined by the pattern relationship such as a temporal, spatial, and/or frequency relationship of the events, or simply by their prior designation as a relational pair. For example, the actual relationship between the alpha and beta events comprising a given relational binary could be a cause and effect, two effects resulting from an unmonitored cause, a relationship between two monitoring technologies measuring the same physiological phenomenon, an expected compensatory response, or a pathologic response, to name a few. One object is to identify the pattern relationship of aggregate objects that include a plurality of relational binaries so that the actual relationships may be defined.

An alpha event is defined as a perturbation, which is defined in terms of its channel (e.g., oximetry) and its characteristics (e.g., a slope, magnitude, duration, and/or threshold breach). A beta event may be defined as an expected response event, defined again in terms of its channel (e.g., pulse or oximetry) and like the alpha event, in terms of its characteristics (e.g., slope, magnitude, duration). In addition, the beta event may also be defined by the spatial and/or temporal relationships to the alpha event or a component or portion of the alpha event. For example, when the beta event is an expected response event, the beta event may be specified as function of the magnitude, slope, timing, or other relationships of the alpha event. Alternatively, in another example, the expected response event may be identified as a being between two values each of which are a function of the magnitude of the perturbation event. The alpha event and/or the beta may, for example, be a perturbation event, treatment event, or a diagnostic designation event to name a few.

According to one embodiment, there are three basic relational binary types; the convergent relational binary, the divergent relational binary and a null relational binary. (Although others relational binaries may be provided). A convergent binary is an alpha event combined with an expected beta event response. If the channel of the expected response is present and uncorrupted, but the expected response is not found, then a missing event (comprising, for example, a wave segment or test result of the region of the expected response) is specified and the relational binary that includes the alpha event and the missing beta event is called a divergent binary. If the channel of the expected response is not present or the wave segment or test result is corrupted in the region of the expected response then the relational binary that includes the alpha event and the untested beta event is called a null binary.

An event may be the alpha event of a first relational binary and the beta event of second relational binary (provided the alpha event and beta events are each along different parallel channels). With some physiologic processes, relational binaries cycle or repeat with a certain pattern and this produces a special case of relational binary clusters or patterns.

In one-embodiment event characteristics may be defined in terms of modifiers defined by patient conditional values such as anthropomorphic values, age, sex, or preexisting disease, such that the presence of these modifiers (as for example provided by a rule system in combination with the event definition menu) causes a change in the event definition parameters and/or threshold values.

In one embodiment the events and/or the relational binaries (convergences and divergences) are aggregated to construct a global factorable object to derive a factorable objectified timeline. The factorable objectified timeline may be rendered graphically or provided by a nomenclature for example, which identifies the events and the time from the onset of the closest preceding event to the onset of the following event.

According to an embodiment, relational binary objects or a specific aggregation or pattern of relational binary objects may be pre-designated by the user to define a failure image component. The processor may then automatically and timely identify the occurrence of the failure image component by searching the event streams, divergence binary streams, and convergent binary streams, which are stored for each patient. In the alternative or in combination, all such streams or a portion of specific streams or a grouping of streams filtered for severity of divergence (for example) may be aggregated and rendered for periodic viewing wherein, for example, the temporal relationships of for example divergent binaries or of the occurring failure image components are easily recognized or specifically indicated.

FIG. 4 shows a convergence analysis static Model according to one embodiment including UML Static Diagram of the classes (and relationships) which the Relational binary processor uses during the processing, analyzing and synthesizing of, in this case, electronic medical record input streams. Objects created from these classes represent the identified perturbations as well as attempted identifications, which failed due to the absence of data streams. User-interfaces, reporting systems, business intelligence and data warehousing sub-systems, notification mechanisms, alarms and other human or software application interfaces access this analysis structure to aggregate, further analyze, store and/or react to the results of analysis.

In the depicted embodiment, the case 404, channel 408 and time series 412 classes represent the data streams from which the analysis may be derived. These classes may be defined as disclosed in U.S. Pat. Nos. 6,609,016 and 7,081,095 and U.S. patent application Ser. Nos. 11/431,686, 11/351,449, and 11/148,325 the specifications of each of which are incorporated by reference for all purposes in their entirety. For each case 404, one or more case analyses 416 may be constructed. A case analysis 416 is the result of a case 404 being submitted to the relational binary processor 348 with a specified binary definition set. A single case 404 may be analyzed with multiple binary definition sets resulting in one case analysis 416 per binary definition set applied.

A case analysis 416 is primarily composed of the relational binaries identified during processing. In one embodiment, the relational binaries are one of three types—convergent binary 440, divergent binary 456 and null binary 428. The case analysis 416 contains a collection of each of these pairs and may have zero of more pairs in each of those collections. As discussed, relational binaries are composed of relational events 444. The structure of the relational binary (i.e., the type of events which compose the relational binary) is defined by its type and the classification is provided to fix the structure of these relationships. In one embodiment, all relational binaries contain an alpha event, which is a true event (e.g., represents the identification of a pattern or a threshold violation, see FIG. 5). In an embodiment, the type of beta event identified makes the distinction between object binary types. For example, a convergent binary 440 represent a relational pair of events wherein the beta event has an expected relationship to the alpha event as described in the binary definition set. A relational binary may have either a true event 444 or a missing event 460 as a beta depending on what has been specified as the expected condition. If a true event 444 was specified in the relational binary definition then the associated convergent binary 440 may have a true event 444 as a beta event. If a missing event 460 was specified then the associated convergent binary 440 may have a missing event 460 as a beta event. The class structure therefore allows for zero or one event 444 and zero or one missing event 460. In a presently preferred embodiment a convergent binary 440 may not contain two beta events.

Divergent binaries 456 represent a relational pair of events identified in a relationship that contradicts the expected relationship as described in the binary definition set. Therefore a divergent binary 456 may have either a true event 444 or a missing event 460 as a beta depending on what has been specified as the expected condition. If a true event 444 was specified in the binary definition then the associated divergent binary 456 may have a missing event 460 as a beta event. If a missing event 460 was specified then the associated divergent binary 456 may have a true event 444 as a beta event. The class structure therefore allows for zero or one event 444 and zero or one missing event 460. According to one embodiment, a divergent binary 456 may not contain two beta events.

Null binaries 428 represent the existence of a condition in which an alpha event was identified but the data stream from which the expected beta event is to be derived is unavailable to the relational binary processor 348. Events 444 may be isolated (e.g., not part of any identified relational pair) or part of one or more binary. The channel event stream 424 provides an aggregation of events 444 ordered by time and separated by channel 408. A true event 444 is a wave segment 448 (e.g. inherits wave segment) while a missing event 460 is associated with a wave segment 448 that represents the section of the channel 408 that was searched for the event described as expected in the binary definition set. Null events 432 are not associated with wave segments 448 because the channel 408 to which they would have been attached or the relevant section of that channel 408 is unavailable or corrupted. The relational binary processor 348 will convert null binaries 428 to convergent 440 or divergent 456 binaries as channels 408 of data become available.

The analysis contains aggregations of binaries, which repeat (e.g., cycling reciprocations) in three aggregation classes: repeating convergence 436, repeating divergence 452 and repeating null 420. To further clarify this structure it may be useful to describe the order of operation within an exemplary embodiment of the relational binary processor as it constructs the analysis according to one embodiment.

1. Each channel 408 in turn is iterated through and named events 492 and threshold violations 484 (Events which may be identified without reference to relational pairs) are identified and placed into channel event streams 424
2. The channel streams 424 are iterated through to match any identified events 444 with candidate alpha events (as defined in the specified binary definition set). A single event 444 may match any number of alpha event definitions and each one is considered a candidate alpha event.
   a. For each candidate alpha event, the specified search region is examined for the expected beta event
   i. If the channel 408 in which the expected beta event is unavailable or corrupted
   1. A null binary 428 is created (along with its associated null event 432)
   2. The conditions are examined to determine whether a Repeating Null 420 should be created or appended to
   ii. If the expected condition is found
   1. A convergent binary 440 is created
   2. If a relational event 488 was identified in the process it is created and added to the channel event stream 424
   3. The conditions are examined to determine whether a repeating convergence 436 should be created or appended to
   iii. If the expected condition is not found
   1. A divergent binary 456 is created
   2. If a relational event 488 was identified in the process it is created and added to the channel event stream 424
   3. The conditions are examined to determine whether a repeating divergence 452 should be created or appended to
3. Failure image components and aggregate failure image components are identified (See Below)

Figure 5:
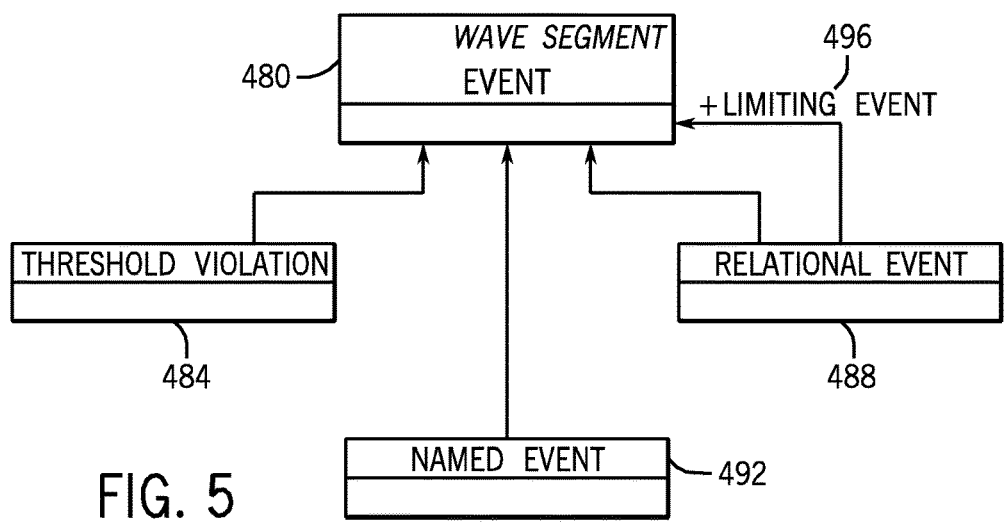
FIG. 5 is an exemplary UML Static Diagram of a subset of the relational binary processor specifically expanding the definition of the event type.

FIG. 5 shows an event type static model. According to an embodiment, events may be represented as one of three types: threshold violation 484, named event 492, and relational event 488. Threshold violations 484 represent the existence of a breach of some specified, calculated or derived limit within an associated channel 408. Named events 492 and relational events 488 represent an identified unipolar pattern within a channel 408. Named events 492 differ from relational events 488 in that the parameters with which the pattern is identified is not a function of elements of an associated event (e.g. a limiting event 496). Limiting events 496 within the context of a convergent binary 440 are the alpha event of the related relational binary.

A limiting event 496 may be either a threshold violation 484 or a named event 492, but, in one embodiment, not a relational event 488. In an embodiment limiting events 496 may be relational events 488 and the relational binary processor employs recursive algorithms to determine a comprehensive set of events. Threshold violations 484 and named events 492 may be isolated events (e.g. identified independent of a relational binary). Alpha events of a relational binary may be either a threshold violation 484 or a named event 492 but, in this embodiment, not a relational event 488. In an embodiment this rule is relaxed to provide the ability to produce a relational cascade. In an embodiment, alpha events may be relational events and the relational binary processor may employ recursive algorithms to determine a comprehensive set of events.

Figure 6:
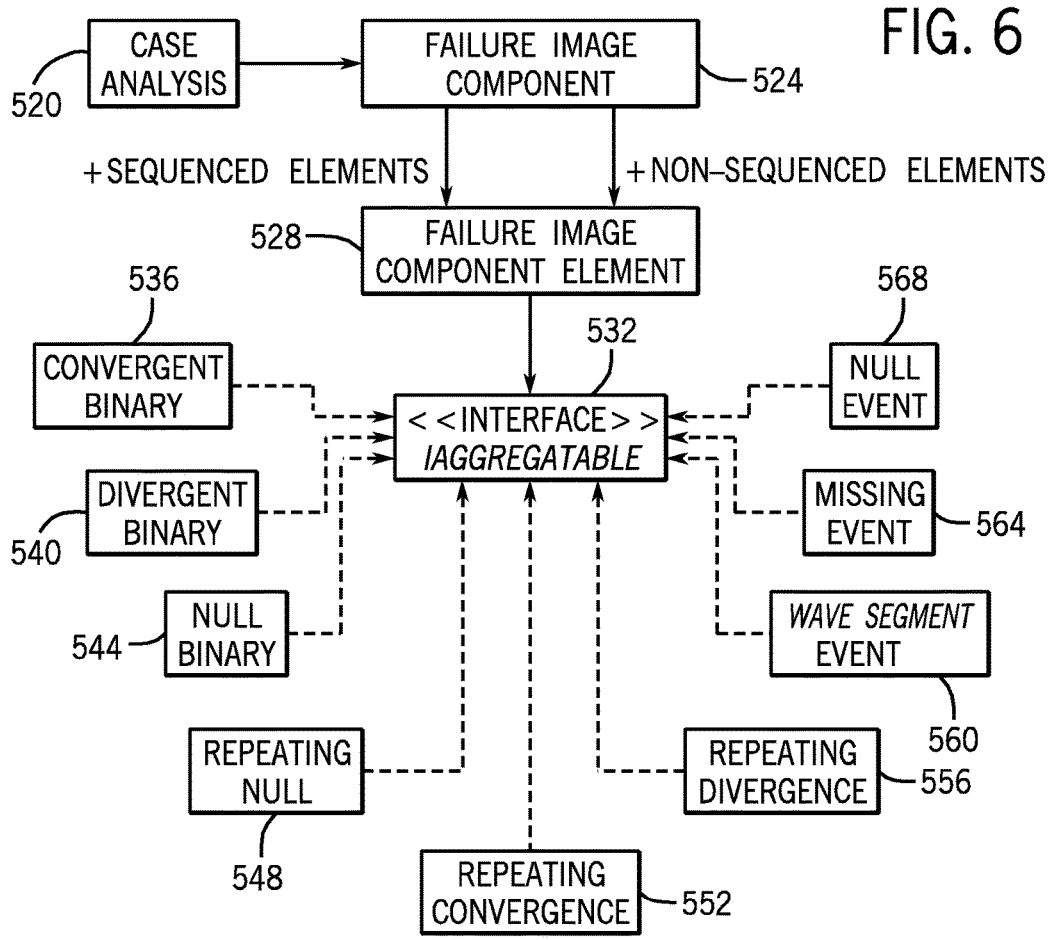
FIG. 6 is an exemplary UML Static Diagram of the primary classes within the patient safety processor.

FIG. 6 shows an aggregate failure image component static model, which provides further clarification to the presently preferred embodiment of the patient safety processor. The aggregate failure image is one type image which will be searched for. After the relational binaries are identified, the relational binary processor 348 may aggregate these identified pairs into aggregate failure image component objects, which represent the identification of patterns of events and binaries. The aggregate failure image components 524 are created with respect to a failure image component definition set. A failure image component definition set is associated with a single binary definition set, but multiple failure image component definition sets may be created for a binary definition set.

An aggregate failure image component 524 has two collections of failure image component elements 528. The first is a set of failure image component elements 528 that was identified in a specific sequence. The second represents failure image component elements 528 that simply fell within the specified search window (e.g., existence, not sequence is sufficient for aggregation). Aggregatable 532 is one embodiment of a lightweight interface, which allows the analysis objects (536, 540, 544, 548, 552, 556, 560, 564, 568) to participate in the aggregation. The analysis objects include convergent binaries 536, divergent binaries 540, null binaries 544, repeating nulls 548, repeating convergences 552, repeating divergences 556, events 560, missing events 564 and null events 568 may all participate in an aggregate failure image component 528.

Figure 7:
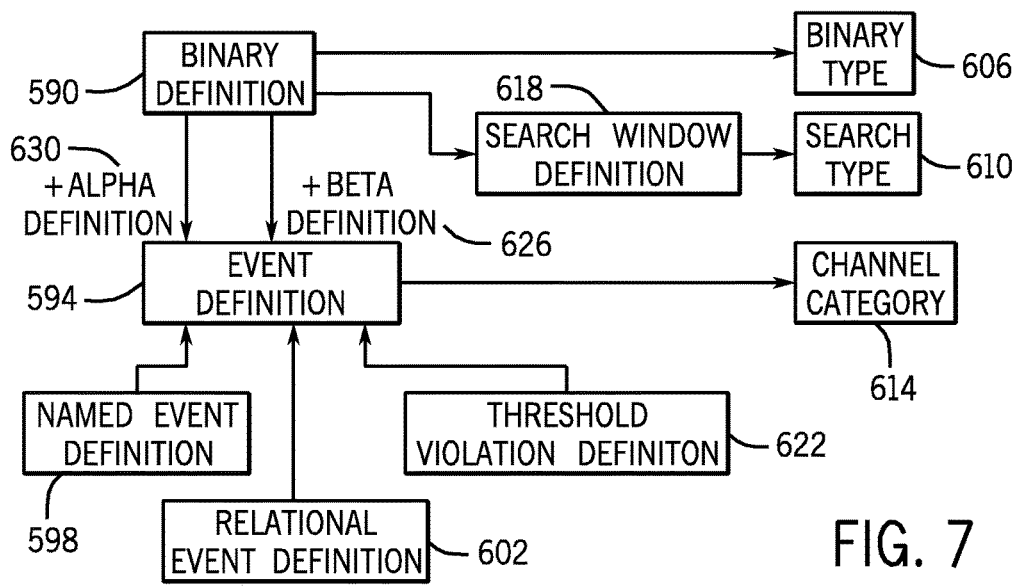
FIG. 7 is an exemplary UML Static Diagram of the primary classes within the binary definition set.

FIG. 7 shows a binary definition set static model. The binary definition set model represents the objects that are part of the binary definition sets used by the relational binary processor 348 to create the convergence analysis. A binary definition 590 represents the parameters used to identify a relational binary. A binary definition 590 is made up of four key elements—the binary type 606, the search window definition 618 and the definitions of the alpha 630 and expected beta events 594.

Figure 8:
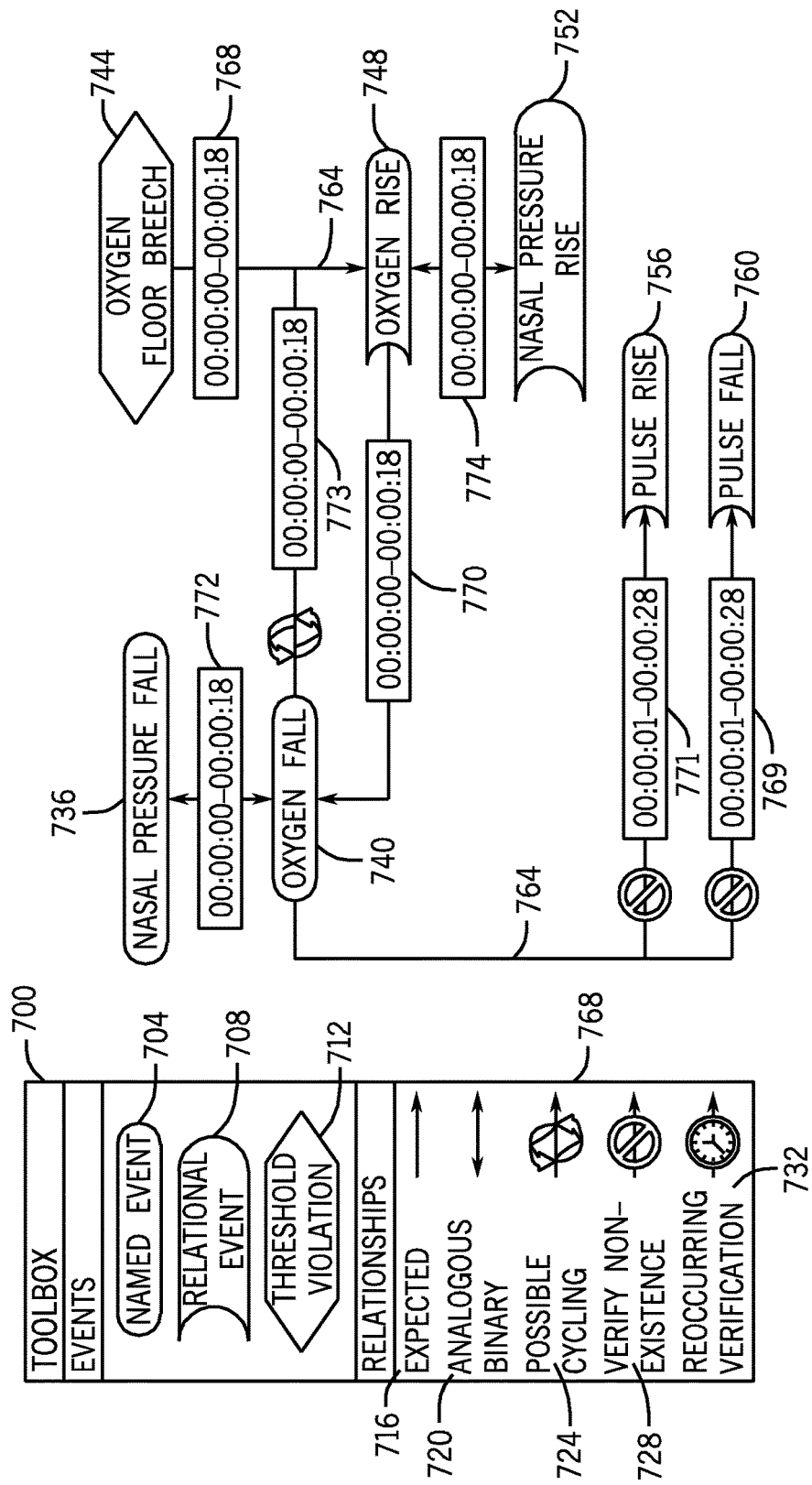
FIG. 8 is an exemplary UML Static Diagram of the primary classes within the Failure image component Definition Set.

FIG. 8 shows an embodiment of a convergence editor, which provides the ability for the creation, and modification of a binary definition set, which may be used by the relational binary processor to create the convergence analysis. A binary definition set may be represented as a convergence model—a visual representation of the object instances shown in FIG. 7. The user interface includes a design surface 764 and an element toolbox 700, which allows for the drag-and-drop creation and manipulation of a subset of the convergence model called a binary diagram. The aggregation of all binary diagrams created with a single name constitutes the entire convergence model and may be persisted as a binary definition set in the relational database or in an XML file to name a few. Breaking a convergence model into binary diagrams allows for multiple views into the model. These views are not mutually exclusive (i.e., the same binary definition may be represented in multiple diagrams) and therefore provide views into model at various levels of complexity and points of reference.

The box on the left is the convergence element toolbox 700 which presents the visual elements which may be added to the design surface and therefore to the binary diagram. The shapes represent events that may be added. The three event types available correspond with the event definition classes in FIG. 7: named event 598, relational event 602 and threshold violation 622. The relationships 768 section of the toolbox 700 presents a set of lines, which may be used to connect two events to create a relational binary. The line chosen determines the binary types 606. binary types include: expected 716, analogous binary 720, possible cycling 724, verify non-existence 728, reoccurring verification 732. The visual icon attached to the line may cue the user to its type. The binary type 606 determines the type and frequency of search that may occur when the candidate alpha event is identified. For example, the reoccurring verification type 732 may generate multiple binaries for a single candidate alpha event because it directs the relational binary processor to search for the expected event with a specified frequency, generating binaries at each interval. Some binary types may be used in combination (e.g., reoccurring verification 732 and verify non-existence 724). Each relationship added to the design surface 764 must have at least one time interval provided (e.g., 768) which represents the search window definition 618 for the binary definition 590. Each relationship may be directional. The line includes an arrow end-style on the end that represents the beta definition 626. The end without an arrow represents the alpha definition 630.

Each pair of events, which has a connecting relationship, represents a single binary definition 590. In the above figure, the following seven binaries:
1. An analogous binary between nasal pressure fall and oxygen fall (736, 772, 740)
2. A possible cycling binary between oxygen fall and oxygen rise (740, 773, 748)
3. An expected relationship between oxygen floor breech threshold violation and oxygen rise (744, 768, 748)
4. An expected relationship between oxygen rise and oxygen fall (748, 770, 740)
5. An analogous binary between oxygen rise and nasal pressure rise (748, 774, 752)
6. A verify non-existence binary between oxygen fall and pulse rise (740, 771, 756)
7. A verify non-existence binary between oxygen fall and pulse fall (740, 769, 760)

This diagram does not represent all of the relationships of each of these events. It is an example of a subset view into the overall convergence model with a focus on sleep apnea. Relationships and elements may be removed from this diagram without removing them from the entire model (i.e., the editor distinguishes between "Remove" which removes the element from the diagram but not the model and "Delete" which removes the element from the diagram and the model [including all other diagrams]). A diagram may be constructed that shows all of the events and relationships, but it would likely be so large and complex as to be unreadable.

The editor will check the diagram for validity before persistence or at the user's request. For example, a relationship without a beta event would invalidate a diagram. An invalid diagram may invalidate the convergence model. It is preferred that a convergence model cannot be persisted into a binary definition set. The editor allows for an invalid state to provide flexibility during diagram construction. Further, if the target binary definition set is associated with failure image component definition sets that are available to the editor, the editor may warn of conflicts with associated models by changes to the diagram. Depending on editor settings, these changes are disallowed, or the changes may be propagated into the failure image component.

Each diagram element may be manipulated in a more detailed way through property editors associated with the element type. The property editors provide access to all editable properties of the associated definition objects such that the editor is sufficient to construct a complete binary definition set. The editor provides for adding text, notes, lines and other visual elements to the diagram to increase human readability and to communicate between users. These additional visual elements have no affect on the binary definition set.

This structure may be understood within the context of the user interface modeled in FIG. 7 that may be used to visually construct the binary definition set. Specifically, FIG. 7 depicts a binary diagram within the convergence editor which pertains to the monitoring of sleep apnea. Each pair of events (e.g., 744, 748), which has a connecting relationship (e.g., 754), represents a single binary definition 590. The connecting line between the two events represents the binary type 606. Binary types may include: expected 716, analogous binary 720, possible cycling 724, verify non-existence 728, and reoccurring verification 732. The binary type 606 determines the type and frequency of search that may occur when the candidate alpha event is identified. For example, the reoccurring verification 732 type may generate multiple relational binaries for a single candidate alpha event because it directs the relational binary processor to search for the expected event with a specified frequency, generating relational binaries at each interval. In an embodiment, some binary types may be used in combination (e.g., reoccurring verification 732 and verify non-existence 728). The box containing a pair of time offsets 768 represents the search window definition 618. This definition contains the start and end time offsets from the end point of the alpha event for which the beta event should be searched in the target beta channel. Finally the shapes represent the alpha and beta event definitions. These definitions provide the parameters with which the relational binary processor may search the identified wave segment for the existence of a unipolar pattern (i.e., meeting the criteria defined by named event definition 598 or relational event definition 602 or threshold violation (i.e., meeting the criteria defined by threshold violation definition 622).

Figure 9:
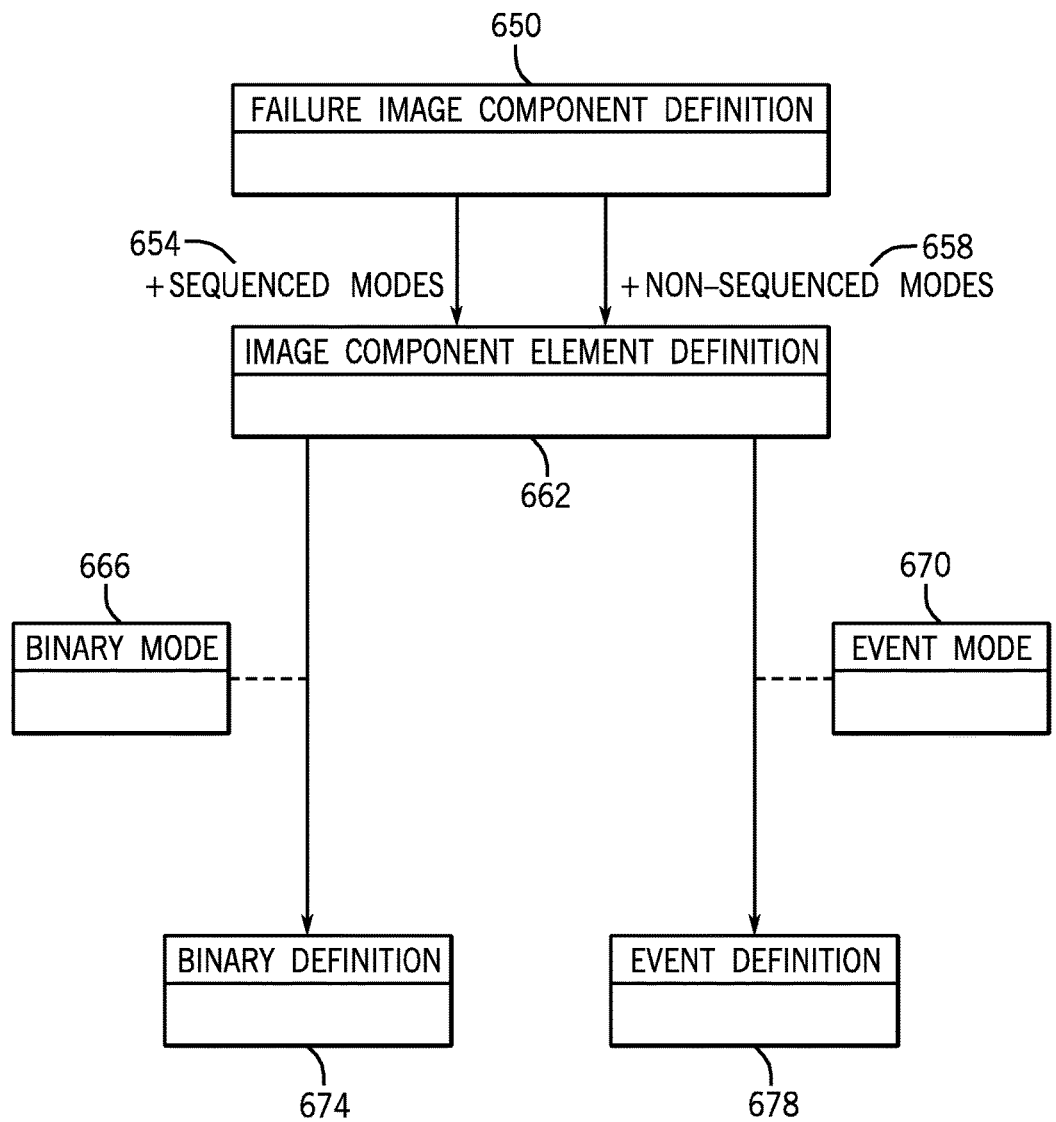
FIG. 9 is an exemplary user interface model of the convergence editor that depicts a sleep apnea binary diagram.
Figure 10:
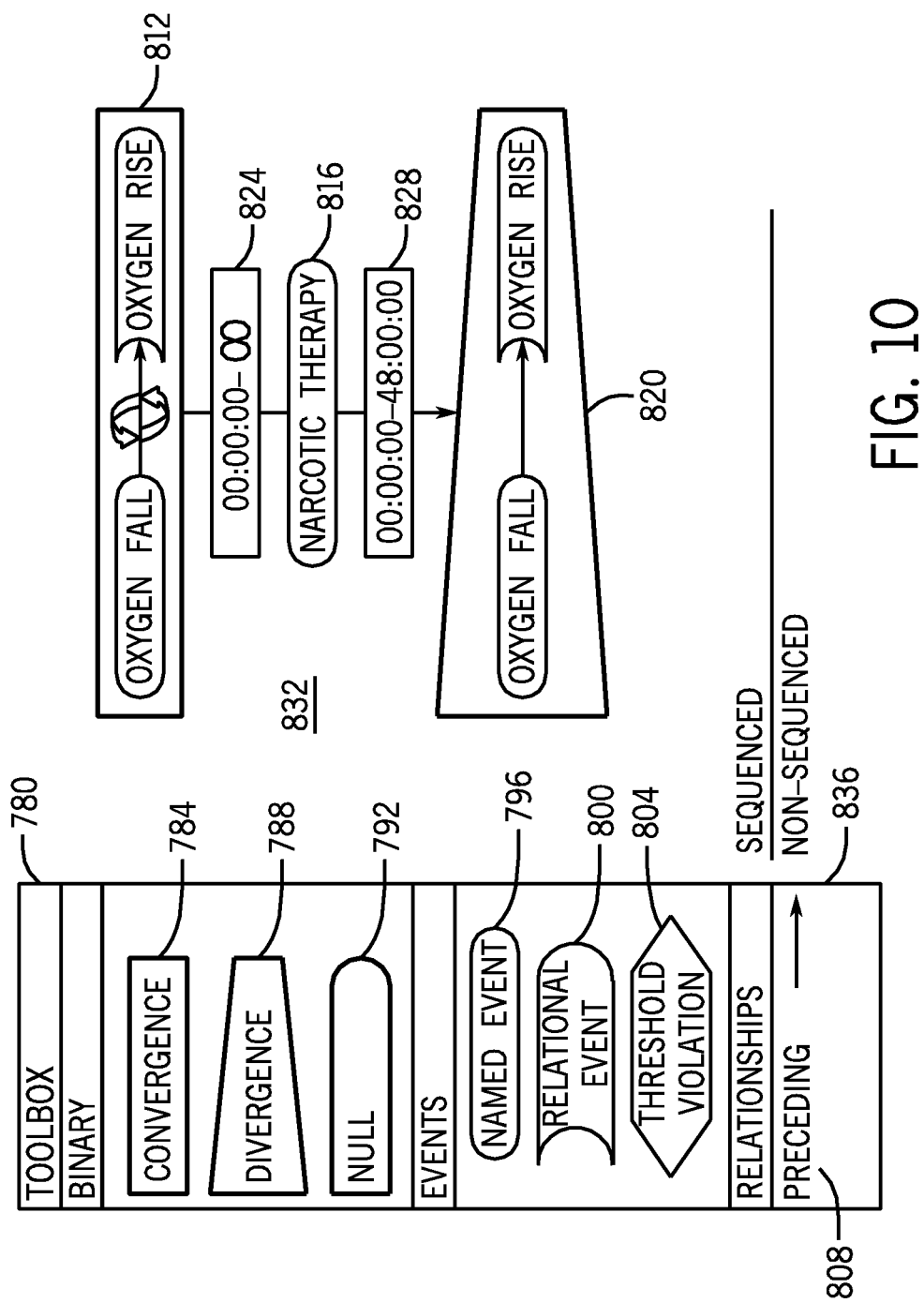
FIG. 10 is an exemplary user interface model of the aggregate failure image component editor that depicts a failure image component diagram associated with narcotic-induced ventilation instability.

FIG. 9 shows a failure image component definition static model. The failure image component model represents the classes that are part of the failure image component definition sets used by the failure image processor to identify and create aggregate failure image components. A failure image component definition represents the set of element definitions and their relationships, which allow the failure image processor to determine whether the pattern of elements meets the criteria of the specified failure image component. FIG. 10 shows an embodiment of the aggregate failure image component editor that provides the ability for the creation and modification of a failure image component definition set, which will be used by the failure image processor, in coordination with a binary definition set, to create a convergence analysis. A failure image component definition set may be represented as a failure image component—a visual representation of the object instances shown in FIG. 9. The user interface includes a design surface 832 and an element toolbox 780, which allows for the drag-and-drop creation and manipulation of a subset of the failure image component called a failure image component diagram. The aggregation of all failure image component diagrams created with a single name constitutes the entire failure image component and may be persisted as a failure image component definition set in the relational database or in an XML file to name a few. As with the convergence model, failure diagrams are views into the model that provide visualizations at various levels of complexity and points of reference.

A failure image component definition set is associated with, and dependent upon, a specified binary definition set. A failure image component definition set, and therefore a failure image component and all its corresponding diagrams, cannot be created without the specification of a binary definition set. Further the specified binary definition set provides and limits the events and binaries that may be used to create the failure image component diagrams.

This structure may be understood within the context of the user interface in FIG. 10. Each diagram represents a single failure image component definition 650. In this embodiment, a failure image component element definition 662 may either be a binary definition 674 or an event definition 678 (but in one embodiment, may not be both). These failure image component element definitions 662 represent the existence of a specific event or relational binary. If a specific sequence of elements is defined to identify the failure image component then the sequence is specified with connectors and time offsets (e.g., 812, 824, 816, 828, and 820). Each shape container (a shape that contains other shapes) represents a failure image component element definition 662. A failure image component element definition 662 includes both a binary definition 674 and a binary mode. The binary mode 666 indicates the type of binary that must be created by the binary definition 674 within the analysis (e.g., convergence, divergence or null). Within FIG. 10, the mode is specified by selecting the binary container (e.g., 784, 788, and 792) from the toolbox 780. An isolated shape without internal shapes represents an event failure image component element 678. An event failure image component element 678 includes both an event definition 678 and an event mode 670. The event mode 670 indicates the type of event that must be created by the event definition 678 within the analysis (e.g., event, missing event or null event).

Failure image component element toolbox 780 in FIG. 10 presents the visual elements that may be added to the design surface 832 and therefore to the failure image component diagram. The large bold-lined container shapes (784, 788, and 792) represent failure image component elements that refer to a binary while the smaller shapes (796, 800, 804) represent failure image component elements that refer to events (isolated or part of a binary). The three binary element types available correspond with the available binary modes 666: Convergence, divergence and null. Each binary dropped on the surface may subsequently lead to the selection of a binary definition 674 from the associated binary definition set. The design surface is split into two sections—sequenced and non-sequenced. Elements in the sequenced area correspond to the sequenced mode aggregation 654 in FIG. 9. These elements involve a relationship in time and therefore a relationship may be specified between them (e.g., 824). The relationships section 836 of the toolbox presents a set of lines, which may be used to connect two failure image component elements (either binaries or events) as part of the overall aggregate. Each relationship added to the design surface must have a time interval provided (e.g., 828) which represents the search window definition associated within the sequenced mode aggregation 654. Each relationship is directional indicating precedence in the sequence 654.

Zero or more sequences may be specified, but if an element is placed in the sequenced section it is defined as part of a sequence. Elements placed in the non-sequenced section cannot have relationships. Only existence is specified within the overall time-frame specified for the failure image component. The failure image component diagram differs from the binary diagram in that the diagram itself represents an entity—the failure image component definition 650—and is not simply a collection of other entities (e.g., binaries in the case of the binary editor). Removing elements changes the definition of when a failure image component will be identified. All elements added to the failure image component diagram represent an "and" relationship for identification purposes (i.e., all elements and sequences must exist for the failure image component to be identified). In one embodiment, to create "Or" scenarios, multiple failure image component diagrams are created with variation representing the "or" combinations. The editor may check the diagram for validity before persistence or at the user's request. The editor allows for an invalid state to provide flexibility during diagram construction.

Each diagram element may be manipulated in a more detailed way through property editors associated with the element type. The property editors provide access to all editable properties of the associated definition objects such that the editor is sufficient to construct a complete failure image component definition set. The editor provides for adding text, notes, lines and other visual elements to the diagram to increase human readability and to communicate between users. These additional visual elopements have no affect on the failure image component definition set.

Figure 11:
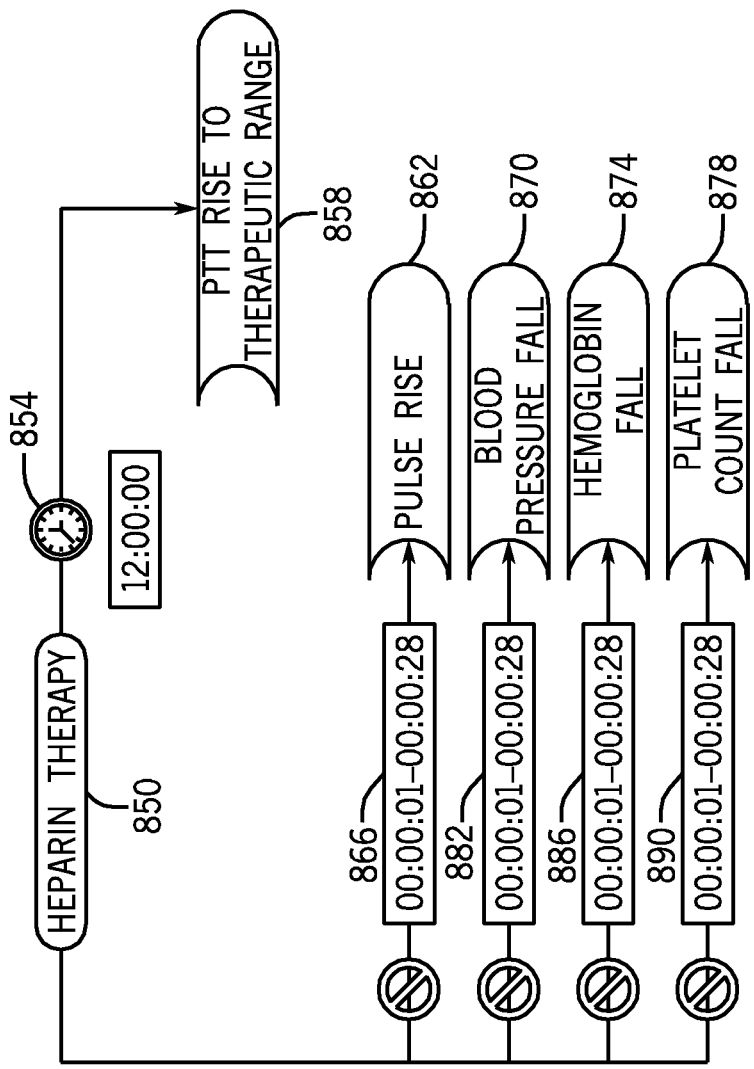
FIG. 11 is an exemplary user interface model of the convergence editor that depicts a heparin therapy binary diagram.

FIG. 11 provides an example of a binary diagram referring to heparin therapy in which the following binary definitions are specified:
 1. A reoccurring verification binary 854 between heparin therapy 850 and ptt rise to therapeutic range 858.
 2. A verify non-existence binary 866 between heparin therapy 850 and pulse rise 862.
 3. A verify non-existence binary 882 between heparin therapy 850 and blood pressure fall 870.
 4. A verify non-existence binary 886 between heparin therapy 850 and hemoglobin fall 874.
 5. A verify non-existence binary 890 between heparin therapy 850 and platelet count fall 878.

Figure 12:
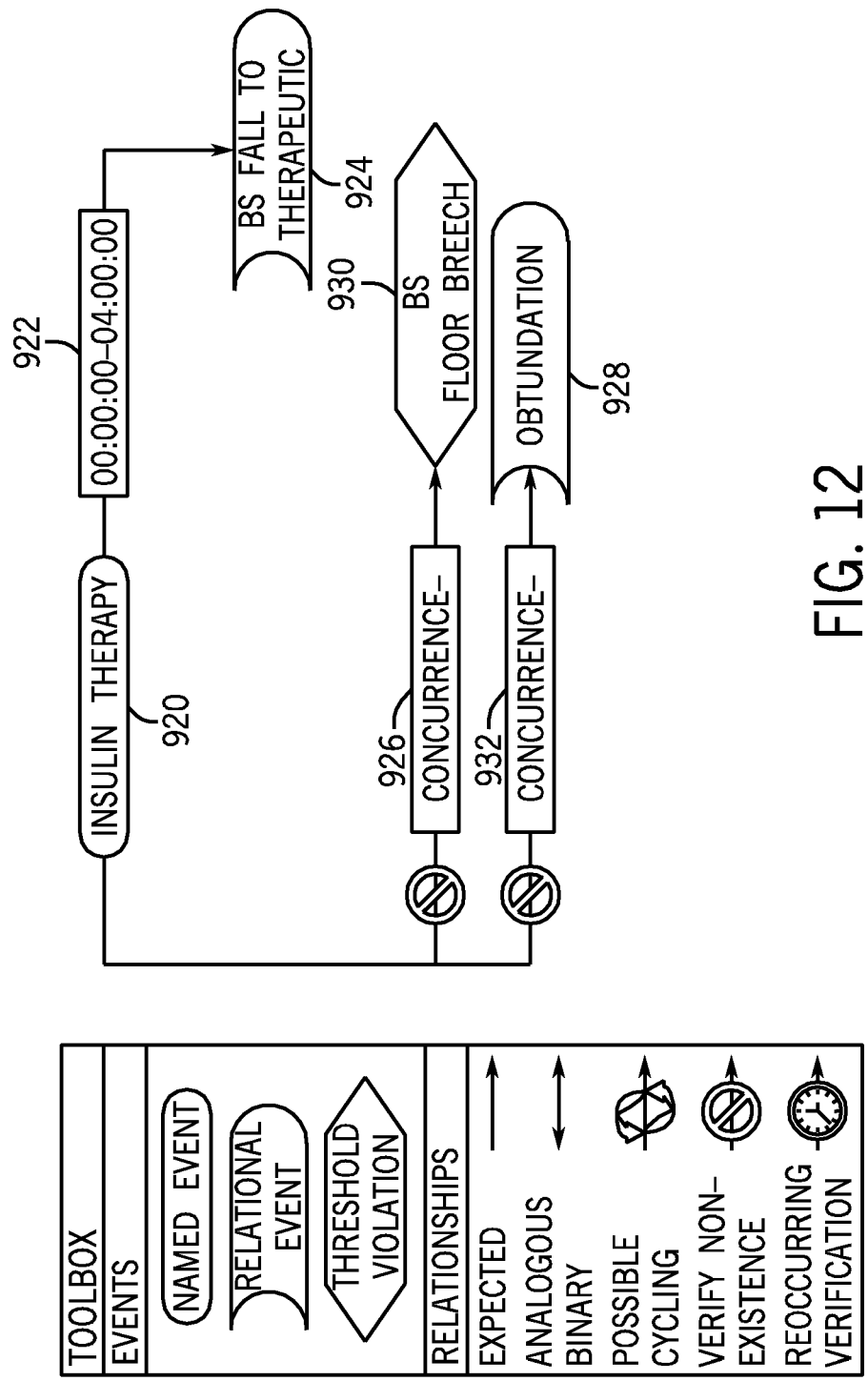
FIG. 12 is an exemplary user interface model of the convergence editor that depicts an insulin therapy binary diagram.

FIG. 12 provides an additional example of a binary diagram referring to insulin therapy in which the following binary definitions are specified:
 1. An expected binary 922 between insulin therapy 920 and blood sugar fall 924 to therapeutic range.
 2. A verify non-existence binary 926 between insulin therapy 920 and blood sugar breech 930.
 3. A verify non-existence binary 926 between insulin therapy 920 and confusion 928.

Figure 13:
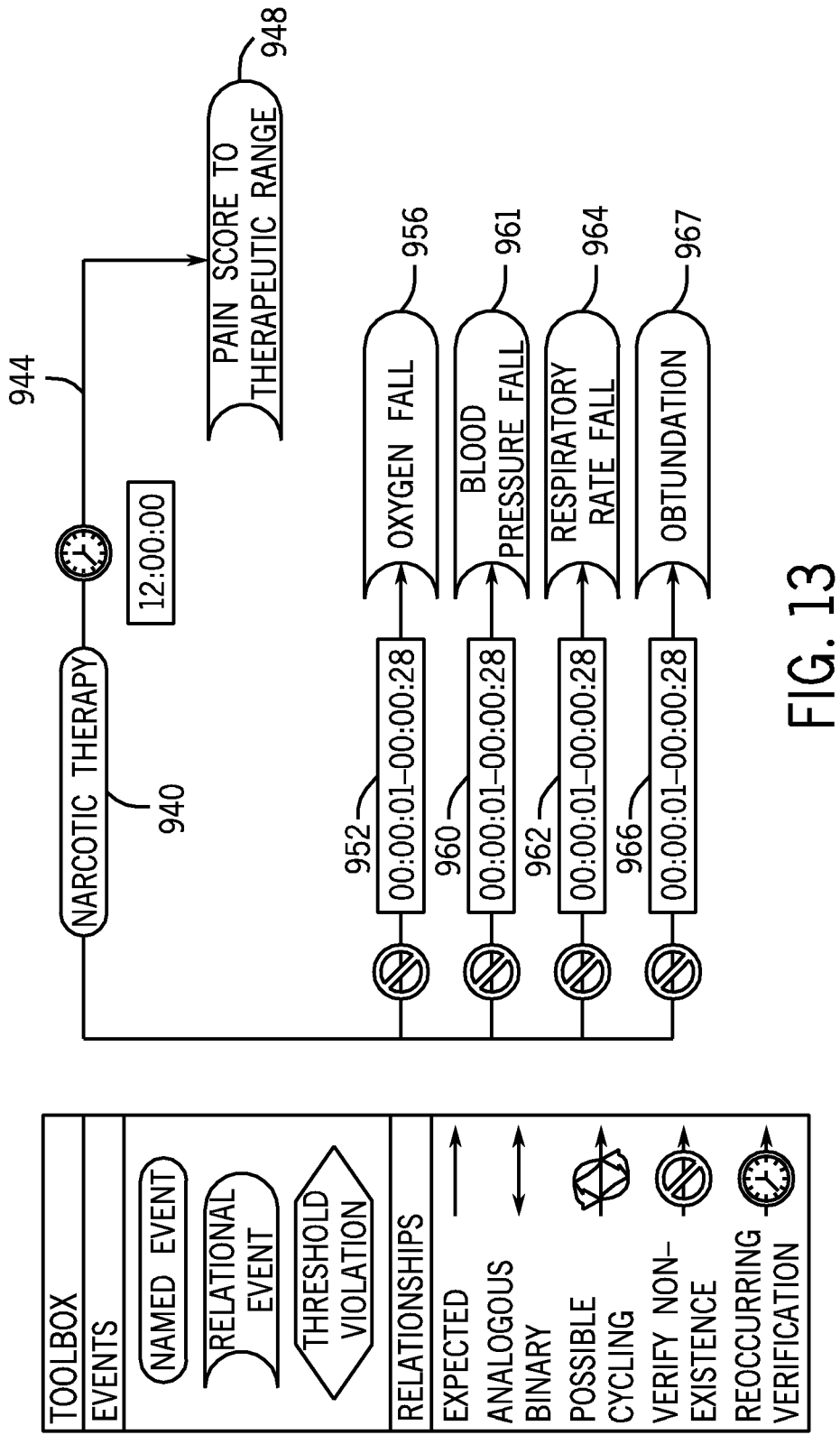
FIG. 13 is an exemplary user interface model of the convergence editor that depicts a narcotic therapy binary diagram.

FIG. 13 provides an additional example of a binary diagram referring to narcotic therapy in which the following binary definitions are specified:
 1. A reoccurring verification binary 944 between narcotic therapy 940 and pain score fall to therapeutic range (948)
 2. A verify non-existence binary 952 between narcotic therapy 940 and oxygen fall 956.

3. A verify non-existence binary 960 between narcotic therapy 940 and blood pressure fall 961.
4. A verify non-existence binary 962 between narcotic therapy 940 and respiratory rate fall 964.
5. A verify non-existence binary 966 between narcotic therapy 940 and confusion 967.

Figure 14:
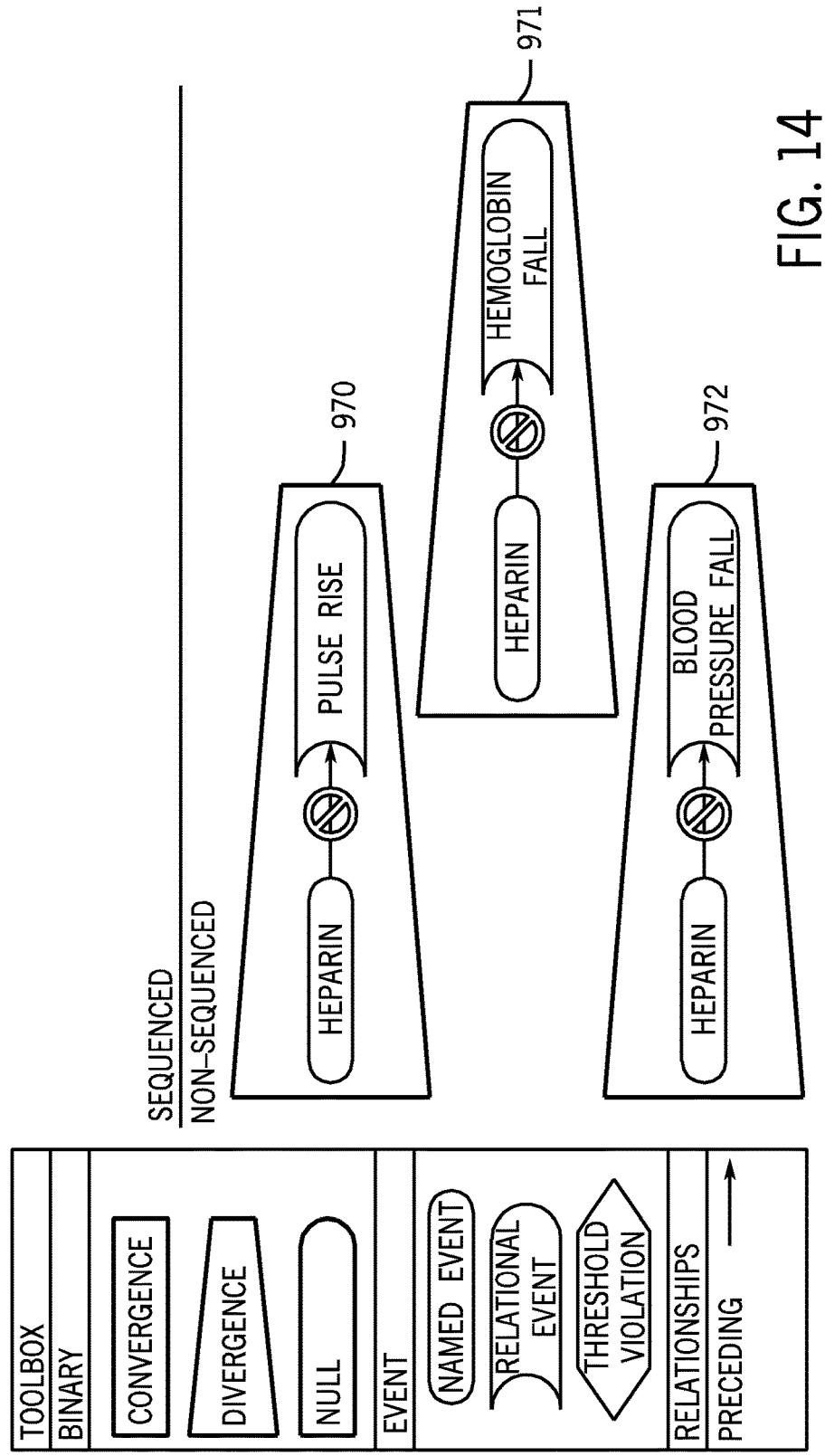
FIG. 14 is an exemplary user interface model of the aggregate failure image component editor that depicts a failure image component diagram associated with heparin-induced hemorrhage.

FIG. 14 provides an additional example of the failure image component editor in which three non-sequenced binaries (970, 971, 972) are defined as sufficient to identify possible heparin-induced hemorrhage.

Figure 15A:
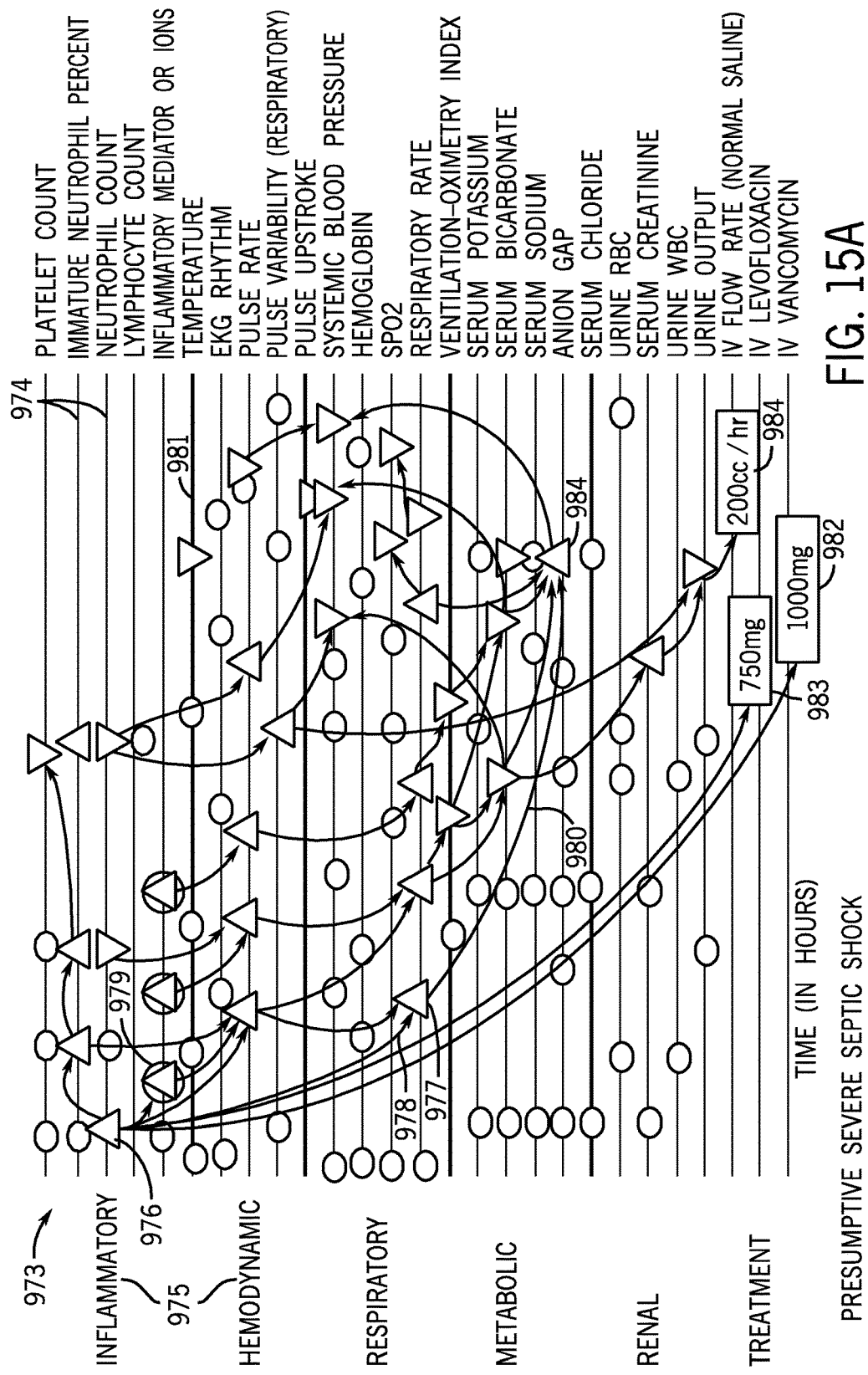
FIG. 15A is a failure image frame that includes a plurality of timelines organized into groupings showing an expanding cascade of evolving death due to septic shock.

FIG. 15A shows a failure image frame 973 of a patient's physiologic system and care and demonstrates one exemplary image according to one embodiment as generated by the failure image processor. The image shown is indicative of dynamic progression from an image suggestive of stability to an image suggestive of a failure cascade of septic shock. This is the one of image for which the patient safety processor is deployed as a "search engine for pathophysiologic cascades" may continuously search when deployed into use with a patient. The image displays objectified events that met criteria as up and down arrows indicating whether they are rise events or fall events respectively. Minor time series variations (such as detected minor rises or falls typical of signal noise, which fail to meet criteria by the objectification processor as events) are represented on each time-line as open circles along parallel time lines. (The visualization of such variations may be turned on or off as desired). The detected events are combined with other events to form binaries which are then combined to produce an image of relational patterns that include aggregate binaries and individual events defining the dynamic state of the patient's physiological system and of the medical care applied to the physiologic system during the time interval of each respective image. Within the complete image, smaller failure images aggregate to produce the larger image of aggregate failure (in this case, of septic shock). In real time this is a motion picture image which may be shown with this rendering or with an alternative rendering, such as an actual digital motion picture of the patient within these parameters reanimated in the MPPC.

Since FIG. 15A is a late "time lapsed" frame of a MPPC that has exhibited many earlier frames, the patient safety processor output provided that confidence that the cascade image detected search engine is septic shock was high. Representations of rise events or fall events are depicted as up-arrowheads and down-arrowheads respectively on each time line 974. The timelines 974 are grouped into categories 975. The first event detected within the time interval of the image is a perturbation event—a rise event of the neutrophil count 976 shown by the upward pointing arrowhead on the neutrophil timeline. This perturbation event is combined by the relational processor to a second perturbation event—a rise in respiratory rate 977 also shown by an upward arrowhead, to generate the first relational binary 978 (combined in the figure by the arrow connecting 976 and 977). Each subsequent perturbation in the image is designated by its timeline and arrowhead. An arrowhead with a circle around it designates perturbations determined by testing automatically ordered by the patient safety processor in response to the detection of a particular image. In an example the rise event in inflammatory mediators or indicators 979 was ordered by the patient safety processor to better define the inflammation portion of the image which was somewhat obscured because the early images demonstrated a rise in neutrophil count, a rise in pulse, and a rise in respiration rate but with a normal temperature. Since this ambiguous image must be better defined to decide care, testing for inflammatory mediators/indicators is automatically ordered by the processor to better complete the image.

Using these basic designations the image of FIG. 15A reveals a clear image frame (a time lapsed snap shot) detected by searching of an MPPC that includes perturbations of inflammation, followed by a hemodynamic perturbations, followed closely by respiratory perturbations, and then renal perturbations in an expanding and linked cascade 980. The initial rise in Neutrophil count 976, the first detected perturbation event, will have completely disappeared later in the cascade such that frames late in a failure process are best viewed with the sufficient scale to observe the onset of the cascade 980. The image shows a complete lack of any events along the temperature timeline 981. In the absence of the analysis provided by the processor 304, the lack of a fever may mislead a healthcare worker, who may think of fever as a reliable indicator for the early detection of sepsis. However, the processor 304 is programmed to recognize that it has rendered or found an incomplete image and then seeks to complete the image by ordering testing for inflammatory mediator 979. This testing serves as a "surrogate image components" for a rise in temperature thereby establishing that the entire failure image does in fact exhibit an early component of inflammation.

Two drug treatments are evident in the image, the antibiotics vancomycin 982, designated by its dose on the time line, and levofloxacin 983, similarly designated. Also a rise in IV fluids in the form of normal saline 984 is indicated. All of these treatments come late after the image has long been indicative of a high probability of sepsis. (This delay, which may be detected in real-time by the patient safety processor, suggests poor and ineffective care, which has ignored or otherwise been poorly responsive to the patient safety processor. The processor may be programmed to provide an indication of the quality of the care provided. Time lines, which include the care worker or ward may be provided so that delays may be linked to particular locations or care workers).

Figure 19:
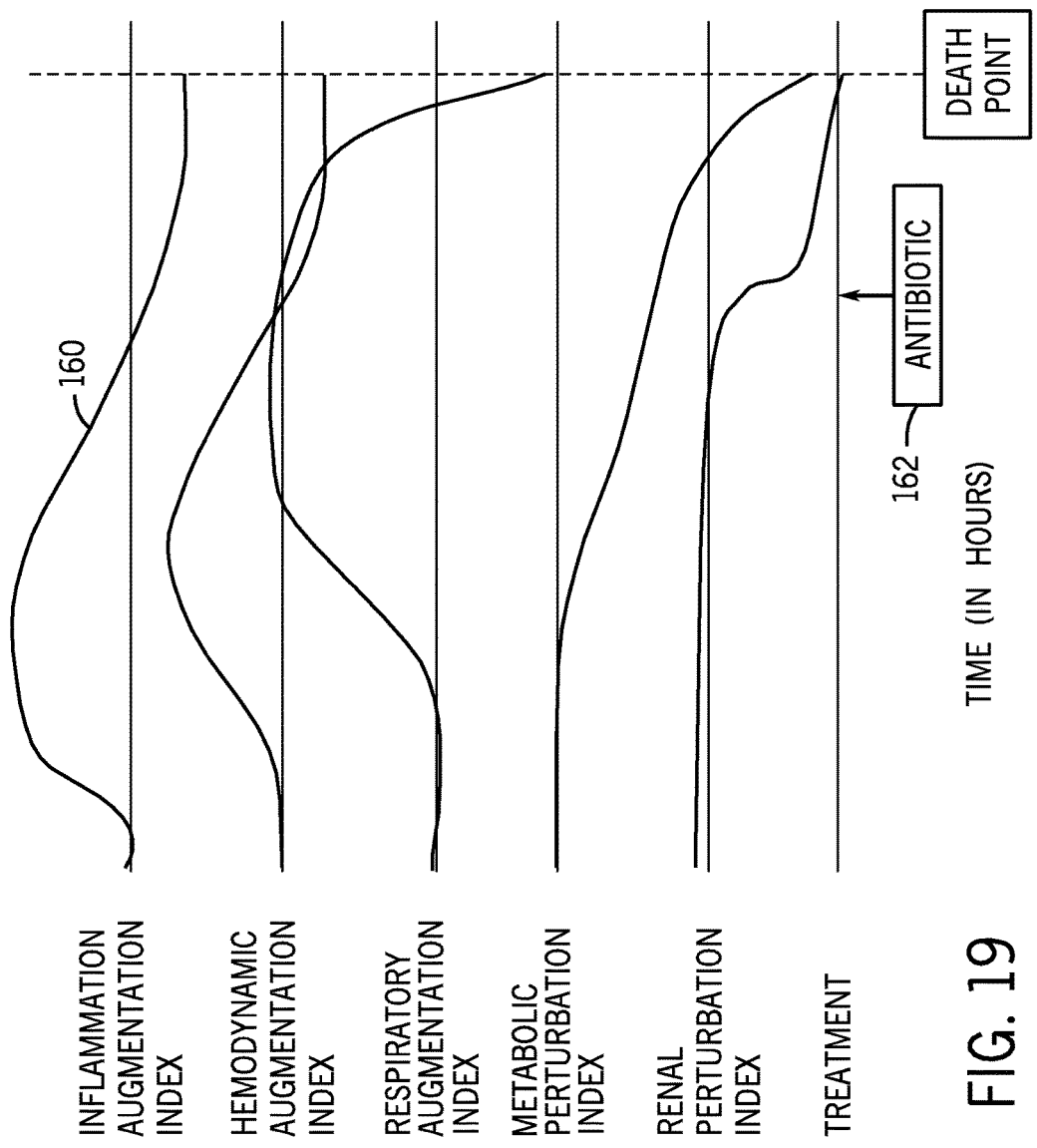
FIG. 19 shows an overview image of perturbation onset and progression from the time lapsed MPPC of FIG. 15A, wherein the perturbations in each grouping are incorporated into an aggregate index along a single smoothed time series for each group.

The image of the progressive cascade 980 shows the drug treatments components 982, 983 of the image are too late because they appear within the image very late along the cascade 980. The late portions of the image of the cascade 980 also include a very ominous beta comprising a rise in anion gap 985. The addition of this new image component provides a mature image of cascade 980, which is now strongly indicative of a highly fatal stage of septic shock. Other image views may be for example; specific expanded portions of the time lines, specific expanded views of aggregate failure components along the timeline portions, specific groupings of the timelines, overviews of perturbation progression from group to group (an example of this is shown in FIG. 19), to name a few.

Figure 15B:
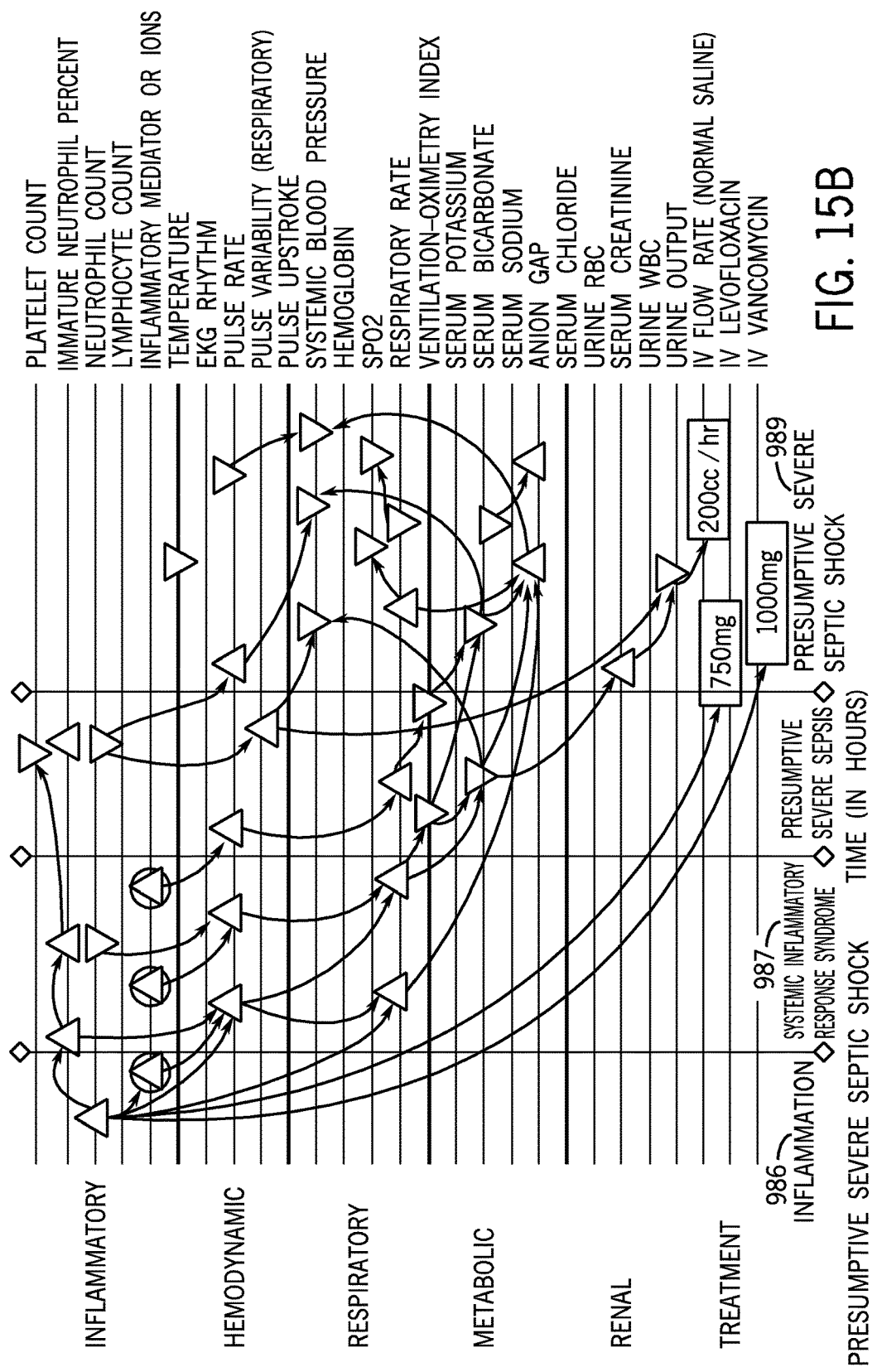
FIG. 15B is a failure image frame that includes a plurality of timelines organized into groupings showing a failure image of an expanding cascade of septic shock with portions of the image being separated into sequential states.

FIG. 15B is the failure image frame of FIG. 15A with portions of the image being separated into sequential states of inflammation 986, systemic inflammatory response syndrome 987, presumptive severe sepsis 988, presumptive severe septic shock 989.

Figure 15C:
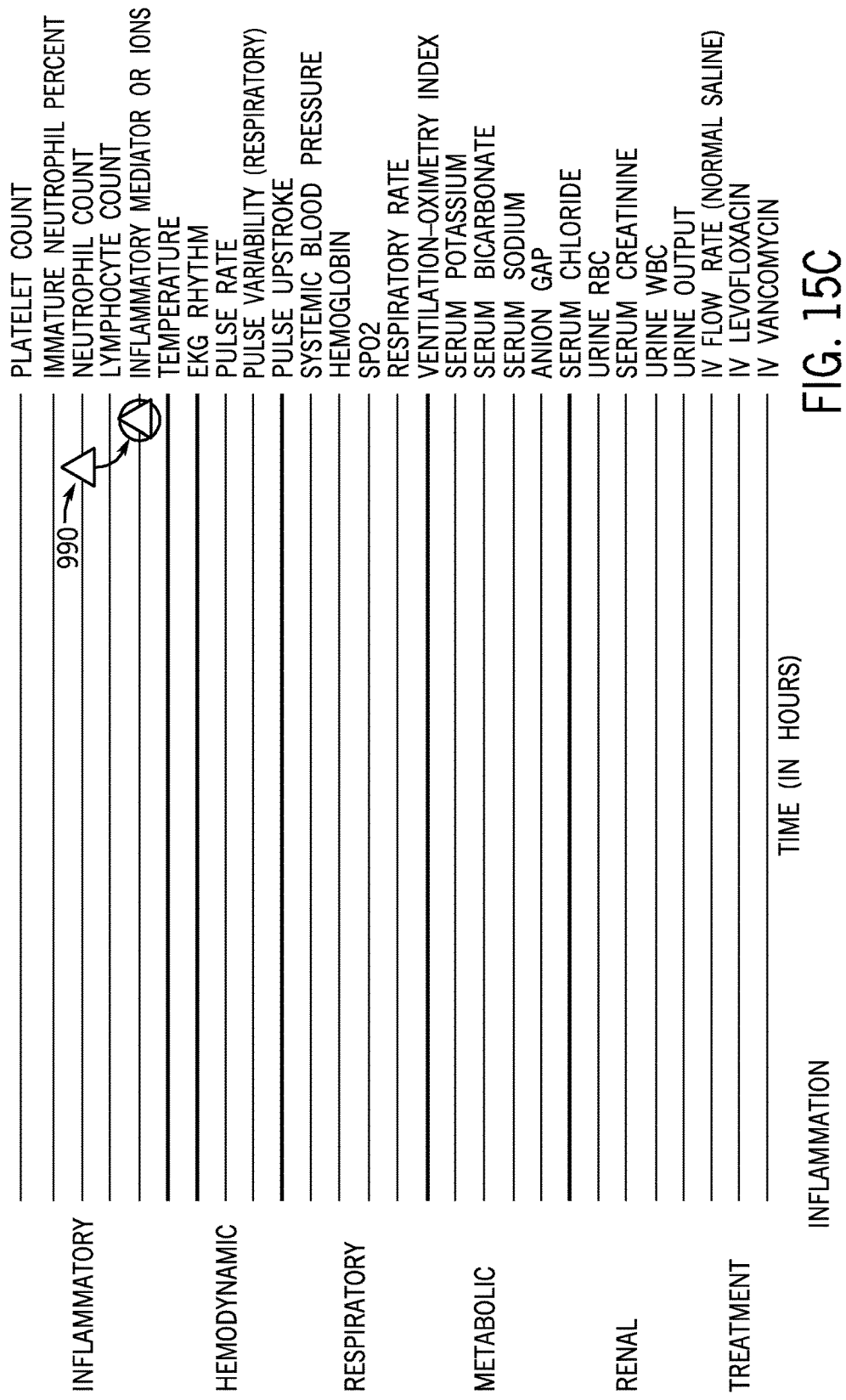
FIG. 15C is a failure image frame that includes a plurality of timelines organized into groupings showing early time-points in an expanding cascade of severe septic shock.

FIG. 15C is an early failure image frame from real time imaging of the process in FIG. 15A that demonstrates that there may be little in these first perturbations to warn of the impending cascade towards sepsis. The first "spark", a rise in neutrophil count 990, evident in this image is entirely non-specific despite the fact that it, in retrospect, heralds the onset of septic shock, completely disappears by the time this motion picture has reached the point illustrated in FIG. 15D (see below) in which focused testing, more frequent CBC testing, and/or more frequent vital sign measurement to determine the significance of this rise in Neutrophil count may be suggested or ordered by the processor 304 to expand the image to more quickly move toward a more specific image.

Figure 15D:
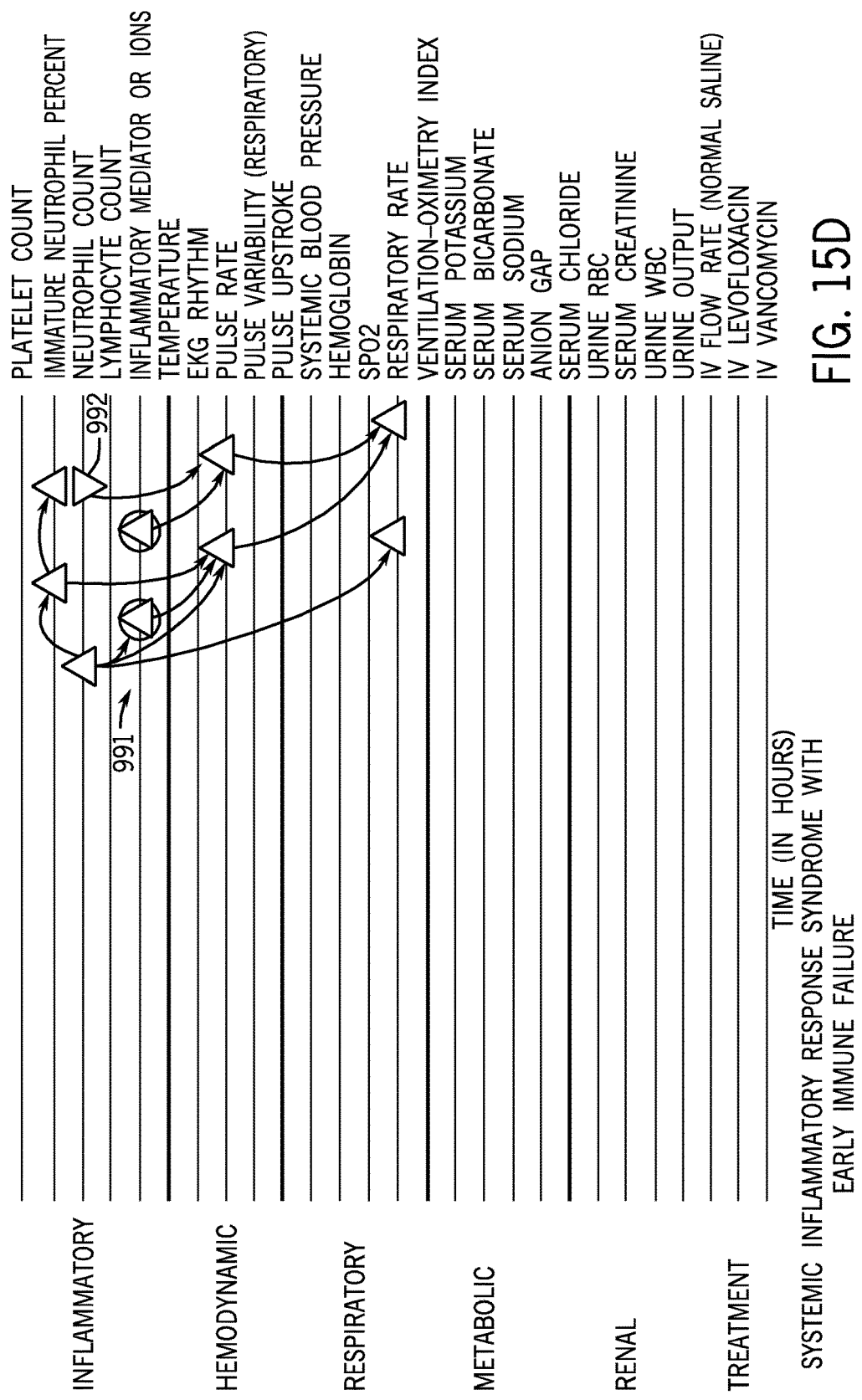
FIG. 15D is a failure image frame which shows an image of a failure cascade severe septic shock with inflammatory, hemodynamic, and respiratory augmentation, and with early immune failure.

FIG. 15D is a failure image frame from real time imaging of the process in FIG. 15A. This frame demonstrates early image components of inflammatory, hemodynamic, and respiratory augmentation 991 combined with early immune failure 992. As indicated by the image, serious sepsis is highly likely if treatment does not occur by the time this frame of the MPPC has passed.

Figure 15E:
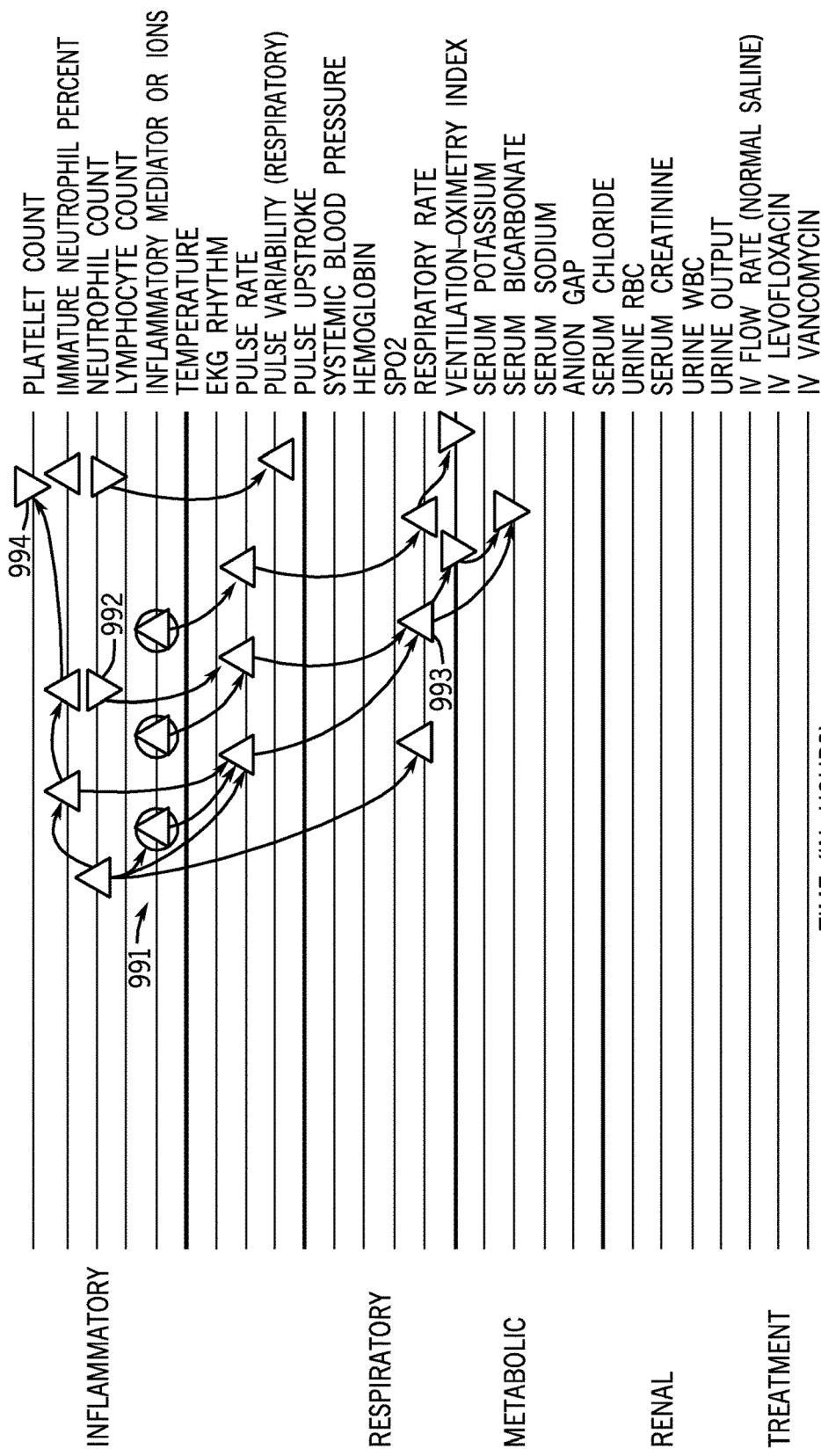
FIG. 15E is a failure image frame which shows an image of a failure cascade of severe septic shock with inflammatory, hemodynamic, and respiratory augmentation, with immune failure, and with evidence of decline in respiratory gas exchange and fall in platelet count.

FIG. 15E is a failure image frame from real time imaging of the process in FIG. 15A. This frame demonstrates demonstrate the image components of inflammatory, hemodynamic, and respiratory augmentation 991, with immune failure 992, but now with image components indicative of a decline in respiratory gas exchange 993 and fall in platelet count 994. As indicated by the image, serious sepsis is even more likely than or the stage shown in FIG. 15D if treatment does not occur by the time these frames of the MPPC have passed.

Figure 15F:
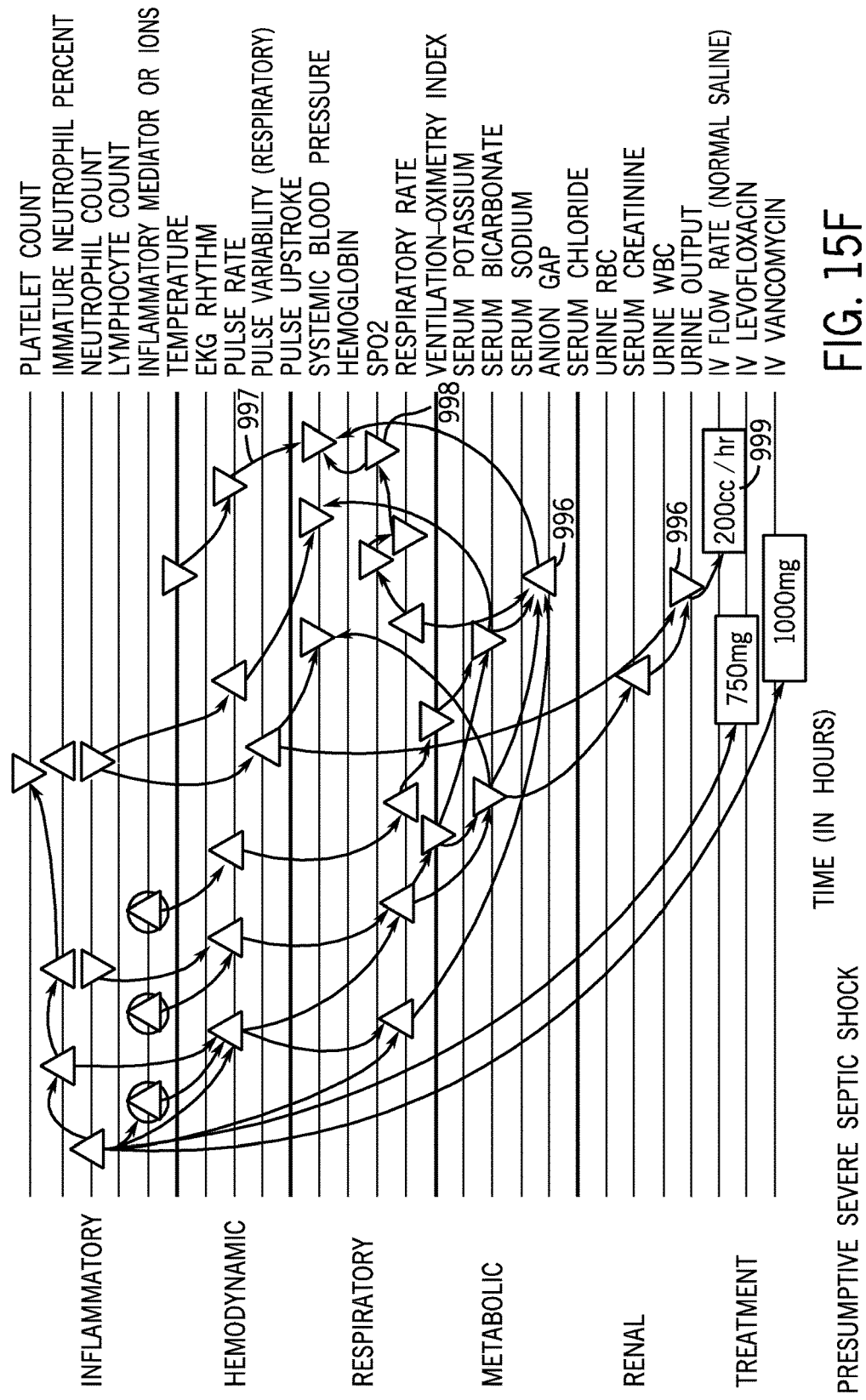
FIG. 15F is an exemplary failure image frame showing an image of an advanced cascade of severe septic shock with progression to metabolic failure, renal failure, hemodynamic failure and respiratory failure.

FIG. 15F is a failure image frame of FIG. 15A to demonstrate that the image now shows expansion the failure cascade from the frame in FIG. 15E to now include the image components of metabolic failure 995, renal failure 996, hemodynamic failure 997 and respiratory failure 998. This is the point wherein medical intervention for sepsis begins in many patients monitored by today's electronic medical record and monitoring systems. The introduction of treatment at this point of the movie is often entirely ineffective. The introduction of fluid resuscitation 999 at this late frame of the image will likely have little effect on progression of the patient.

Figure 16:
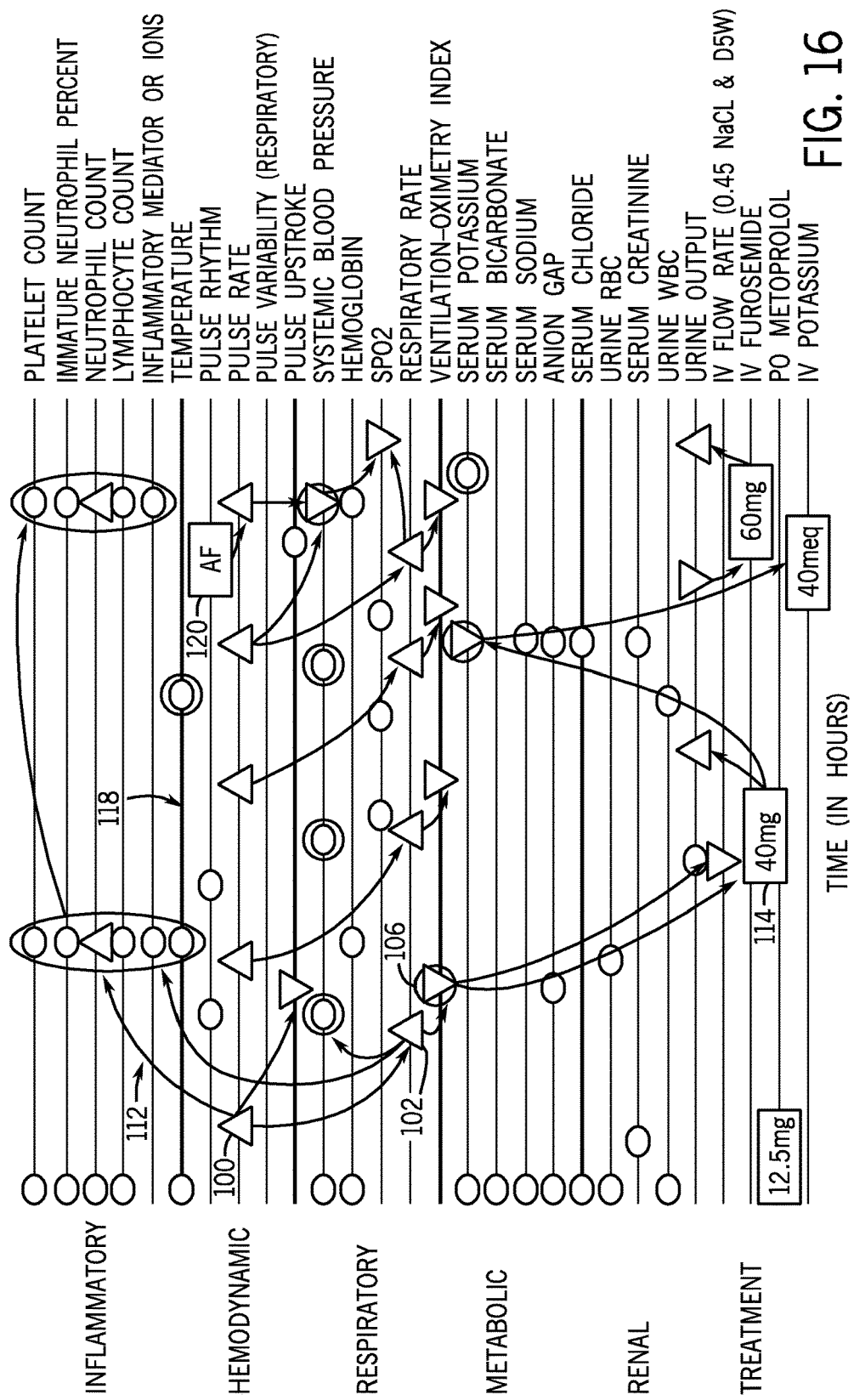
FIG. 16 is an exemplary congestive heart failure (CHF) failure image that includes a plurality of timelines organized into groupings.

FIG. 16 shows a time lapsed failure image frame of the failure cascade of congestive heart failure. Note the first perturbation event detected by the processor is hemodynamic (a rise event in pulse rate 100), rather than inflammatory as in FIG. 15A. The next detected perturbation event is respiratory, a rise in respiratory rate 102 which combined with the rise in pulse 100 produces the first relational binary 104. There is a fall in the ventilation indexed oximetry value 106 producing a second relational binary 108 with the rise in respiratory rate 102. The rise in respiration rate 102 is the beta event of the first relational binary 104 and the alpha event of the second relational binary 108. Together these two joined relational binaries form an image component 110, which may be followed back to the initial onset of the image of the nascent cascade 112. Treatments including furosemide 114 and metoprolol 116 are initiated fairly close to the onset of the image of the nascent cascade 112 but are not effective in preventing subsequent occurrence of an image of a progressive cascade 118. This image of a progressive cascade 118 is defined by the both the components and length of the MPPC. The processor 304 upon detection of this failure image may search for the fundamental cause of the cascade progression by automatically ordering cardiac enzyme (not shown) and other tests if the safety committee of the hospital desires these types of proactive measures. Note the cascade 118 includes the development of atrial fibrillation 120 and subsequent further deterioration.

Figure 17:
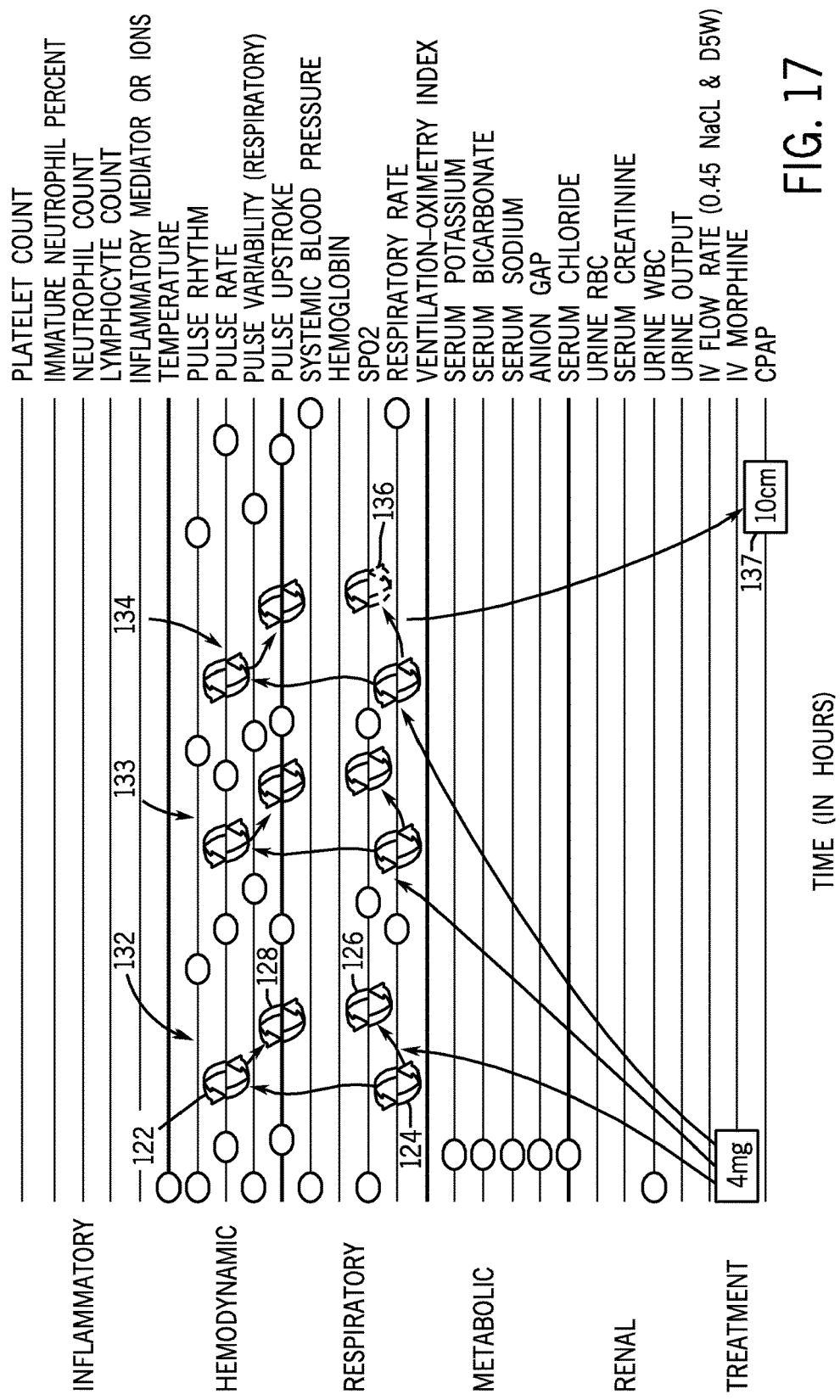
FIG. 17 is an exemplary sleep apnea failure image that includes a plurality of timelines organized into groupings.

FIG. 17 shows a failure image frame of sleep apnea. The first perturbation events occur in a group that includes cycling events of pulse rate 122, respiratory rate 124, $SPO_2$ 126, and pulse upstroke 128. These occur after the initiation of a narcotic dose of 3 mg IV 130. The aggregated image components showing cycling 132 then repeats to produce second such image components g 133 and third such image components 134. The $SPO_2$ cycle 135 portion of the third image components showing cycling 134 becomes more severe with recovery failure 136. CPAP treatment 137 is given timely and no further narcotic is given. In this case, there is no image of an expanding cascade or progressively declining respiratory rate or declining $SPO_2$ to indicate life-threatening narcotic induced sustained hypoventilation. On later review, as in morning report or with teaching rounds, the entire MPPC, which contain this frame, may be reviewed by moving along a fast framed image to better visualize the subtleties of the progression furthermore the physician or nursing group may drill down to see that actual time series (as, for example, by right clicking on the $SPO_2$ cycling symbol 137). The decision as to whether or not the treatment in this case rendered timely care may be assessed. In an example, the physicians in the session may petition the patient safety committee to adjust the patient safety processor to provide a recommendation for earlier automatic RT department notification, along with the nurse notification when images such as those defined in the early portion of this motion picture are present. In this way the Patient Safety Processor becomes an integral part of the continuous quality improvement actions of the hospital system with the goal being to move treatment and testing leftward into the earliest frame which provides sufficient image support for the treatment or testing. The goal is to a continuing move toward earlier treatment of the source of the early perturbations before the cascade develops. According to one aspect, the processor 304 is integrated into the continuous quality improvement process and the processor 304 becomes an integral part of a hospital's quality improvement committee meetings and a major source of hospital-wide as well as focused analysis and a mechanism to rapidly institutionalize quality improvement focused change.

Figure 18:
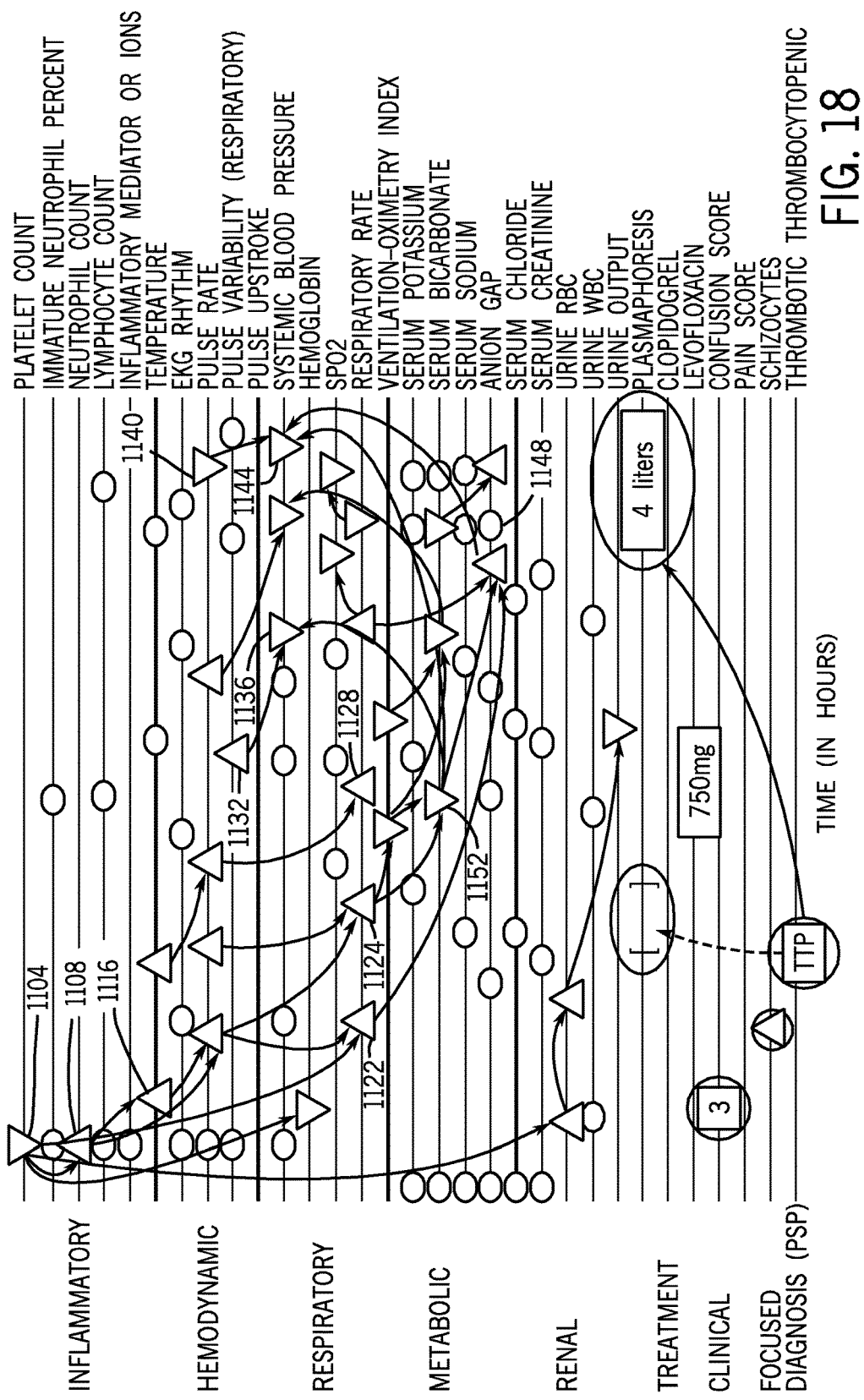
FIG. 18 is an exemplary thrombocytopenic purpura failure image that includes a plurality of timelines organized into groupings.

FIG. 18 shows a failure image frame indicative of a high confidence of thrombotic thrombocytopenic purpura (TTP) a rare thrombotic and inflammatory condition which mimics the image of septic shock. TTP may be caused by the inhibition of ADAMTS enzyme by autoantibodies but this disease may also be rarely triggered by the very common drug clopidogrel. TTP often occurs within 2 weeks of drug initiation and may result in serious adverse events if not detected. Unfortunately, TTP shares many of systemic response features of the very common disorder of sepsis (FIG. 15A) which also causes thrombocytopenia. Since sepsis is a much more common condition, misdiagnosis of sepsis in the presence of TTP is a high possibility; furthermore, as with most pathophysiologic failures, both processes may coexist in a single patient along with other related conditions such as systemic lupus erythematosis and pancreatitis. Despite the fact that the moving images of failure in TTP and sepsis are similar, misdiagnosis of sepsis in the presence of TTP may be serious, since TTP cannot be expected to respond to antibiotic treatment and misdiagnosis of TTP s in the presence of sepsis may also be serious, since sepsis cannot be expected to respond to plasmaphoresis without antibiotics.

TTP is associated with the accumulation of large multimers of Von Willebrand factor, which damages red blood cells and induces extensive micro vessel thrombosis, resulting in confusion, renal failure and microangiopathic anemia, which is associated with sentinel schizocytes that may be detected in the peripheral smear of blood (if the diagnosis is suspected and the test is ordered). Thrombocytopenia, renal failure, and hematuria may appear earlier in this process than with sepsis but these early findings are only an image clue and do not differentiate two MPPCs.

The MPPC suggestive of TTP is generated by the processor 304, with the processor 304 indicating a failure image consistent with the possibility of sepsis and/or TTP and other less likely conditions such as an acute vasculidity. The processor 304 may output non-specific characterizations of the image such as "image consistent with a life threatening acute or sub-acute thrombotic and inflammatory augmentation" and may present a differential diagnosis of the processes that may generate such an image.

Also, as for example upon the detection of a threshold frame or frames, the processor 304 may automatically order the peripheral smear, blood cultures, urine cultures, sputum cultures, chest x-ray, ANA, pancreatic enzymes, renal sediment, and ANCA study to enlarge and fill in the gaps of the image as rapidly as possible. It is the hospital experts who will ultimately decide the cost-effective balance of ordering these tests as defined by the position the tests are ordered along the cascade. If desired, the reports form the chest x-ray may include a section that will appear as a time series (as for example, a step function). The radiologist in the interpretation may enter an indication of pulmonary infiltrate, pulmonary edema, and the like and may indicate worse or better which may result in a step change from the last test. In this manner, the results of studies such as chest x-rays become a source for time series rendering and incorporation into the failure imaging process.

The presence of an image that includes image components defining a failure cascade 139 that includes inflammatory-hemodynamic respiratory-augmentation (IHRA) 140 with an early fall in platelet count 142, a fall in the ventilation oximetry index (VIO) 144, a fall or threshold value of hemoglobin 146, an rise or threshold value of a confusion score 148, and/or a rise or threshold value of red blood cells in the urine 150, and/or a rise or threshold value of creatinine 152. Together the combination of image components produces a MPPC suggestive of the possibility of TTP and/or sepsis and/or other less common processes. For example, if the patient had just received blood it would suggest a possible transfusion reaction.

The processor 304 may indicate to the healthcare worker the gravity of the image, a differential diagnosis as suggested by the image, the general type and/or physiologic description of failure cascade present, as well as a notification that the detection by the patient safety processor of this type of image may lead to prompt notification of the attending physician and transfer to ICU. If the image has insufficient binaries because results are not available to define enough beta components to define the presence of the failure image suggestive of TTP with a sufficient confidence level to take action, the unavailable tests are ordered upon the detection of the partial image in an attempt to complete the image. Note in FIG. 18, the detection of the image components suggestive of the possible presence of a complete MPPC of TTP triggered the test for schizocytes 152 in an attempt to complete the TTP image. The detection of a threshold value step function, and/or rise in schizocytes combined with the rest of the image triggers the warning of the potential presence of TTP. FIG. 18 reflects suboptimal care in a retrospective case that was detected by the processor because the plasmaphoresis 154 order was carried out too late. Such delays may be detected in reviews of medical history data, and the processor may be configured to provide an automatic report of variance to the quality improvement department of the hospital.

In certain embodiments, human delay in physically following the orders of the patient safety processor may be addressed by building escalating alarms into the processor 304. The time in carrying out the order is determined by the processor 304, and the processor 304 may be programmed to up-indicate the warning upon increasing delay. To prevent this delay, the processor 304 may be programmed notify another station if action is not taken in response to detection of various evolving failure images such as the one in FIG. 18. These may be decided, for example, by the hospital quality improvement committees or by individual physicians or nurses if desired so that the patient safety processor improves over time and may be adjusted to compensate for the diligence of the healthcare worker. The patient may receive Levofloxacin early to cover the possibility of sepsis as the image was also consistent with sepsis and the healthcare workers decided to empirically treat for sepsis (albeit with somewhat limited antibiotic coverage). However, the cascade proceeds despite antibiotic therapy. Since a cascade is an image component and the relationship of the cascade, its growth, and its features and its timing within an MPPC in relation to the dose, timing, and type of treatment also forms part of the MPPC, these relationships may be automatically assessed by the processor in real-time to determine if treatment is effective. The hospital safety committee or infectious disease committee may decide whether or not to reprogram the patient safety processor to make antibiotic suggestions based on various ranges of failure images before the results of cultures are known.

FIG. 19 shows an overview image of perturbation onset and progression as derived from the time lapsed MPPC of FIG. 15A wherein the perturbations in each grouping are incorporated into an aggregate index along a single smoothed time series for each group. Note this is a typical progression of sepsis with initial involvement of the inflammatory group 160 then each other group is involved in progression. Note the late timing of the treatment 162 is particularly evident in this summary view derived form the more complex images.

Rather than, or in combination with, an index, if desired the processor 304 may be programmed to provide an indication of the severity and number of the aggregate perturbations in each group. These may be for example designated by many enlarging or colored arrows, other icons, and/or timed instability scores, to name a few. Many such options may be included so that the user may define his or her preference to visualize the sequence and patterns of cascade progression across groups.

A range of expert and pattern recognition systems may be applied to analyze the images and the image components generated by the failure image processor. These comprise the image identification processor. In one embodiment the image identification processor works with the failure image editor, which allows the user to select the images for detection using for example from a drag and drop interface. In an embodiment the drag and drop interface provides for the discretionary selection of, for example, the time-series type to be selected, then the events and binaries are selected on each time-series type in order and the ranges of relative positions and orders of the events and binaries is selected. In this example, the failure image editor allows customization of the desired ranges for the components of the images (and therefore the ranges of the images themselves) to be selected as well as the response of the image identification processor to the detection of a given image and/or images. The failure image editor may allow for selecting the ranges of timing and order of the events and binaries to generate a specific output such as a proposed diagnosis, warning, order for more testing or imitation or termination of treatment. The image identification processor may also be adaptive such that a physician inputs the diagnosis present, such as for example septic shock, with a given image. The physician may also capture a given image or set of images into the failure image editor to then select ranges about the events and binaries within the image which also would have indicated the presence of septic shock so that the adaptive image processor may learn more quickly.

FIGS. 15A-F, 16, 17, 18 and 20 represent a 2 dimensional "time lapsed" snapshot view four MPPC after they have proceeded to advance states. This view also provides an alternate user interface for the creation and editing of the Failure Image Definition Set. Researchers may use a failure image editor to create and manipulate failure models.

Figure 20:
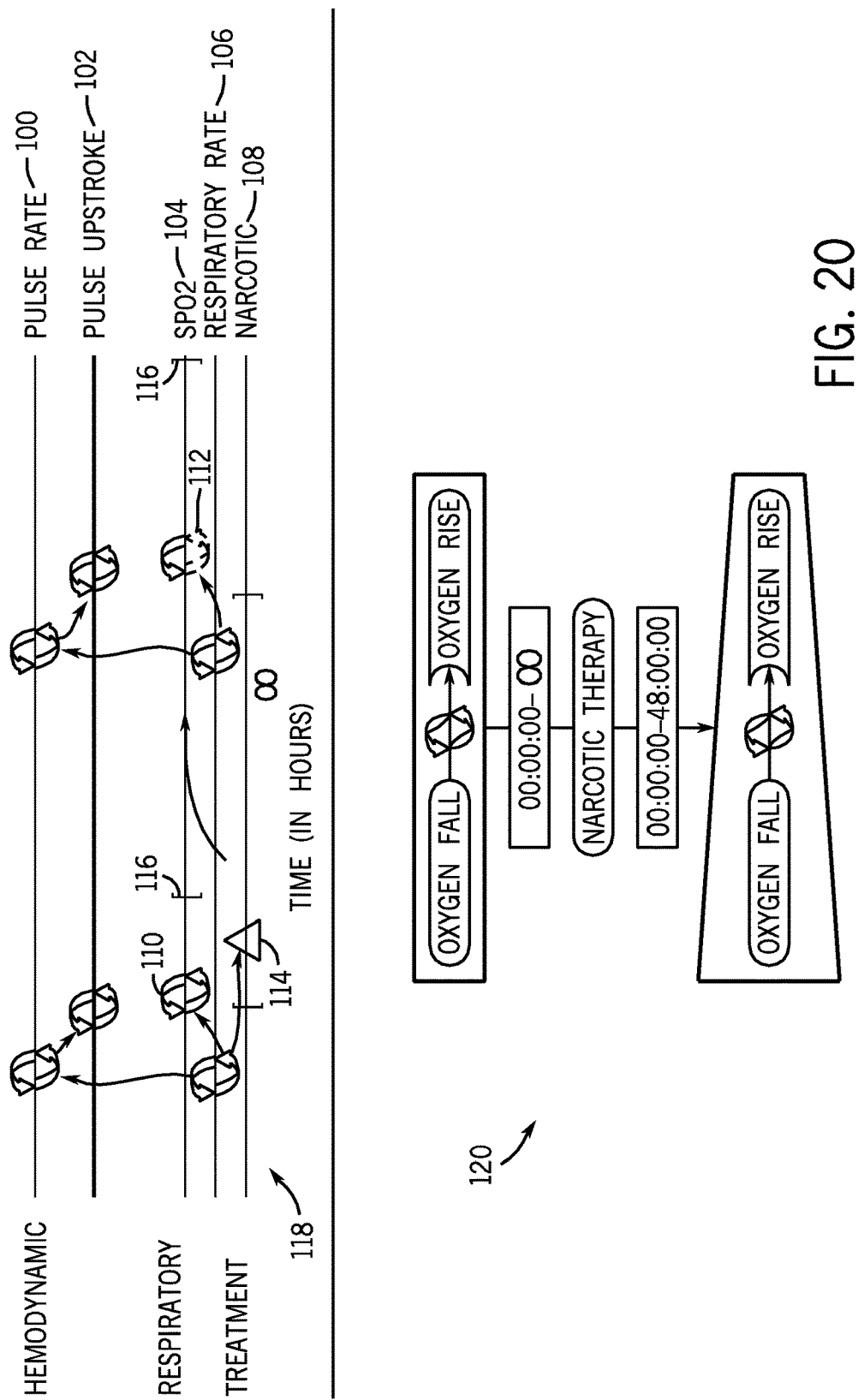
FIG. 20 is a general failure image that includes a plurality of timelines from the complexity diagram of FIG. 1 showing a failure image of excessive secretion of serum inappropriate antidiuretic hormone (SIADH) induced fall in hyponatremia.

In one embodiment researchers work from the top down to define failure images. Researchers begin by selecting a set of channels in which they want to "paint" the failure image. FIG. 20 depicts the failure image editor being used to "paint" the narcotic-induced ventilation instability failure image. Channels (100, 102, 104, 106, 108) may be ordered in any number of ways, by sorting, categorizing or by simple drag-and-drop selection of location within the failure image editor. Channels may be duplicated (e.g., 100, 102, 104, 106) to expand the image so that the relationships may be defined in a non-overlapping way for complex definitions that define multiple relationships. The failure image editor maintains the relationships within and between defined elements within the channels regardless of their vertical location within the editor. Researchers then select a channel and the failure image editor presents a set of events and binaries that are available which apply to the given channel. Researchers may select any of these elements and drop them on channel. Also, the researcher may create a new element (event or binary) at any point within a channel (for example using a right-click menu editor). Locations within the editor indicate relative locations in time between selected and/or created elements. If a binary is dropped upon a location, the failure image editor determines whether the beta or the alpha event belongs on the channel selected and places the event within the channel and the corresponding event (beta or alpha) on the channel indicated by the relational binary definition. If the channel is not currently in the failure image editor then it is added. Relational binaries that collapse down to a single icon (e.g., cycling within a single channel) will show the single icon 110, 112 rather than the alpha and binary events. The location of the corresponding event is determined as the midpoint of the search window definition. The entire window is shown as a set of parenthesis 116 indicating the range of the search window relative to the corresponding event, in this case a treatment event with an IV narcotic 114. Search windows are shown only within the beta channel of the relational binary and the event itself is show within the midpoint of the search window. If an event is both a beta and an alpha event the search window displayed is around the event is specific to the event when it is participating as a beta event. Search windows may be suppressed within the editor and/or shown only within the relational binary currently selected due to the fact that a single event may be the beta of any number of binaries. Individual events may be dropped onto a channel or created on a channel. New event types may be defined within the failure image editor. Events may be connected with a drag-and-drop selection or with an alpha and beta click selection, for example to define new relational binary types.

The entire image or sections of the image may then be persisted as an aggregate failure mode. The failure image editor works in concert with the aggregate failure mode editor to create and modify failure image definition sets. Furthermore, the aggregate failure mode editor works in concert with both the convergence editor and the event editor to create and modify the binary and event definition sets. In FIG. 20, the definition of aggregate failure modes is accomplished with a split-screen view showing the failure image editor in the top pane 118 while the aggregate failure mode editor is in the lower pane 120 showing an alternative type of failure mode diagram. These two models are completely synchronized with changes in one immediately reflecting the change in the other.

In one embodiment researchers work from the bottom up to define failures from a set of time series. Researchers may begin with a set of actual time series from patients diagnosed with known failures, with a set of time series generated by the processor to simulate certain conditions or a set of time series simulating no perturbation at all within a patient. This set of time series may be designated as immutable (for example with the set of actual time series) or may be edited to provide a sample of the patterns being defined. Researchers may select portions of the time series which the failure image editor then will analyze to provide candidate event definitions. Alternatively the researcher may select parameters to define an event and the time series displayed will indicate the results of that definition overlaid on top of the time series to provide visual guidance to the researcher. Once the researcher completes the definition of an event the failure image editor will compare that definition with other definitions within the same channel. If similar patterns are found the researcher is alerted and allowed to create a new event type or select one of the event types already selected. If the event is a relational event, the researcher may select a corresponding event from which relational parameters may be defined and experimented with or the researcher may simply define a function (e.g., >2×relative magnitude). Once an event has been fully defined then the researcher may choose to relate the event to another event within the image or to a search window within the image (e.g., to indicate a missing or null event). The researcher may indicate that a processor-ordered event as the beta of a relational binary. Groups of events and relational binaries may then be selected to define an aggregate failure mode.

In one embodiment, the failure image editor may be presented with a large collection of time series sets provided with the indication of the presence or absence of a particular known failure image. The failure image editor creates a set of candidate definition sets refining them to create the right specificity and sensitively to match the sample set. Once the best-fit definition sets are created, a second large collection of times series sets are provided with the indication of the presence or absence of a particular know failure image. The failure image editor first uses the candidate definition set, determining sensitivity and specificity, and then refines the definition set to be better suited if possible to both the first and the second collection of sample data. This process may be executed iteratively until a best-fit set of definition sets is created or the process is deemed not to be asymptotic and is abandoned.

In one embodiment the failure image may be "played" or executed by the image editor as a MPPC to provide further time-specific markers. A default execution of a failure image is "played" by placing all events as specified in their default (e.g., midpoint) location within their respective search windows as defined by the image definition. A sample result of this is displayed in FIG. 15A. Once the image is played vertical markers are placed within the timeline as in FIG. 15A to indicate progressive states within an evolving image. In this way, the image definition may be provided the specifications by which the image state may be identified and displayed within the patient safety monitor.

In an alternate and/or complimentary embodiment, the image editor provides the ability to split the execution of an image into multiple intermediate and/or end states. Each different branch within the failure image definition may be defined as a state within a failure image or a different, albeit related, failure image. Trees of related images may be composed to provide alternative evolutions of failure within the failure image definition.

Figure 21:
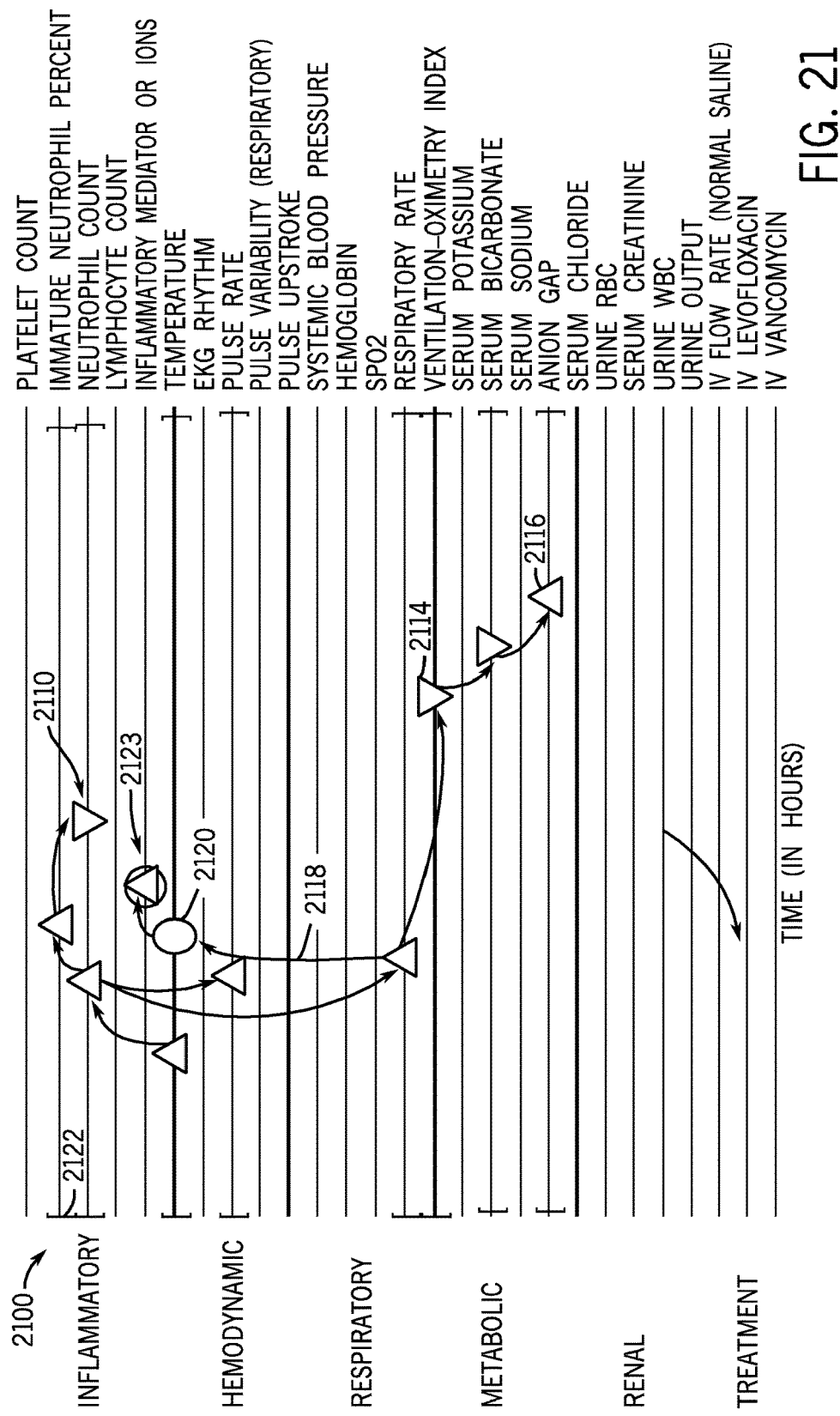
FIG. 21 is a split screen diagram of a drag and drop interface for constructing combined physiologic and treatment images for the patient safety processor showing the construction of an MPPC indicative of narcotic-associated recovery failure in the presence of sleep apnea.

FIG. 21 is a frame from a time lapsed motion failure image that includes a plurality of timelines from the patient illustrated in the failure mode diagram of FIG. 1. In this image, a patient who has experienced a stroke has developed a condition associated with serum inappropriate antidiuretic hormone (SIADH), which induces a induced fall in serum sodium and confusion. The patient presented with an acute stroke but was recovering and alert. Then he slowly began to develop confusion and less alertness. As the stroke was large, the nurses and physicians managing the case thought that the patient's confusion and obtundation was due to brain swelling. The patient $SPO_2$ and ventilation rate were normal, he had no signs of sepsis and because of recently normal electrolytes, the attending physicians did not think that a metabolic cause for the confusion was a reasonable option. In other words they misdiagnosed the pathophysiologic failure pathway (illustrated on the failure mode diagram 200 of FIG. 1) and they thought the pathophysiologic pathway was following the direct connecting line 170 between stroke 208 and confusion 220 as shown in the failure mode diagram 200 in FIG. 1. However, prior to the onset of the confusion the patient was receiving 0.5 NS in spite of the fact that that he was eating and drinking. Repeat serum sodium confirmed a fall in sodium and SIADH was confirmed with additional testing. Cautious correction of his sodium resulted in rapid recovery and resolution of the confusion and obtundation.

Since the stroke caused the SIADH (which cased the fall in serum sodium), the actual modes of failure were significantly different than suspected by the hospitalist in this case. Referring again to FIG. 1, the actual failure followed from the stroke 208 to the hyponatremia 242 and then followed from the hyponatremia 242 to the confusion 220. In this case the patient survived the missed diagnosis but he experienced several extra days unnecessary days in the hospital because of delay in detection and treatment of this failure.

FIG. 21 shows an image frame 2100 of a failure image editor for constructing a range of MPPC for recognition by the processor 304 for the patient described in FIG. 1. In this case the failure image shown is consistent with presumptive severe sepsis. The inflammatory/hemodynamic/respiratory augmentation 2110 is followed in the image by a fall in VIO 2114 and metabolic failure with a rise in anion gap 2116. Note that if the inflammatory/hemodynamic/respiratory augmentation 2110 is unassociated with a rise in temperature 2118 (a null binary 2120 is identified), inflammatory mediator markers 2123 are ordered to confirm the presence of the inflammatory component of the failure image. The typical sequence of binaries is shown but these events may occur in any order. The processor 304 may provide greater confidence if the order is as shown and lesser confidence if the order is different that shown. As noted failure images may overlap such that patient with preexisting hemodynamic instability may become septic, for this reason, in this case the order is not deemed pivotal. However, for some failure images the order of events may provide much greater specificity (in which case the parentheses may be adjusted accordingly. At first the failure image editor may be set to be more liberal and then adjusted as hospital experience and quality improvement may dictate.

Figure 22:
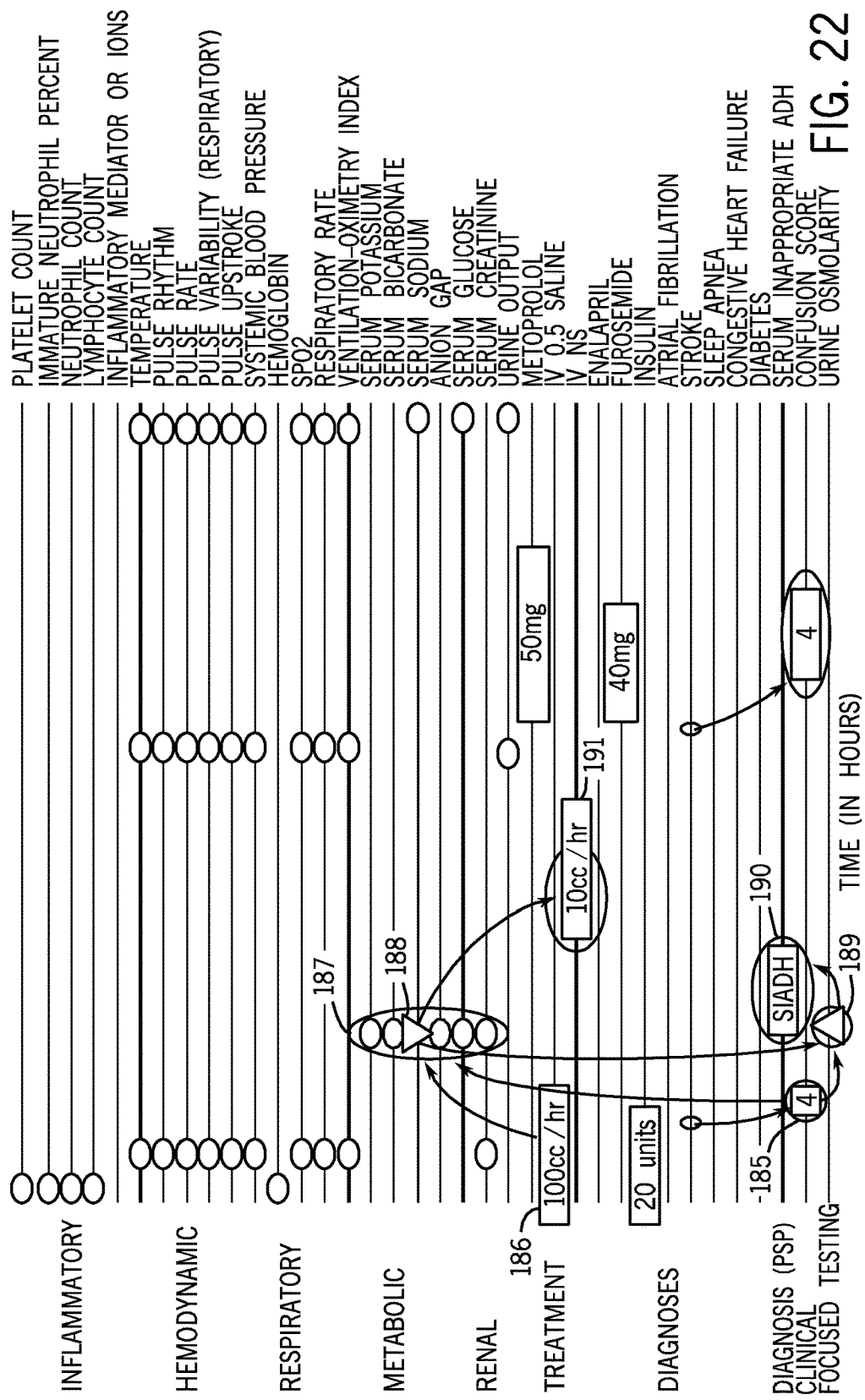
FIG. 22 is an exemplary image frame of a failure image editor for constructing a septic shock MPPC for recognition by the Patient Safety Processor.

Now referring to FIG. 22, this exemplary image is derived from a patient with the failure mode diagram of FIG. 1 having a timeline for a stroke, diabetes, atrial fibrillation, a history of congestive heart failure, and sleep apnea (in this case superimposed sepsis is not present). These correspond to the failure mode diagram of FIG. 1 illustrating potential relationships between stroke 208, diabetes 202, atrial fibrillation 206, congestive heart failure 204, and sleep apnea 210. Note that patient safety processor is ordering routine confusion scores 185 because of the timeline indicating a stroke. The detection of an increase in confusion 185 or the presence of hypotonic saline administration 186 to a patient with a stroke timeline automatically triggers a measure of electrolytes 187 and upon the detection of a low serum sodium 188 the processor orders a urine osmolarity 189 and indicates a high probability of SIADH 190 and recommends an adjustment in fluid therapy 191. Here the problem is simple but the early signs of failure were at first subtle at a time when intervention would have prevented the increased length of stay later the pathways of failure were confused leading to further delay and considerable family since they were told the incorrect diagnosis. In this case the nurses and physicians may have been busy or may have been inexperienced or simply not familiar with the subtle decline in mutation which may attend the development of SIADH in a stroke patient. The reason subtle findings are missed is myriad. Note also, as illustrated in the failure mode diagram of FIG. 1, this is simply one failure and there are very many potential failures for this complex patient. Furthermore, in this case the serum sodium was nearly normal when the low sodium was finally detected so many physicians may not think the level was sufficiently low to cause these symptoms or warrant intervention. However, the sodium had dropped from a high normal to just below normal and in patient with brain edema the magnitude of the fall in serum sodium may be more significant than the absolute value and this variation in vulnerability from patient to patient and within the same patient depending on coexisting disorders, diseases, and medications are not concepts which are easily grasped by some healthcare workers who have observed patients with very low sodium without any change in mentation. This illustrates the value of generating and recognizing a moving picture of the failure and care. The patient safety processor does not trigger an alarm or define a diagnosis by a single threshold breach, because the system analyzes the entire failure and care image over time and is programmed to recognize that this image indicates vulnerability to a fall in serum sodium, even a fall that does not go below threshold. The patient safety processor provides the advantage of continued vigilance and continuous consideration of all of the potential physiologic failures which are consistent with the images. According to one aspect, failure mode diagrams, such as the one in FIG. 1, may be used to construct prospective or retrospective failure images as in FIG. 22 by applying the cascading binary relationships between diseases, treatments, and perturbations to construct failure images and image ranges using the failure mode editor.

The processor 304, as applied to the disclosed embodiments, is not constrained by the exemplary definitions provided herein, but may rather compare actual data to a plurality of MPPC images (stored or real-time) and image states to find best-fit matches. In one embodiment, the best-fit matches may be determined by image registration techniques. In embodiments, the matches may be made by image similarity measures that include cross-correlation, mutual information, sum of squared intensity differences, and ratio image uniformity. The processor 304 may indicate all possible images and image states ranked by level of confidence. For example the processor 304 may indicate that a MPPC is consistent the systemic inflammatory response syndrome with a high degree of confidence and early septic shock with a medium degree of confidence and that TTP (and other potential alternatives) or overlapping failure modes are remotely possible in view of the image and remain to be excluded. The physician may be asked if it is desired to order the focused testing to exclude these remote alternatives or overlaps and/or the processor may be programmed to automatically add this testing based on a specific range of images (as defined, for example, using the drag-and-drop editor discussed previously).

The identification of failure within the processor 304 is not the single selection of a failure mode or a failure state, but the ranking of a set of images with regard to their fit within the data presented. The identification of multiple failure images is not simply the selection of alternatives. Multiple failures may, in fact, exist and be interacting with each other. Early states of some failure images may be very similar, or in fact exactly the same, as the early stages of other failure images or of a combination of failure images. The processor 304 provides the analysis and visualizations that may allow the health worker to understand the current state of the patient (and patient environment) in terms of possible future states—alternatives and candidate overlaps—along with confidence levels as to their specification. Further, the processor 304 allows the health care worker to query the patient's condition with regard to confidence levels and, in particular, the comparative confidence level between two images and/or image states. For example, the confidence level for sepsis is low with the frame shown in FIG. 15B, whereas it is intermediate for frame in FIG. 15C and high for FIGS. 15D-15F. These confidence levels, along with the action desired, may be programmed into the patient safety processor in advance by specialty groups, hospital safety committees, and/or may be customized and "tuned" by individual physicians and or may be applied adaptively by the processor by comparing the entered new diagnosis with the present image and recoding that image as indication of that state. In the adaptive mode, the processor may be programmed to ask "is this failure image indicative of a failure process defined by this newly entered diagnosis and, if so, please specify the first event, binary or image component which in retrospect was part of this specific failure process".

In one embodiment, the processor 304 may be trained by a pathophysiological engine (such as a human simulator, as is known in the art) for the creation of failure and response images. Given a specified event definition set and binary definition set, the patent safety processor provides a dynamic image derived from the input of the pathophysiologic engine and the processor is instructed as to the nature of the images so that when these images are detected in the future they are recognized. In one embodiment, a human simulator is connected to the patient safety processor to provide an improved teaching tool for healthcare workers. Researchers may select to be presented with a normal, unperturbed patient with various conditions. Once a dynamic image of the patient is displayed researchers may introduce perturbation into the pathophysiological engine which will result in new dynamic images from the processor 304. For example, a research may select relationships presented according to a convergence and toggle them to divergence. Also, random divergence may be configured into the system. Divergence with respect to a single or a set of response system(s) may be specified to model the breakdown of systemic response. Divergence may be configure globally or for a specific timeframe indicating that systemic response fails, or is delayed. In this way, both perturbation and failure of systemic response may be selectively introduced to create failure images. These failure images may be persisted to be further edited within the failure image editor. The researcher may select several different variations and save them as failures and/or failure states. These failures and/or failure states may be persisted within a failure component definition set to be used by the failure image processor. Further, resultant failure images may be compared with actual patient data to refine event and binary definition sets.

Alternately or in combination, according to one embodiment, an MPPC from the processor 304 may be simulated by a processor driving the human simulator so that healthcare workers may observe the reanimation of the MPPC of the patient safety processor either as a digital animation or as a reanimation derived from output of a human manikin. One utilization of the embodiment that combines the pathophysiological engine to the processor 304 is to model treatment protocols. The engine may output expected or unexpected parameters (divergence) in response to treatment and the image output of the patient safety processor may be observed, and/or recorded for protocol modeling. Further, using the ability to introduce divergence, allows processed protocols or other protocols to be verified for reasonable redundancy to cover failures of systemic response.

This aggregation of data, analysis and metadata provide the source of data for the patient safety visualization processor 372. In one embodiment, the patient safety visualization process 372 provides a visualization of a patient's condition in a comprehensive grouping defined by rows of timelines of specific signals and/or grouping and/or categories of signals and/or signals. In one embodiment the global state of each row is represented by color in a spectrum with a different color for each of: sustained stability, stability, convergence, perturbation, divergence, null, failure, cascading failure.

In another embodiment colored arrows, icons, text, and/or other visual representations along each time line represent these states. In one embodiment the patient safety visualization processor represents the patient condition as a set of pixel streams moving from left to right to show evolution of condition over time. The processor provides the navigation backward and forward in time as well as up and down through levels of analysis within the patient safety image database 368. In an embodiment the levels of analysis may be, for example:

Time Series—Unanalyzed data streams in the form of time series

Events and Perturbation—Events and threshold violations characterized within their respective channels as to whether they represent clearly defined perturbation according to the event definition set 332

Systemic Response—Convergent, divergent and null binaries representing the relationships between events, threshold violations, perturbations and expected elements according to the binary definition set 344

Failure—aggregate failure objects representing images of failure that have been identified within a single patient System Failure—aggregate failure objects within a specific category (such as the respiratory system) representing images of failure that have been identified within a single patient Failure Patterns—Trends of failure and failure images within patient population or a specific region, such as a specific hospital ward for example.

In one embodiment the patient safety visualization processor 372 composes an image on computer monitor (the patient safety console 384), which is composed by a series of pixels oriented horizontally representing data and analysis streams. These pixel streams are stacked vertically with the position on the x-axis representing a specific point in time. The processor provides for the movement of the pixel streams horizontally to provide a pan through time.

Each pixel stream is composed of a set of pixels, which indicate the state of the data and/or analysis at the specified point in time. The pixel has a state (e.g., represented by color) and granularity (the length of time it represents [for example 1 minute]). The size of the view as well as the selected span of time determines the granularity of the pixel. In an embodiment, the pixel is displayed by the highest level of instability found within the time span represented by the single pixel within the pixel stream.

Further, each pixel has a level of abstraction, which determines which objects from the patient safety image database 368 contribute to its state. The contributing objects are shown below by level of analysis:

Time Series—data points within the channel (e.g., oxygen saturation values)
    Events and Perturbation—Events and threshold violations
    Systemic Response—Relational Binaries
    Failure—Aggregate Failure Objects
    Failure Patterns—Failure Trends and Correlations In an embodiment, groups of pixel streams are stacked vertically to create a patient safety visualization. Patient safety visualizations may be composed of pixel streams of different patients or of data and analysis streams within a single patient. Patient safety images provide the ability of the care worker to filter the analysis quickly to identify problem areas or areas of a specific nature. Sorting may be provided highlight emerging failure cascades or other pattern failures.

In an embodiment patient safety images may be composed of different levels of analysis displayed on the patient safety console 384 at the same time correlated by time. The use of mixed-analysis level visualizations provides the careworker with the ability to quickly understand the relationship between the lower levels of data (e.g., incomplete recovery within oximetry) and the higher levels of analysis (e.g., the identification of narcotic-induced ventilation instability).

In an embodiment the patient safety console 384 provides the user the ability to trace a failure condition back to the earliest events associated with the failure to provide a visual display of a failure cascade. Alternatively, individual events and threshold violations may be selected to identify which higher-level objects in which they played a part. In other words, low-level events may be traced forward to understand their relationship within evolving patient instability. This tracing, both backward and forward, is provided by the fact that alpha events of a relational binary are often the beta event of a preceding relational binary. This chain of relational binaries provides a powerful tool of analysis. The patient safety visualization processor provides the ability to isolate these binary chains showing their origin, evolution and resolution. In one embodiment, visualizations may be filtered by the existence and character of binary chains.

In one embodiment, and if selected by configuration, the patient safety visualization processor provides the ability to navigate into the metadata models at any point within the visualization. Event, convergence and failure image component diagrams are accessible from objects, which were composed using specified elements within these diagrams within the event definition set 332, binary definition set 344 and failure image component definition set 356. Navigation into the metadata models provides expert care workers and researchers the ability to further understand and/or alter the analysis.

The patient safety console 384 presents a complex set of data and analysis that meets the immediate need of the busy care worker. In one embodiment, analysis at the highest levels may be collapsed into a single pixel stream or group of pixel streams per patient that provides a simple representation of the evolution of overall patient safety. Within and from that pixel stream the care worker may drill down into the most complex displays: multiple levels of analysis, binary chains and metadata models to name a few. Alternatively this drill down may be provided by for example mouse over, touch screen, or may appear automatically when the processor detects certain adverse patterns or thresholds.

In one embodiment, the object stream visualization focuses on the relationships and cascading of the onset of perturbation within the patient. This is an alternate, and complimentary, view to the pixel streams described above which focus to a greater extent on the state of discrete elements within the system at various levels of analysis. These two visualizations may be used in parallel and/or provide navigation between them.

In an embodiment, the object stream visualization represents events and threshold violations as icons along a time series in which the icon is placed at the first point in time in which the event or threshold violation occurred. Icons indicate their character by color, size and decorations. The basic icon is an arrow pointing either up or down (as in FIG. 15A). An up arrow indicates a positive movement, which triggered an event whereas the down arrow indicates a negative movement. Boolean changes will be indicated as an up arrow when moving from false to true and a down arrow when moving from true to false. The thickness and/or color of the arrow may be used to indicate the extent of that movement.

Decorations on the arrow may be presented to provide visual cues as to the nature of the event. A line underneath the head of the arrow indicates that he event that occurred was a threshold violation. A circle around the arrow (see 979 of FIG. 15A) may be used to indicate that the event was the result of a action or test ordered by the Patient safety processor. Decorations and/or matching colors and/or flashings may be used to indicate a relationship warning by the processor, as in the warning of the potential relationship between the low platelet count and the medication clopidogrel in FIG. 18.

In one embodiment, the patient safety visualization processor 372 will provide automated visual navigation for a specified period of time and/or specified images. This automated visual navigation acts as an analysis-driven video playback of the selected period of time. The healthcare worker selects "Play" and allows the patient safety visualization processor to move visually through the evolution of a specified condition. The healthcare worker may choose navigation movements including "Play", "Pause", "Fast-Forward", "Rewind", "Skip Forward", "Skip Backward", to name a few. In an embodiment, during Play mode the patient safety visualization processor moves at different speeds through the automated visualization depending on the severity of the condition being displayed. If the timeseries being displayed have little perturbation (or little perturbation related to the specified failure cascade) the processor will move very quickly through time (i.e., from left to right). When an area of interest, as determined by the processor, comes into vision the patient safety visualization processor will slow the movement from left to right. Further, the patient safety visualization processor will highlight elements that indicate, clarify and specify the evolution and/or cascade of failure as well as their relationships with other elements. The patient safety visualization processor will further display translucent pop-up panels that provide further textual and/or visualization elements to describe the current view and elements within the current view. At any point, the healthcare worker may "Pause" the automated visual navigation to review the displayed data and/or drill into what has been displayed.

In an embodiment, the healthcare worker may select from a summary view a timespan to review and also indicate sections of the timespan for which they are interested. The patient safety visualization processor will slow for the areas selected that are of interest and will increase the textual and visualization display appropriately for the highlighted sections.

In one embodiment the patient safety visualization processor 304 selects the object streams to display and may include or remove streams as they become important in the video navigation. The healthcare worker may choose to include additional streams or to "pin" streams so as to make them always available in the video navigation. Missing streams are also indicated.

The patient safety visualization processor 372 may further indicate to the healthcare worker the time estimated for automated visual navigation (e.g., "Standard visual navigation estimated at 2 minutes and 37 seconds"). The patient safety visualization processor may include audio and visual elements corresponding to and synchronized with the timeseries data along with timeseries data if video and audio feeds are available. In an embodiment, healthcare workers may include audio and/or video comments into the data streams to communicated and collaborate regarding elements displayed within the patient safety visualization processor. The patient safety visualization processor may be directed to include all or a specified subset (e.g., "Include Comments from Doctor X") of these elements within the automated visual navigation or may be directed simply to indicate their presence such that the healthcare worker may invoke them as needed.

In an embodiment, the patient safety visualization processor 372 may "record" an automated visual navigation session into a non-interactive video format which may be viewed on standard video equipment, with streaming technology or in a standard media player such that automated visual navigation sessions may be shared with healthcare workers who do not have access to the patient safety image database or the patient safety visualization processor (e.g., as an attachment to an e-mail or accessed from a video-enabled phone).

Figure 23:
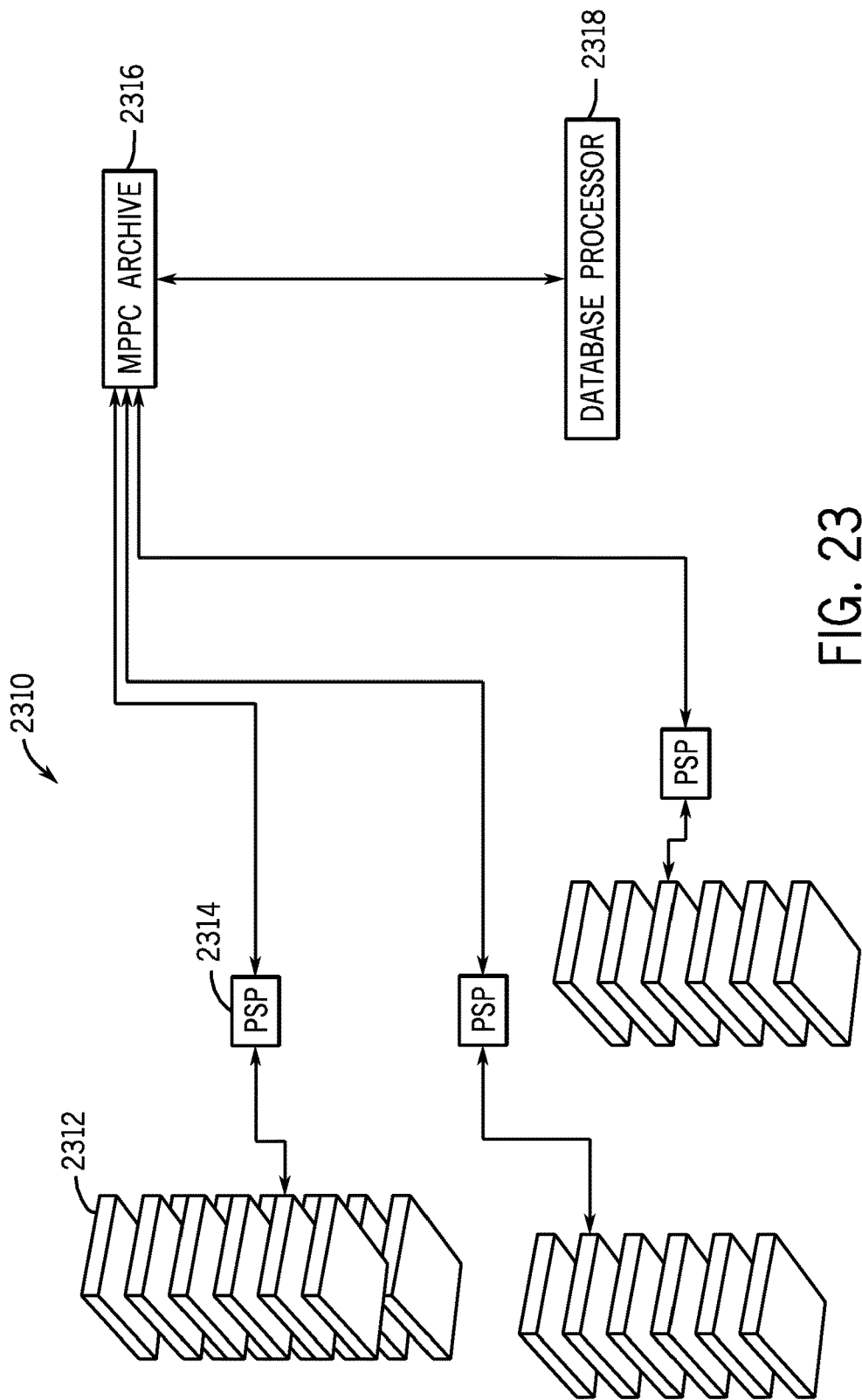
FIG. 23 is a diagram of an exemplary patient safety processor network.

In one embodiment, the processor 304 may use an archive or database of retrospective and/or theoretical model MPPCs as a source for determining best-fit image matches or as an ongoing model to improve such matches. As shown in FIG. 23, one embodiment is a patient safety processor network 2310 for archiving and cataloging a database of MPPCs and for developing improved failure mode recognition, improved protocolization, and improved access of rural and underserved hospitals to timely failure mode detection and intervention. As shown, the network 2310 may allow each hospital 2312, which are each in turn connected to respective patient safety processors 2314, to be connected to a central image archive, such as an MPPC archive 2316. The MPPCs from each patient safety processor 2314 are uploaded to the central MPPC archive 2316 from each hospital. The central MPPC archive is connected to the database processor 2318, which serves to process the MPPC from the central MPPC archive 2316 and to improve MPPC recognition and to develop new failure mode recognition and treatment protocols. MPPCs from a hospital patient safety processor 2314 that are classified as associated with an objectively known case, for example one that is confirmed independently through additional tests (e.g., histopathology, genetic testing) or autopsy results, such as a MPPC suggestive of pulmonary embolism including a positive pulmonary angiogram, are input to the processor 2318 to build an objectively defined MPPC database to further build the scope and specificity of the MPPC of pulmonary embolism. In the alternative, MPPCs that are classified as associated with an subjective final diagnosis, such as an MPPC suggestive of SLE induced alveolar hemorrhage, for example followed by a opinion of a consensus group that this was the final diagnosis, may be added to the subjectively defined MPPC database case database to further build the scope and specificity of the MPPC of SLE induced alveolar hemorrhage. In this manner, a large database may be derived from MPPC and image components of MPPC for the worldwide management of disease. International testing and treatment protocols based on the real-time MPPC detection may be developed that may potentially set a minimum standard of detection of catastrophic events even in rural hospitals with a few beds, in urban hospitals which are poorly staffed, and in environments wherein physician and nurse experience may be very low. New protocols may be derived and uploaded to these hospitals for their discretionary use as analysis of the MPPC results in response to older protocols or new or additional treatment outside the protocols reveals potential for improvement. The approach has the potential to provide improved surveillance of drug reactions and efficacy after, for example, the introduction of a new drug into a protocol that may be an experimental protocol. Missing portions of the MPPC may also be identified to support the development of new tests which fill in the gaps or perhaps reduce the number of tests ordered to define cause(s) of the failure. Cost comparison of different testing and treatment protocols may be performed.

The bandwidth of the MPPC may include tests, historic data, and treatments that become objects in the MPPC. When potentially clinically significant images of perturbation are identified in an MPPC, the patient safety processor is programmed to quickly broaden the bandwidth to investigate the alternative causes. This is important because the longer the duration an undetected failure mode the greater the increase in cost and mortality because complications develop with widen the cascade and make salvage more expensive and difficult. A narrow bandwidth (fewer tests) is, on the other hand (without considering the cost of allowing a longer duration of failure), less expensive than a broader bandwidth. The "effective bandwidth" includes those components of the bandwidth that actually contribute to characterize the factors actively defining the failure image components of the MPPC. Poorly conceived testing and treatment increases the bandwidth and the medical cost but may not increase the effective bandwidth. One object of the patient safety processors 2314 is to increase the effective bandwidth as rapidly as possible without broadening the bandwidth inordinately. In an embodiment, a patient safety processor medical system monitors with a few monitors and tests but uses these as sentinels, increasing the number of monitors and tests automatically if a MPPC begins.

Therefore, it may be advantageous to provide a mechanism to automatically increase the effective bandwidth of the MPPC at any time (for example, during low staff times in a rural hospital), to optimally shorten the duration of failure without the application of a continuously wide and expensive bandwidth. One mechanism to broaden bandwidth is with improved testing, such as focused tests that have a high sensitivity and specificity for a specific failure mode. The MPPC archive 2316 of the patient safety processor network 2300 may be examined for opportunities to increase the motion picture bandwidth and achieving a balanced mechanism for mortality and cost reduction by shortening the duration of failure through earlier detection and improved treatment response.

As discussed, according to one embodiment the patient safety processing network includes a set of local patient safety processors located at a hospital ward or unit. The local patient safety processor is under the direction of the healthcare workers at that location. This allows the local healthcare workers to control the treatment and testing protocols, and variation of the testing bandwidth, deployed for the patient under their control. The local attending physicians individually or as a group as well as the hospital pharmacists and nurses may prescribe these protocols though the use of the Local patient safety processors. The local patient safety processor records the healthcare worker(s) (for example as a step time series of with an rise event occurring when the physician, or nurse for example assumes responsibility and a fall event when he or she is replaced by another. Those caring for the patient are therefore part of the MPPC. Protocols may be decided by a group or by an individual physician caring for the patient. The extent to which a particular healthcare worker or group is statistically or otherwise associated with favorable or unfavorable MPPC may be assessed by the processor. The protocol choices for the local patient safety processors may be made through the use of pre prepared MPPC protocols as previously discussed.

The local patient safety processor may recognize the physician time-series and adjust the protocols and MPPC to match those selected by this physician. The physician may override the patient safety processor and if this occurs this override is an event rendering a new time series until the override is withdrawn. The extent to which a particular override is statistically or otherwise associated with favorable or unfavorable MPPC may be assessed by the hospital patient safety processor, the hospital group patient safety processor, or the database processor 18. These may provide modifications in future protocols, and even incorporation of the modification of the override or even the prevention of this type of override may be made accordingly.

The local patient safety processor s communicate with a hospital wide or hospital patient safety processor which is preferably under direction of the quality improvement committee and the hospital experts in each field. The hospital patient safety processor communicates with all the local patient safety processor s and may be used to upload treatment/and or testing and/or bandwidth adjustment protocols and or comparison MPPC, which have been agreed upon for application hospital-wide to the local patient safety processors.

The hospital patient safety processor s of single hospitals communicate with (and may be controlled by) central organization patient safety processor. The organization patient safety processor allows standardization of the hospital protocols through the Hospital patient safety processor s under its control to set a minimum safety treatment and testing standards and may be controlled by a centralized quality assurance group with expert representatives form all of the hospitals. Since the individuals caring for the patient represent at least one time series and the ward represents at least one time series and the hospital represents at least one time series and the organization represents at least one time series. The MMPP therefore includes all of these locations. If the Patient is wearing a monitored GPS unit this may comprise a location time series which provides continuous real time location as part of the MMPP. The patient safety processor will compare with the entered locations to identity convergence.

One embodiment demonstrates an example of how a new set of time series derived from testing devices and provided to the patient safety processor may be evaluated for cost effectiveness. In this example, a pulse oximetry reflectance probe is mounted (as by hat or headband or other fixation device above at least eye to the patient's head and the probe is wirelessly or otherwise connected to pulse oximeter and the local patient safety processor (as by Bluetooth for example). The transmitter may be mounted in the probe, on the headband or hat or behind the ear in the position of a hearing aid if desired. A position sensor may also be provided mounted on the patient. A maneuver such as a change in body position may be detected and included as an event by the patient safety processor and a fall a component of the photoplethysmographic pulse (indicative of the perfusion of the capillary bed distribution of the supra-orbital artery, a distal branch of the internal carotid) in relation to a maneuver. In this way the flow of the capillary bed above the eye becomes a surrogate marker of other capillary beds supplied from the internal carotids. Real time perfusion may be compared with that of the ear, fingertip, or the pulse pressure (as by an invasive arterial line for example) to identify disparate in perfusion in one or both of the internal carotid distribution. The local patient safety processor processes the MPPC with these as additional time-series. The local patient safety processor uploads the MPPC to the Hospital patient safety processor, and the hospital patient safety processor, organizational patient safety processor, and/or database processor 18 where the MPPCs may be evaluated to determine if after adjusting for disparities in the MPPCs as a function of co-morbidities. The MPPCs that include the time series derived from the supra-orbital plethysmographic pulse may be associated with a reduction in the number of falls in the hospital. If this is statistically significant, these time series may be automatically added (by automatically ordering the intermittent or continuous supra-orbital monitoring used the study) to increase the testing and bandwidth when it is detected that the MPPC of a given patient is similar to those of the study population where the addition of those processed time-series data had a positive impact on outcome.

The database processor 18 is preferably connected to all the organization patient safety processor s (or hospital patient safety processor s if the hospital is not under a central organization). The database processor 18 is preferably controlled by a healthcare information corporation which maintains the database processor 18 and the network. Each patient safety processor below the database processor 18 is capable of operating independent of the patient safety processor network so extensive redundancy, lack of subordinate dependency, and therefore greater safety against network failure is built into the patient safety processor network.

This patient safety processor network structure allows diverse minimum standards to be set by each government and allows the monitoring of the effects of these diverse minimum standards to determine cost and benefit. The database processor 18 preferably includes a comparison processor that compares the MPPC and all of the objects of the MPPC, such as events, binaries, image components, and cascades, to other MPPCs all of the objects of the other MPPCs to identify statically differences between the MPPC which are associated with improved or adverse cost, outcome, length of stay, morbidity, mortality, resource consumption, and/or complications. One advantage of the patient safety processor is that the objects of the MPPC are discrete and are therefore readily incorporated into statistical software components of the PSCP. The statistical software components may include a wide array of statistical software products as are well known in the art for identifying differences in discrete time related data collections. The objects also comprise organized collections of an ascending hierarchy of complexity and the organized collections which may be compared statistically at each ascending level of complexity to identify associated differences. In one embodiment the PSCP divides the MPPCs into groups having a least apportion of substantially the same image components. For example a grouping may be derived having substantially the same initial sepsis cascade picture and similar co morbidities and age and sex but different physicians, hospitals and/or treatments. Differences in length, progression, compilations and mortality associated with the cascade may be identified and statistically compared with the differences in physicians, hospitals, treatments, testing, and/or treatment timing.

When a particular testing, treatment, bandwidth variation, ward location, or hospital location is identified as statistically associated with improved outcome then the database processor 18 my offer, as for download, new protocols which incorporate those identified particulars into the hospital patient safety processors and/or Organization patient safety processors for their consideration. New medication or treatments may be assessed in this way with blinding of the data accommodated by the patient safety processor such that the time series of the experimental medical is labeled with an experimental code.

While the disclosed embodiments may be susceptible to various modifications and alternative forms, specific embodiments have been shown by way of example in the drawings and have been described in detail herein. However, it should be understood that the disclosure is not intended to be limited to the particular forms disclosed. Indeed, disclosed embodiments may not only be applied to clinical diagnosis of systems of physiological failure, but may be applied to any clinical condition that may be represented by images as provided herein. Indeed, the disclosed embodiments may be applied to monitor and/or diagnose conditions in which a patient's condition is generally improving, such as post-surgical monitoring. Rather, the disclosure is to cover all modifications, equivalents, and alternatives falling within the spirit and scope of the disclosed embodiment and as defined by the following appended claims.

What is claimed is:

1. A system for monitoring a plurality of patients in a hospital system to detect, in real time, the development of sepsis cascades and identify patients developing the sepsis cascades, the system comprising:
   a plurality of local patient safety monitors, each of the plurality of local patient safety monitors configured to receive physiological measurements from at least a pulse oximeter and a blood pressure monitor for one or more patients,
   a central patient safety monitor remote from the plurality of local patient safety monitors, the central patient safety monitor having a processor, and memory storing instructions that, when executed by the processor, cause the system to:
   receive at least the physiological measurements from the plurality of local patient safety monitors;
   search a database of laboratory data and physiologic parameters for perturbations of the laboratory data and physiologic parameters to identify a temporal grouping of at least four perturbations of the laboratory data and physiologic parameters associated with a patient, wherein the perturbations of the laboratory data and physiologic parameters are pathophysiologically linked, and wherein the database of laboratory data and physiologic parameters comprises an electronic medical record repository of data comprising data associated with a plurality of patients in at least one hospital;
   generate a sepsis cascade pattern based on the identified temporal grouping of at least four perturbations of the laboratory data and the physiologic parameters, wherein the sepsis cascade pattern is indicative of sepsis;
   associate the generated sepsis cascade pattern with the electronic medical record of the patient having the identified temporal grouping of at least four perturbations of the laboratory data and physiologic parameters; and
   convert the generated sepsis cascade pattern into one or more images indicating progress of the sepsis cascade pattern;
   send a notification to a patient safety console of at least one of the central patient safety monitor or one of the local patient safety monitors, for each patient of the one or more patients associated with a sepsis cascade pattern, an indication of the patient and the one or more images of the sepsis cascade pattern for the patient,
   wherein the notification causes the patient safety console to display the indication of each patient of the one or more patients having a sepsis cascade pattern and the one or more images of the sepsis cascade pattern for each patient.

2. The system of claim 1, wherein the memory stores additional instructions that, when executed by the processor, cause the system to:
   provide an automatic alarm at one of the central patient safety monitor and at least one of the plurality of local patient safety monitors based on identifying the one or more patients of the plurality of patients having the at least one sepsis cascade pattern.

3. The system of claim 1, wherein the at least one sepsis cascade pattern comprises a cascade of a progressively increasing number and severity of relational perturbations indicative of one or more of severe sepsis, septic shock, microcirculatory failure, or shock.

4. The system of claim 1, wherein the at least one sepsis cascade pattern comprises a plurality of linked perturbations or trends of physiologic and laboratory data defining a progressively enlarging aggregation of progressively greater numbers of perturbed physiologic and laboratory data.

5. The system of claim 1, wherein the memory stores additional instructions that, when executed by the processor, cause the system to:

determine at least one characteristic of the at least one sepsis cascade pattern, the at least one characteristic comprising one or more of a severity of the at least one sepsis cascade pattern, a duration of the at least one sepsis cascade pattern, a time of onset of the at least one sepsis cascade pattern, a maturity of the at least one sepsis cascade pattern, a timing relationship of the at least one sepsis cascade pattern to other events or another sepsis cascade pattern, a cost associated with the at least one sepsis cascade pattern, a global pattern of the at least one sepsis cascade pattern, a time of termination of the at least one sepsis cascade pattern, components of the at least one sepsis cascade pattern, a state of evolution of the at least one sepsis cascade pattern, a length of stay associated with the at least one sepsis cascade pattern, or treatments associated with the at least one sepsis cascade pattern.

6. The system of claim 5, wherein the at least one characteristic of the at least one sepsis cascade pattern is defined by one or more of a number of perturbations or trends which comprise the at least one sepsis cascade pattern, a severity of the perturbations or trends, a number of systems affected by the at least one sepsis cascade pattern, or a presence, number or severity of failure of compensation in response to perturbations associated with the at least one sepsis cascade pattern.

7. The system of claim 1, wherein the memory stores additional instructions that, when executed by the processor, cause the system to:
determine a rate of growth of the at least one sepsis cascade pattern.

8. The system of claim 1, wherein the memory stores additional instructions that, when executed by the processor, cause the system to:
determine a rate of growth of the at least one sepsis cascade pattern by at least one of an increase in number or severity of new perturbations being added per unit time, an increase in number of systems affected, or an increase in number of perturbations present in different systems.

9. The system of claim 1, wherein the memory stores additional instructions that, when executed by the processor, cause the system to:
detect events or components that are temporally or spatially associated with the at least one sepsis cascade pattern and are not part of the at least one sepsis cascade pattern.

10. The system of claim 1, wherein the memory stores additional instructions that, when executed by the processor, cause the system to:
convert electronic medical records from the electronic medical record repository of data into a format enabling the system to search for a sepsis cascade pattern.

11. The system of claim 10, wherein the format comprises sequential and timed variations comprised of at least positive variations and negative variations of the data.

12. The system of claim 10, wherein the electronic medical record repository of data comprises data from a plurality of hospitals, and wherein the memory stores additional instructions that, when executed by the processor, cause the system to:
identify the one or more patients of the plurality of patients having the at least one sepsis cascade patterns and one or more hospitals in which the one or more patients are located.

13. The system of claim 1, comprising: the patient safety console.

14. A system for monitoring a plurality of patients in a hospital system to detect, in real time, the development of sepsis cascades and identify patients developing the sepsis cascades, the system comprising:
a plurality of local patient safety monitors, each of the plurality of local patient safety monitors configured to receive physiological measurements from at least a pulse oximeter and a blood pressure monitor for one or more patients,
a central patient safety monitor remote from the plurality of local patient safety monitors, the central patient safety monitor having a processor, and memory storing instructions that, when executed by the processor, cause the system to:
convert electronic medical records of patients in at least one hospital into sequential and timed trends;
generate, from the sequential and timed trends, positive trends and negative trends of physiologic parameters and laboratory data;
determine, from the positive trends and negative trends, relational trends comprising a combination of positive trends or negative trends associated with the physiologic parameters and the laboratory data;
generate sepsis cascade patterns associated with a plurality of combinations of the relational trends;
convert the generated sepsis cascade patterns into one or more images based on the plurality of combinations of the relational trends;
generate a warning based on detecting the sepsis cascade patterns, the warning identifying at least one patient generating the sepsis cascade patterns;
determine a growth or a decline of the sepsis cascade patterns and generate an indication responsive to the growth or the decline of the sepsis cascade patterns; and
send a notification to a patient safety console of at least one of the central patient safety monitor or one of the local patient safety monitors including the image of the sepsis cascade patterns generated based on the plurality of combinations of the relational trends, the warning generated based on detecting the sepsis cascade patterns, and the indication responsive to the growth or the decline of the sepsis cascade patterns,
wherein the notification causes the patient safety console to display one or more of the image of the sepsis cascade patterns generated based on the plurality of combinations of the relational trends, the warning generated based on detecting the sepsis cascade patterns, or the indication responsive to the growth or the decline of the sepsis cascade patterns.

15. The system of claim 14, wherein the sepsis cascade patterns are indicative of physiologic failure.

16. The system of claim 15, wherein the physiologic failure is associated with one or more of severe septic shock, or microcirculatory failure.

17. The system of claim 14, wherein generating the image of the sepsis cascade patterns based on the plurality of combinations of the relational trends comprises generating at least one moving picture based on the plurality of combinations of the relational trends.

18. The system of claim 17, wherein the memory stores additional instructions that, when executed by the processor, cause the system to:
determine and output, to a user interface displaying the at least one moving picture, an indication of timing and type associated with the relational trends.

19. The system of claim 17, wherein the memory stores additional instructions that, when executed by the processor, cause the system to:
 determine and output, to a user interface displaying the at least one moving picture, an indication of length of a cascade.

20. The system of claim 17, wherein the memory stores additional instructions that, when executed by the processor, cause the system to:
 determine and output, to a user interface displaying the at least one moving picture, an indication of timing of therapy in relation to a cascade.

21. The system of claim 14, comprising: the patient safety console.

22. A system for monitoring a plurality of patients in a hospital system to detect, in real time, the development of sepsis cascades and identify patients developing the sepsis cascades, the system comprising:
 a plurality of local patient safety monitors, each of the plurality of local patient safety monitors configured to receive physiological measurements from at least a pulse oximeter and a blood pressure monitor for one or more patients,
 a central patient safety monitor remote from the plurality of local patient safety monitors, the central patient safety monitor having a processor and memory storing instructions that, when executed by the processor, cause the system to:
 receive at least the physiological measurements from the plurality of local patient safety monitors and store the physiological measurements in an electronic medical record;
 receive, from the electronic medical record, data associated with a plurality of patients in a hospital, the data being associated with a physiologic state for care of each patient of the plurality of patients in the hospital, and the data including at least the physiological measurements from the plurality of local patient safety patient monitors and one or more laboratory datasets derived from laboratory testing of blood samples associated with the plurality of patients in the hospital;
 convert the physiological measurements and the one or more laboratory datasets into a plurality of time series; and
 determine occurrences of perturbations associated with the plurality of time series by analyzing changes over time in each of the plurality of time series, the occurrences of perturbations associated with the plurality of time series comprising one or more of inflammatory occurrences, metabolic occurrences, volumetric occurrences, hemodynamic occurrences, therapy occurrences, hematologic occurrences, or respiratory occurrences;
 determine a timing of each of the occurrences of perturbations associated with the plurality of time series;
 generate an indication of a sepsis cascade responsive to identifying at least one relational pattern among the occurrences of perturbations associated with the plurality of time series and the determined timing of each of the occurrences of the perturbations, the sepsis cascade being defined by a temporal grouping of at least four of the occurrences of perturbations associated with the plurality of time series;
 generate an alarm notification responsive to the generated indication of the sepsis cascade, the alarm notification identifying a patient in the hospital generating the sepsis cascade; and
 send the alarm notification to a patient safety console of the central patient safety monitor or one of the local patient safety monitors in the hospital,
 wherein the alarm notification causes the patient safety console in the hospital to display one or more images of the sepsis cascade and information identifying the patient in the hospital generating the sepsis cascade.

23. The system of claim 22, comprising:
 the patient safety console;
 a blood pressure monitor; and
 a pulse oximeter,
 wherein the memory stores additional instructions that, when executed by the processor, cause the system to:
 receive, from the pulse oximeter, pulse oximetry data associated with at least one patient of the plurality of patients; and
 receive, from the blood pressure monitor, blood pressure data associated with the at least one patient of the plurality of patients, and
 wherein at least one of the occurrences of perturbations associated with the plurality of time series is identified based on the pulse oximetry data received from the pulse oximeter and the blood pressure data received from the blood pressure monitor.

24. A system for monitoring a plurality of patients in a hospital system to detect, in real time, the development of sepsis cascades and identify patients developing the sepsis cascades, the system comprising:
 a patient safety console;
 a plurality of blood pressure monitors;
 a plurality of pulse oximeters;
 a plurality of local patient safety monitors, each of the plurality of local patient safety monitors configured to receive physiological measurements from at least one of the plurality of pulse oximeters and at least one of the plurality of blood pressure monitors for one or more patients, and
 a central patient safety monitor remote from the plurality of local patient safety monitors, the central patient safety monitor having a processor and memory storing instructions that, when executed by the processor, cause the system to:
 receive at least the physiological measurements from the plurality of local patient safety monitors and store the physiological measurements in a database of laboratory data and physiologic parameters;
 search the database of laboratory data and physiologic parameters for perturbations of the laboratory data and physiologic parameters to identify a cascade pattern indicative of sepsis,
 wherein the cascade pattern indicative of sepsis is associated with a temporal grouping of at least four perturbations of the laboratory data and physiologic parameters,
 wherein the perturbations of the laboratory data and physiologic parameters are pathophysiologically linked,
 wherein the database of laboratory data and physiologic parameters comprises an electronic medical record repository of data comprising data associated with a plurality of patients in at least one hospital, and
 wherein the data associated with the plurality of patients in the at least one hospital comprises pulse oximetry data received from the pulse oximeter and blood pressure data received from the blood pressure monitor of at least one local patient safety monitor;

based on searching the database, identify one or more patients of the plurality of patients as having at least one sepsis cascade pattern, wherein the at least one sepsis cascade pattern comprises a plurality of linked perturbations or trends of physiologic and laboratory data defining a progressively enlarging aggregation of progressively greater numbers of perturbed physiologic and laboratory data;

send a notification to the patient safety console comprising an indication of each patient of the one or more patients identified as having the at least one sepsis cascade pattern and one or more images of the at least one sepsis cascade pattern, wherein the notification causes the patient safety console to display the indication of each patient of the one or more patients identified as having the at least one sepsis cascade pattern and the one or more images of the at least one sepsis cascade pattern;

determine at least one characteristic of the at least one sepsis cascade pattern, the at least one characteristic comprising one or more of a severity of the at least one sepsis cascade pattern, a duration of the at least one sepsis cascade pattern, a time of onset of the at least one sepsis cascade pattern, a maturity of the at least one sepsis cascade pattern, a timing relationship of the at least one sepsis cascade pattern to other events or another sepsis cascade pattern, a cost associated with the at least one sepsis cascade pattern, a global pattern of the at least one sepsis cascade pattern, a time of termination of the at least one sepsis cascade pattern, components of the at least one sepsis cascade pattern, a state of evolution of the at least one sepsis cascade pattern, a length of stay associated with the at least one sepsis cascade pattern, or treatments associated with the at least one sepsis cascade pattern;

output, to a graphical user interface displayed on the patient safety console, the at least one characteristic of the at least one sepsis cascade pattern;

determine a rate of growth of the at least one sepsis cascade pattern by at least one of an increase in number or severity of new perturbations being added per unit time, an increase in number of systems affected, or an increase in number of perturbations present in different systems;

output, to the graphical user interface displayed on the patient safety console, the rate of growth of the at least one sepsis cascade pattern, generate at least one moving picture based on the identified sepsis cascade pattern to illustrate the progress of the sepsis cascade pattern over time, and output the generated moving picture, to the graphical user interface, wherein the graphical user interface includes viewing regions corresponding to physiologic systems of the patient, the viewing regions including at least an inflammatory region, and wherein the viewing regions are configured so that the moving picture is displayed such that the identified sepsis cascade pattern is viewable spreading over time within or across at least the inflammatory region as the severity of the sepsis cascade pattern progresses over time from the origin of the sepsis cascade to the termination of the sepsis cascade.

* * * * *